(12) United States Patent
Radovic-Moreno et al.

(10) Patent No.: US 10,894,963 B2
(45) Date of Patent: Jan. 19, 2021

(54) SPHERICAL NUCLEIC ACID-BASED CONSTRUCTS AS IMMUNOSTIMULATORY AGENTS FOR PROPHYLACTIC AND THERAPEUTIC USE

(71) Applicant: Exicure, Inc., Chicago, IL (US)

(72) Inventors: Aleksandar Filip Radovic-Moreno, Evanston, IL (US); Christopher C. Mader, Cambridge, MA (US); Subbarao Nallagatla, Chicago, IL (US); Warefta Hasan, Houston, TX (US); Aaron Love, Chicago, IL (US); Sergei Gryaznov, San Mateo, CA (US)

(73) Assignee: Exicure, Inc., Chicago, IL (US)

( * ) Notice: Subject to any disclaimer, the term of this patent is extended or adjusted under 35 U.S.C. 154(b) by 934 days.

(21) Appl. No.: 14/907,430

(22) PCT Filed: Jul. 25, 2014

(86) PCT No.: PCT/US2014/048291
§ 371 (c)(1),
(2) Date: Jan. 25, 2016

(87) PCT Pub. No.: WO2015/013673
PCT Pub. Date: Jan. 29, 2015

(65) Prior Publication Data
US 2016/0186178 A1 Jun. 30, 2016

Related U.S. Application Data

(60) Provisional application No. 61/858,558, filed on Jul. 25, 2013.

(51) Int. Cl.
*C12N 15/117* (2010.01)
*A61K 39/39* (2006.01)
*B82Y 5/00* (2011.01)
*A61K 39/00* (2006.01)

(52) U.S. Cl.
CPC ............ *C12N 15/117* (2013.01); *A61K 39/39* (2013.01); *A61K 2039/55561* (2013.01); *B82Y 5/00* (2013.01); *C12N 2310/17* (2013.01); *C12N 2320/30* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,289,872 A | 9/1981 | Denkewalter et al. |
| 4,469,863 A | 9/1984 | Ts'o et al. |
| 4,489,055 A | 12/1984 | Couvreur et al. |
| 4,904,582 A | 2/1990 | Tullis |
| 4,958,013 A | 9/1990 | Letsinger |
| 5,008,050 A | 4/1991 | Cullis et al. |
| 5,134,066 A | 7/1992 | Rogers et al. |
| 5,138,045 A | 8/1992 | Cook et al. |
| 5,166,315 A | 11/1992 | Summerton et al. |
| 5,177,196 A | 1/1993 | Meyer, Jr. et al. |
| 5,188,897 A | 2/1993 | Suhadolnik et al. |
| 5,216,141 A | 6/1993 | Benner |
| 5,229,490 A | 7/1993 | Tam |
| 5,256,775 A | 10/1993 | Froehler |
| 5,264,423 A | 11/1993 | Cohen et al. |
| 5,264,618 A | 11/1993 | Feigner et al. |
| 5,276,019 A | 1/1994 | Cohen et al. |
| 5,286,717 A | 2/1994 | Cohen et al. |
| 5,359,044 A | 10/1994 | Cook et al. |
| 5,399,676 A | 3/1995 | Froehler |
| 5,405,939 A | 4/1995 | Suhadolnik et al. |
| 5,434,257 A | 7/1995 | Matteucci et al. |
| 5,455,233 A | 10/1995 | Spielvogel et al. |
| 5,457,187 A | 10/1995 | Gmeiner et al. |
| 5,466,786 A | 11/1995 | Buhr et al. |
| 5,472,881 A | 12/1995 | Beebe et al. |
| 5,484,908 A | 1/1996 | Froehler et al. |
| 5,489,677 A | 2/1996 | Sanghvi et al. |
| 5,519,126 A | 5/1996 | Hecht |
| 5,519,134 A | 5/1996 | Acevedo et al. |
| 5,541,307 A | 7/1996 | Cook et al. |
| 5,552,540 A | 9/1996 | Haralambidis |
| 5,576,427 A | 11/1996 | Cook et al. |
| 5,578,718 A | 11/1996 | Cook et al. |

(Continued)

FOREIGN PATENT DOCUMENTS

| | | |
|---|---|---|
| AR | 070368 A2 | 3/2010 |
| AU | 2004218696 A1 | 11/2004 |

(Continued)

OTHER PUBLICATIONS

International Search Report and Written Opinion dated Dec. 15, 2014 for PCT/US2014/048291.
International Preliminary Report on Patentability dated Jan. 26, 2016 for PCT/US2014/048291.
International Search Report and Written Opinion dated Dec. 17, 2014 for PCT/US2014/048294.
International Preliminary Report on Patentability dated Feb. 4, 2016 for PCT/US2014/048294.
International Search Report and Written Opinion dated Jul. 8, 2015 for PCT/US2015/024255.
International Search Report and Written Opinion dated Oct. 13, 2015 for PCT/US2015/034226.
International Search Report and Written Opinion dated Sep. 30, 2015 for PCT/US2015/038771.

(Continued)

*Primary Examiner* — Michael D Burkhart
(74) *Attorney, Agent, or Firm* — Wolf, Greenfield & Sacks, P.C.

(57) ABSTRACT

Aspects of the invention relate to spherical nucleic acid-based constructs and related methods and compositions thereof. The compositions of the invention are useful for activating agonists of nucleic acid interacting complexes, such as TLRs, stimulating an immune response, and treating diseases such as infectious disease, cancer, allergies, allergic diseases, and autoimmune disease

16 Claims, 24 Drawing Sheets

Specification includes a Sequence Listing.

(56) References Cited

U.S. PATENT DOCUMENTS

| | | |
|---|---|---|
| 5,587,361 A | 12/1996 | Cook et al. |
| 5,587,371 A | 12/1996 | Sessler et al. |
| 5,591,722 A | 1/1997 | Montgomery et al. |
| 5,594,121 A | 1/1997 | Froehler et al. |
| 5,596,091 A | 1/1997 | Switzer |
| 5,602,240 A | 2/1997 | De Mesmaeker et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,269 A | 7/1997 | Matteucci et al. |
| 5,663,312 A | 9/1997 | Chaturvedula |
| 5,677,437 A | 10/1997 | Teng et al. |
| 5,677,439 A | 10/1997 | Weis et al. |
| 5,700,922 A | 12/1997 | Cook |
| 5,780,448 A | 7/1998 | Davis |
| 5,792,608 A | 8/1998 | Swaminathan et al. |
| 5,814,666 A | 9/1998 | Green et al. |
| 5,955,589 A | 9/1999 | Cook et al. |
| 6,051,698 A | 4/2000 | Janjic et al. |
| 6,080,580 A | 6/2000 | Baker et al. |
| 6,194,388 B1 | 2/2001 | Krieg et al. |
| 6,207,646 B1 | 3/2001 | Krieg et al. |
| 6,239,116 B1 | 5/2001 | Krieg et al. |
| 6,271,209 B1 | 8/2001 | Smith et al. |
| 6,361,944 B1 | 3/2002 | Mirkin et al. |
| 6,406,705 B1 | 6/2002 | Davis et al. |
| 6,417,340 B1 | 7/2002 | Mirkin et al. |
| 6,495,324 B1 | 12/2002 | Mirkin et al. |
| 6,506,564 B1 | 1/2003 | Mirkin et al. |
| 6,534,062 B2 | 3/2003 | Raz et al. |
| 6,582,921 B2 | 6/2003 | Mirkin et al. |
| 6,602,669 B2 | 8/2003 | Letsinger et al. |
| 6,610,308 B1 | 8/2003 | Haensler |
| 6,610,491 B2 | 8/2003 | Mirkin et al. |
| 6,677,153 B2 | 1/2004 | Iversen |
| 6,849,725 B2 | 2/2005 | Junghans et al. |
| 7,129,222 B2 | 10/2006 | Van Nest et al. |
| 7,223,741 B2 | 5/2007 | Krieg |
| 7,238,472 B2 | 7/2007 | Mirkin et al. |
| 7,250,403 B2 | 7/2007 | van Nest et al. |
| 7,255,868 B2 | 8/2007 | Fearon et al. |
| 7,291,284 B2 | 11/2007 | Mirkin et al. |
| 7,332,586 B2 | 2/2008 | Franzen et al. |
| 7,354,907 B2 | 4/2008 | Agrawal et al. |
| 7,387,271 B2 | 6/2008 | Noelle et al. |
| 7,427,405 B2 | 9/2008 | Agrawal et al. |
| 7,563,618 B2 | 7/2009 | Gryaznov et al. |
| 7,569,554 B2 | 8/2009 | Kandimalla et al. |
| 7,615,539 B2 | 11/2009 | Uhlmann et al. |
| 7,628,990 B2 | 12/2009 | Tuck et al. |
| 7,666,674 B2 | 2/2010 | Klinman et al. |
| 7,718,622 B2 | 5/2010 | Tuck et al. |
| 7,833,992 B2 | 11/2010 | Vargeese et al. |
| 7,850,990 B2 | 12/2010 | Tardi et al. |
| 7,875,594 B2 | 1/2011 | Kandimalla et al. |
| 7,884,083 B2 | 2/2011 | van Nest et al. |
| 7,993,659 B2 | 8/2011 | Noelle et al. |
| 8,008,267 B2 | 8/2011 | Kandimalla et al. |
| 8,058,249 B2 | 11/2011 | Krieg et al. |
| 8,088,388 B2 | 1/2012 | Sokoll |
| 8,124,590 B2 | 2/2012 | van Nest et al. |
| 8,158,768 B2 | 4/2012 | Dina et al. |
| 8,309,527 B2 | 11/2012 | Krieg et al. |
| 8,323,686 B2 | 12/2012 | Mirkin et al. |
| 8,333,980 B2 | 12/2012 | van Nest et al. |
| 8,507,200 B2 | 8/2013 | Mirkin et al. |
| 8,846,080 B2 | 9/2014 | Biemans et al. |
| 8,871,732 B2 | 10/2014 | Dina et al. |
| 8,889,181 B2 | 11/2014 | Kwon |
| 8,933,046 B2 | 1/2015 | Machuy et al. |
| 8,945,590 B2 | 2/2015 | Fairman et al. |
| 8,968,746 B2 | 3/2015 | Baumhof et al. |
| 9,061,001 B2 | 6/2015 | van Drunen Littel-van den Hurk et al. |
| 9,066,978 B2 | 6/2015 | Ilyinskii et al. |
| 9,132,281 B2 | 9/2015 | Zeng et al. |
| 9,169,325 B2 | 10/2015 | Keler et al. |
| 9,192,667 B2 | 11/2015 | Hoves et al. |
| 9,212,366 B2 | 12/2015 | Wittig et al. |
| 9,216,155 B2 | 12/2015 | Thaxton et al. |
| 9,265,729 B2 | 2/2016 | Nakamura |
| 9,364,443 B2 | 6/2016 | Beduneau et al. |
| 9,499,815 B1 | 11/2016 | Schroff et al. |
| 9,522,958 B2 | 12/2016 | Epstein et al. |
| 9,532,948 B2 | 1/2017 | Mirkin et al. |
| 9,549,901 B2 | 1/2017 | Shi et al. |
| 9,617,547 B2 | 4/2017 | Gemba |
| 9,693,957 B2 | 7/2017 | Lin et al. |
| 9,764,031 B2 | 9/2017 | Ilyinskii et al. |
| 9,901,616 B2 | 2/2018 | Dhar et al. |
| 9,907,845 B2 | 3/2018 | Reed et al. |
| 9,907,862 B2 | 3/2018 | Baumhof et al. |
| 9,950,063 B2 | 4/2018 | Reed et al. |
| 9,968,673 B2 | 5/2018 | Navarro y Garcia et al. |
| 9,987,355 B2 | 6/2018 | Reed et al. |
| 9,999,673 B2 | 6/2018 | Rajeev et al. |
| 10,029,016 B2 | 7/2018 | Irvine et al. |
| 10,098,958 B2 | 10/2018 | Mirkin et al. |
| 10,117,919 B2 | 11/2018 | Knutson et al. |
| 10,182,988 B2 | 1/2019 | Mirkin et al. |
| 10,196,643 B2 | 2/2019 | Dina et al. |
| 10,208,310 B2 | 2/2019 | Mader et al. |
| 10,434,064 B2 | 10/2019 | Radovic-Moreno et al. |
| 10,456,463 B2 | 10/2019 | Davis et al. |
| 10,487,333 B2 | 11/2019 | Schroff et al. |
| 10,604,760 B2 | 3/2020 | Schroff et al. |
| 2002/0156033 A1 | 10/2002 | Bratzler et al. |
| 2002/0172711 A1 | 11/2002 | Martin et al. |
| 2002/0197269 A1 | 12/2002 | Lingnau et al. |
| 2003/0026782 A1 | 2/2003 | Krieg |
| 2003/0050261 A1 | 3/2003 | Krieg et al. |
| 2003/0091599 A1 | 5/2003 | Davis et al. |
| 2003/0104044 A1 | 6/2003 | Semple et al. |
| 2003/0129251 A1 | 7/2003 | Van Nest et al. |
| 2003/0133988 A1 | 7/2003 | Fearon et al. |
| 2003/0138413 A1 | 7/2003 | Vicari et al. |
| 2003/0147966 A1 | 8/2003 | Franzen et al. |
| 2003/0170162 A1 | 9/2003 | Nayfeh et al. |
| 2003/0212026 A1 | 11/2003 | Krieg et al. |
| 2004/0053384 A1 | 3/2004 | Sligar et al. |
| 2004/0087534 A1 | 5/2004 | Krieg et al. |
| 2004/0092468 A1 | 5/2004 | Schwartz |
| 2004/0131628 A1 | 7/2004 | Bratzler et al. |
| 2004/0143112 A1 | 7/2004 | Krieg et al. |
| 2004/0158051 A1 | 8/2004 | Ozkan et al. |
| 2004/0170560 A1 | 9/2004 | Fossheim et al. |
| 2004/0247680 A1 | 12/2004 | Farokhzad et al. |
| 2004/0266719 A1 | 12/2004 | McCluskie et al. |
| 2005/0009773 A1 | 1/2005 | Kandimalla et al. |
| 2005/0089890 A1 | 4/2005 | Cubicciotti |
| 2005/0096263 A1 | 5/2005 | Keay et al. |
| 2005/0136258 A1 | 6/2005 | Nie et al. |
| 2005/0169888 A1 | 8/2005 | Hartmann et al. |
| 2006/0002949 A1 | 1/2006 | Glenn et al. |
| 2006/0003962 A1 | 1/2006 | Ahluwalia et al. |
| 2006/0014713 A1 | 1/2006 | Agrawal et al. |
| 2006/0019916 A1 | 1/2006 | Krieg et al. |
| 2006/0083781 A1 | 4/2006 | Shastri et al. |
| 2006/0105343 A1 | 5/2006 | Zetter et al. |
| 2006/0159921 A1 | 7/2006 | Murthy et al. |
| 2006/0183247 A1 | 8/2006 | Kim et al. |
| 2006/0188560 A1 | 8/2006 | Cheresh et al. |
| 2006/0233712 A1 | 10/2006 | Penades et al. |
| 2006/0251623 A1 | 11/2006 | Bachmann et al. |
| 2006/0275371 A1 | 12/2006 | Dai et al. |
| 2006/0292174 A1 | 12/2006 | De Los Rios et al. |
| 2007/0066554 A1 | 3/2007 | Krieg et al. |
| 2007/0148251 A1 | 6/2007 | Hossainy et al. |
| 2007/0184068 A1 | 8/2007 | Renner et al. |
| 2007/0218501 A1 | 9/2007 | Fogelman et al. |

(56) References Cited

U.S. PATENT DOCUMENTS

| | | |
|---|---|---|
| 2007/0243196 A1 | 10/2007 | Bruck et al. |
| 2007/0249555 A1 | 10/2007 | Barbaras et al. |
| 2007/0298257 A1 | 12/2007 | Ludwig et al. |
| 2008/0003232 A1 | 1/2008 | Wang et al. |
| 2008/0057128 A1 | 3/2008 | Li et al. |
| 2008/0124366 A1 | 5/2008 | Ohlfest et al. |
| 2008/0181928 A1 | 7/2008 | Hakimi-Mehr et al. |
| 2008/0194463 A1 | 8/2008 | Weller et al. |
| 2008/0206265 A1 | 8/2008 | Kandimalla et al. |
| 2008/0213177 A1 | 9/2008 | Rademacher et al. |
| 2008/0274454 A1 | 11/2008 | Mirkin et al. |
| 2008/0305106 A1 | 12/2008 | Brennan et al. |
| 2008/0306016 A1 | 12/2008 | Mirkin et al. |
| 2008/0311182 A1 | 12/2008 | Ferrari et al. |
| 2008/0317768 A1 | 12/2008 | Bianchi |
| 2009/0035576 A1 | 2/2009 | Prasad et al. |
| 2009/0053169 A1 | 2/2009 | Castillo et al. |
| 2009/0081157 A1 | 3/2009 | Kornbluth et al. |
| 2009/0081244 A1 | 3/2009 | Glenn et al. |
| 2009/0148384 A1 | 6/2009 | Fischer et al. |
| 2009/0155173 A1 | 6/2009 | Scherman et al. |
| 2009/0191188 A1 | 7/2009 | Krieg et al. |
| 2009/0209629 A1 | 8/2009 | Mirkin et al. |
| 2009/0286853 A1 | 11/2009 | Gryaznov et al. |
| 2009/0317802 A1 | 12/2009 | Bhatia et al. |
| 2009/0324706 A1 | 12/2009 | Mirkin et al. |
| 2010/0003287 A1 | 1/2010 | Mills et al. |
| 2010/0003317 A1 | 1/2010 | Akinc et al. |
| 2010/0011968 A1 | 1/2010 | Fin et al. |
| 2010/0111968 A1 | 5/2010 | Branigan et al. |
| 2010/0136682 A1 | 6/2010 | Mirkin et al. |
| 2010/0144848 A1 | 6/2010 | Vogel et al. |
| 2010/0166842 A1 | 7/2010 | Lu et al. |
| 2010/0167051 A1 | 7/2010 | Goia et al. |
| 2010/0183504 A1 | 7/2010 | Chen |
| 2010/0183634 A1 | 7/2010 | Luo et al. |
| 2010/0184844 A1 | 7/2010 | Mirkin et al. |
| 2010/0203142 A1 | 8/2010 | Zhang et al. |
| 2010/0233084 A1 | 9/2010 | Narasimhaswamy et al. |
| 2010/0233141 A1 | 9/2010 | Polach et al. |
| 2010/0233270 A1 | 9/2010 | Mirkin et al. |
| 2011/0020242 A1 | 1/2011 | Zheng et al. |
| 2011/0034422 A1 | 2/2011 | Kannan et al. |
| 2011/0052680 A1 | 3/2011 | Hendrickson |
| 2011/0052697 A1 | 3/2011 | Farokhzad et al. |
| 2011/0111974 A1 | 5/2011 | Mirkin et al. |
| 2011/0158937 A1 | 6/2011 | Kandimalla et al. |
| 2011/0159081 A1 | 6/2011 | Biemans et al. |
| 2011/0201672 A1 | 8/2011 | Krieg et al. |
| 2011/0237435 A1 | 9/2011 | Ryan |
| 2011/0262347 A1 | 10/2011 | Ruoslahti et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2011/0305734 A1 | 12/2011 | Edelson et al. |
| 2012/0093914 A1 | 4/2012 | Schubert |
| 2012/0107303 A1 | 5/2012 | Kandimalla et al. |
| 2012/0149843 A1 | 6/2012 | Chien et al. |
| 2012/0231041 A1 | 9/2012 | Fuchs et al. |
| 2012/0244230 A1 | 9/2012 | Mirkin et al. |
| 2012/0258126 A1 | 10/2012 | Scholler et al. |
| 2012/0282186 A1 | 11/2012 | Mirkin et al. |
| 2012/0288935 A1 | 11/2012 | Mirkin et al. |
| 2012/0301499 A1 | 11/2012 | Bachmann et al. |
| 2013/0028857 A1 | 1/2013 | Gao et al. |
| 2013/0034599 A1 | 2/2013 | Thaxton et al. |
| 2013/0071403 A1 | 3/2013 | Rolland et al. |
| 2013/0089614 A1 | 4/2013 | Zhang et al. |
| 2013/0095039 A1 | 4/2013 | Lu et al. |
| 2013/0101512 A1 | 4/2013 | Mirkin et al. |
| 2013/0123333 A1 | 5/2013 | Mirkin et al. |
| 2013/0149374 A1 | 6/2013 | Lee et al. |
| 2013/0178610 A1 | 7/2013 | Mirkin et al. |
| 2013/0196951 A1 | 8/2013 | Schoenfisch et al. |
| 2013/0252852 A1 | 9/2013 | Pfeiffer et al. |
| 2013/0295129 A1 | 11/2013 | Irvine et al. |
| 2013/0315831 A1 | 11/2013 | Shi et al. |
| 2014/0005258 A1 | 1/2014 | Mirkin et al. |
| 2014/0065425 A1 | 3/2014 | Bogdanov |
| 2014/0199379 A1 | 7/2014 | Tartour et al. |
| 2014/0227327 A1 | 8/2014 | Bencherif et al. |
| 2014/0294927 A1 | 10/2014 | Thaxton et al. |
| 2015/0064255 A1 | 3/2015 | Thaxton et al. |
| 2015/0086985 A1 | 3/2015 | Giljohann et al. |
| 2015/0111790 A1 | 4/2015 | Ategeka et al. |
| 2015/0118264 A1 | 4/2015 | Baumhof et al. |
| 2015/0182543 A1 | 7/2015 | Schoenfisch et al. |
| 2016/0186178 A1* | 6/2016 | Radovic-Moreno .............. A61K 39/39 424/184.1 |
| 2016/0194642 A1 | 7/2016 | Gryaznov et al. |
| 2016/0274134 A1 | 9/2016 | Mutharasan et al. |
| 2016/0310425 A1 | 10/2016 | Mirkin et al. |
| 2016/0375115 A1 | 12/2016 | Binder et al. |
| 2017/0044544 A1 | 2/2017 | Mirkin et al. |
| 2017/0175121 A1 | 6/2017 | Gryaznov |
| 2018/0042848 A1 | 2/2018 | Gryaznov et al. |
| 2018/0043023 A1 | 2/2018 | Ilyinskii et al. |
| 2018/0200381 A1 | 7/2018 | Kannan et al. |
| 2018/0214376 A1 | 8/2018 | Giljohann |
| 2018/0320184 A1 | 11/2018 | Radovic-Moreno et al. |
| 2018/0327741 A1 | 11/2018 | Daniel et al. |
| 2019/0142739 A1 | 5/2019 | Patel et al. |
| 2019/0211338 A1 | 7/2019 | Mader et al. |
| 2019/0225968 A1 | 7/2019 | Anderson et al. |
| 2019/0374650 A1 | 12/2019 | Moon et al. |
| 2019/0382492 A1 | 12/2019 | Goldberg et al. |
| 2020/0022913 A1 | 1/2020 | Mirkin et al. |
| 2020/0054663 A1 | 2/2020 | Agrawal et al. |
| 2020/0069587 A1 | 3/2020 | Radovic-Moreno et al. |
| 2020/0101102 A1 | 4/2020 | Wang et al. |
| 2020/0138848 A1 | 5/2020 | Agrawal et al. |

FOREIGN PATENT DOCUMENTS

| | | |
|---|---|---|
| CN | 101180400 A | 5/2008 |
| CN | 102036652 A | 4/2011 |
| CN | 103212089 A | 7/2013 |
| EP | 1 072 679 A2 | 1/2001 |
| EP | 1 221 955 B1 | 9/2005 |
| EP | 1 628 531 A2 | 3/2006 |
| EP | 1674128 A1 | 6/2006 |
| EP | 1 700 603 A3 | 6/2007 |
| EP | 1 802 757 A2 | 7/2007 |
| EP | 1 991 678 A2 | 11/2008 |
| EP | 2 162 117 A2 | 3/2010 |
| EP | 2399608 A1 | 12/2011 |
| EP | 2656858 A1 | 10/2013 |
| EP | 2759306 B1 | 4/2016 |
| EP | 2 360 252 B1 | 2/2017 |
| JP | 2006-513175 A | 4/2006 |
| JP | 2011-507807 | 3/2011 |
| JP | 2011-517676 A | 6/2011 |
| JP | 2011-518826 | 6/2011 |
| JP | 2011-519847 A | 7/2011 |
| JP | 2013-525285 A | 6/2013 |
| JP | 2014-503475 A | 2/2014 |
| WO | WO 92/21330 | 12/1992 |
| WO | WO 93/21528 A1 | 10/1993 |
| WO | WO 96/34876 A1 | 11/1996 |
| WO | WO 97/12896 A1 | 4/1997 |
| WO | WO 1998/047343 A2 | 10/1998 |
| WO | WO 2000/020645 | 4/2000 |
| WO | WO 2000/043045 A1 | 7/2000 |
| WO | WO 2001/000876 A1 | 1/2001 |
| WO | WO 2001/003709 A1 | 1/2001 |
| WO | WO 2001/049869 A1 | 7/2001 |
| WO | WO 2002/096262 A2 | 12/2002 |
| WO | WO 2003/008539 A2 | 1/2003 |
| WO | WO 03/030941 A1 | 4/2003 |
| WO | WO 2003/051278 A2 | 6/2003 |
| WO | WO 03/065991 A2 | 8/2003 |
| WO | WO 2004/047870 A1 | 6/2004 |
| WO | WO 2005/008222 A2 | 1/2005 |

(56) References Cited

FOREIGN PATENT DOCUMENTS

| | | |
|---|---|---|
| WO | WO 2005/009355 A2 | 2/2005 |
| WO | WO 2005/063201 A2 | 7/2005 |
| WO | WO 2005/063288 A1 | 7/2005 |
| WO | WO 2005/068020 A1 | 7/2005 |
| WO | WO 2005/116226 A2 | 12/2005 |
| WO | WO 2006/012695 A1 | 2/2006 |
| WO | WO 2006/110350 A2 | 10/2006 |
| WO | WO 2006/110350 A3 | 10/2006 |
| WO | WO 2006/128121 A2 | 11/2006 |
| WO | WO 2006/138145 A1 | 12/2006 |
| WO | WO 2007/008463 A2 | 1/2007 |
| WO | WO 2007/047455 A2 | 4/2007 |
| WO | WO 2007/089607 A2 | 8/2007 |
| WO | WO 2007/096134 A1 | 8/2007 |
| WO | WO 2007/106683 A2 | 9/2007 |
| WO | WO 2007/122405 A1 | 11/2007 |
| WO | WO 2008/014979 A2 | 2/2008 |
| WO | WO 2008/42156 A1 | 4/2008 |
| WO | WO 2008/097328 A2 | 8/2008 |
| WO | WO 2008/098248 A2 | 8/2008 |
| WO | WO 2008/127789 A2 | 10/2008 |
| WO | WO 2008/141289 A1 | 11/2008 |
| WO | WO 2009/012786 A2 | 1/2009 |
| WO | WO 2009/051451 A2 | 4/2009 |
| WO | WO 2009/061515 A1 | 5/2009 |
| WO | WO 2009/072657 A1 | 6/2009 |
| WO | WO 2009/073984 A1 | 6/2009 |
| WO | WO 2009/105260 | 8/2009 |
| WO | WO 2009/131704 | 10/2009 |
| WO | WO 2009/131931 A1 | 10/2009 |
| WO | WO 2009/133378 A2 | 11/2009 |
| WO | WO 2009/120887 A3 | 12/2009 |
| WO | WO 2010/017152 | 2/2010 |
| WO | WO 2010/017154 | 2/2010 |
| WO | WO 2010/081049 A1 | 7/2010 |
| WO | WO 2010/088395 A2 | 8/2010 |
| WO | WO 2010/091293 A1 | 8/2010 |
| WO | WO 2010/105209 A1 | 9/2010 |
| WO | WO 2010/120420 | 10/2010 |
| WO | WO 2010/137037 A2 | 12/2010 |
| WO | WO 2010/148249 A1 | 12/2010 |
| WO | WO 2011/017456 A2 | 2/2011 |
| WO | WO 2011/017690 A2 | 2/2011 |
| WO | WO 2011/037973 A1 | 3/2011 |
| WO | WO 2010/147387 A3 | 5/2011 |
| WO | WO 2011/053940 A2 | 5/2011 |
| WO | WO 2011/072133 A1 | 6/2011 |
| WO | WO 2011/079290 A1 | 6/2011 |
| WO | WO 2011/091065 A2 | 7/2011 |
| WO | WO 2011/113054 A2 | 9/2011 |
| WO | WO 2011/127405 A1 | 10/2011 |
| WO | WO 2011/139769 A1 | 11/2011 |
| WO | WO 2012/006634 A2 | 1/2012 |
| WO | WO 2012/055933 A1 | 5/2012 |
| WO | WO 2012/084991 A1 | 6/2012 |
| WO | WO 2013/012628 A2 | 1/2013 |
| WO | WO 2013/036974 A1 | 3/2013 |
| WO | WO 2013/043647 A1 | 3/2013 |
| WO | WO 2013/049941 A1 | 4/2013 |
| WO | WO 2013/098813 A1 | 7/2013 |
| WO | WO 2013/151771 A1 | 10/2013 |
| WO | WO 2013/177419 A1 | 11/2013 |
| WO | WO 2014/012479 A1 | 1/2014 |
| WO | WO 2014/025795 A1 | 2/2014 |
| WO | WO 2014/123935 A1 | 8/2014 |
| WO | WO 2014/133547 A1 | 9/2014 |
| WO | WO 2014/152795 A2 | 9/2014 |
| WO | WO 2014/169264 A1 | 10/2014 |
| WO | WO 2014/201245 A1 | 12/2014 |
| WO | WO 2015/153975 A1 | 10/2015 |
| WO | WO 2015/187966 A1 | 12/2015 |
| WO | WO 2015/195628 A2 | 12/2015 |
| WO | WO 2016/004168 A1 | 1/2016 |
| WO | WO 2016/115320 A1 | 7/2016 |
| WO | WO 2016/149323 A1 | 9/2016 |
| WO | WO 2017/011662 A1 | 1/2017 |
| WO | WO 2017/035278 A1 | 3/2017 |
| WO | WO 2017/193087 A1 | 11/2017 |
| WO | WO 2018/201090 A1 | 11/2018 |
| WO | WO 2019/168558 A1 | 9/2019 |
| WO | WO 2019/169203 A1 | 9/2019 |

OTHER PUBLICATIONS

International Search Report and Written Opinion dated Nov. 18, 2015 for PCT/US2015/054288.

International Search Report and Written Opinion dated May 16, 2016 for PCT/US2016/013365.

International Search Report and Written Opinion dated Aug. 3, 2016 for PCT/US2016/018395.

International Search Report and Written Opinion dated May 23, 2016 for PCT/US2016/022579.

Akhter et al., Gold nanoparticles in theranostic oncology: current state-of-the-art. Expert Opin Drug Deliv. Oct. 2012;9(10):1225-43. Epub Aug. 16, 2012.

Bae et al., Targeted drug delivery to tumors: myths, reality and possibility. J Control Release. Aug. 10, 2011;153(3):198-205. doi: 10.1016/j.jconrel.2011.06.001. Epub Jun. 6, 2011.

Banchelli, M. et al., "Phospholipid Membranes Decorated by Cholesterol-Based Oligonucleotides as Soft Hybrid Nanostructures," J. Phys. Chem., 2008, 112 (35), 10942-10952.

Banga et al., Liposomal spherical nucleic acids. J Am Chem Soc. Jul. 16, 2014;136(28):9866-9. doi: 10.1021/ja504845f. Epub Jul. 1, 2014.

Chen et al., Kinetics and thermodynamics of DNA hybridization on gold nanoparticles. Nucleic Acids Res. Jun. 2009;37(11):3756-65. doi: 10.1093/nar/gkp230. Epub Apr. 20, 2009.

Cheng et al., Interdigitated phospholipid/alkanethiol bilayers assembled on APTMS-supported gold colloid electrodes. Electroanalysis. 2004;16(1-2):127-31. doi:10.1002/elan.200302929.

Chinnathambi et al., Binding mode of CpG Oligodeoxynucleotides to nanoparticles regulates bifurcated cytokine induction via Toll-like Receptor 9. Sci Reports. 2012;2:1-9.

Cho et al., Therapeutic nanoparticles for drug delivery in cancer. Clin Cancer Res. Mar. 1, 2008;14(5):1310-6. doi: 10.1158/1078-0432.CCR-07-1441.

Cutler et al., Polyvalent nucleic acid nanostructures. J Am Chem Soc. Jun. 22, 2011;133(24):9254-7. doi:10.1021/ja203375n. Epub Jun. 1, 2011.

Cutler et al., Polyvalent oligonucleotide iron oxide nanoparticle "click" conjugates. Nano Lett. Apr. 14, 2010;10(4):1477-80. doi:10.1021/nl100477m.

Cutler et al., Spherical nucleic acids. J Am Chem Soc. Jan. 25, 2012;134(3):1376-91. doi: 10.1021/ja209351u. Epub Jan. 9, 2012.

Daniel et al., Gold nanoparticles: assembly, supramolecular chemistry, quantum-size-related properties, and applications toward biology, catalysis, and nanotechnology. Chem Rev. Jan. 2004;104(1):293-346.

Dhar et al., Polyvalent oligonucleotide gold nanoparticle conjugates as delivery vehicles for platinum (IV) warheads. J Am Chem Soc. Oct. 21, 2009;131(41):14652-3. doi: 10.1021/ja907182.

Diebold et al., Nucleic acid agonists for Toll-like receptor 7 are defined by the presence of uridine ribonucleotides. Eur J Immunol. Dec. 2006;36(12):3256-67.

Elbakry, A. et al., "Layer-by-Layer Assembled Gold Nanoparticles for siRNA Delivery," Nano Lett., 2009, 9 (5), 2059-2064.

Ferrari, Cancer nanotechnology: opportunities and challenges. Nature Reviews Cancer. 2005;5:161-71.

Forsbach et al., Identification of RNA sequence motifs stimulating sequence-specific TLR8-dependent immune responses. J Immunol. Mar. 15, 2008;180(6):3729-38.

Giljohann et al., Gold nanoparticles for biology and medicine. Angew Chem Int Ed Engl. Apr. 26, 2010;49(19):3280-94. doi: 10.1002/anie.200904359.

Giljohann et al., Oligonucleotide loading determines cellular uptake of DNA-modified gold nanoparticles. Nano Lett. Dec. 2007;7(12):3818-21. Epub Nov. 13, 2007.

(56) References Cited

OTHER PUBLICATIONS

Godard, G. et al., "Antisense Effects of Cholesterol-Oligodeoxynucleotide Conjugates Associated with Poly(alkylcyanoacrylate) Nanoparticles," Eur. J. Biochem., 1995, 232 (2), 404-410.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Han et al., Drug and gene delivery using gold nanoparticles. NanoBiotechnology. Mar. 2007;3(1):40-5.
He et al., Phospholipid-stabilized Au-nanoparticles. Biomacromolecules. May-Jun. 2005;6(3):1224-5.
Heil et al., Species-specific recognition of single-stranded RNA via toll-like receptor 7 and 8. Science. Mar. 5, 2004;303(5663):1526-9. Epub Feb. 19, 2004.
Hurst, S. et al., "Maximizing DNA Loading on a Range of Gold Nanoparticle Sizes," Anal. Chem., 2006, 78 (24), 8313-8318.
Kanzler et al., Therapeutic targeting of innate immunity with Toll-like receptor agonists and antagonists. Nat Med. May 2007;13(5):552-9.
Kerkmann et al., Immunostimulatory properties of CpG-oligonucleotides are enhanced by the use of protamine nanoparticles. Oligonucleotides. 2006 Winter;16(4):313-22.
Krieg. Antiinfective applications of toll-like receptor 9 agonists. Proc Am Thorac Soc. Jul. 2007;4(3):289-94.
Leander, D., "Mixed-Monolayer Gold Nanoparticles for Cancer Therapeutics," Nanoscape, 2010, 7 (1), 11-14.
Li et al., Combination delivery of antigens and CpG by lanthanides-based core-shell nanoparticles for enhanced immune response and dual-mode imaging. Adv Healthc Mater. Oct. 2013;2(10):1309-13. doi:10.1002/adhm.201200364. Epub Mar. 25, 2013.
Lin et al., Gold nanoparticle delivery of modified CpG stimulates macrophages and inhibits tumor growth for enhanced immunotherapy. PLoS One. May 15, 2013;8(5):e63550. doi: 10.1371/journal.pone.0063550. Print 2013.
Liu et al., Membrane anchored immunostimulatory oligonucleotides for in vivo cell modification and localized immunotherapy. Angew Chem Int Ed Engl. Jul. 25, 2011;50(31):7052-5. doi: 10.1002/anie.201101266. Epub Jun. 17, 2011.
Luthi et al., Nanotechnology for synthetic high-density lipoproteins. Trens Mol Med. Dec. 2010;16(12):553-60. doi: 10.1016/j.molmed.2010.10.006. Epub Nov. 17, 2010.
Luthi et al., Tailoring of biomimetic high-density lipoprotein nanostructures changes cholesterol binding and efflux. ACS Nano. Jan. 24, 2012;6(1):276-85. doi: 10.1021/nn2035457. Epub Dec. 1, 2011.
Lytton-Jean et al., A thermodynamic investigation into the binding properties of DNA functionalized gold nanoparticle probes and molecular fluorophore probes. J Am Chem Soc. Sep. 21, 2005;127(37):12754-5.
Massich et al., Regulating immune response using polyvalent nucleic acid-gold nanoparticle conjugates. Mol Pharm. Nov.-Dec. 2009;6(6):1934-40.
McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.
Mirza et al., Preparation and characterization of doxorubicin functionalized gold nanoparticles. Eur J Med Chem. May 2011;46(5):1857-60. doi: 10.1016/j.ejmech.2011.02.048. Epub Feb. 24, 2011.
Niemeyer, C. et al., "Bifunctional DNA-Gold Nanoparticle Conjugates as Building Blocks for the Self-Assembly of Cross-Linked Particle Layers," Biochemical and Biophysical Research Communications, 2003, 311 (4), 995-999.
Nikolov et al., Bias-dependent admittance in hybrid bilayer membranes. Langmuir. Aug. 15, 2006;22(17):7156-8.
Patel et al., Peptide antisense nanoparticles. Proc Natl Acad Sci U S A. Nov. 11, 2008;105(45):17222-6. doi:10.1073/pnas.0801609105.
Paul, New Way to Kill Lymphoma without Chemotherapy uses Golden Nanoparticles. Feinberg School of Medicine: Northwestern University. Jan. 22, 2013. 4 pages. www.feinberg.northwestern.edu/news/2013/01/lymphoma_nanoparticales.html.
Rana et al., Monolayer coated gold nanoparticles for delivery applications. Adv Drug Deliv Rev. Feb. 2012;64(2):200-16. doi: 10.1016/j.addr.2011.08.006. Epub Sep. 6, 2011.
Rosi et al., Oligonucleotide-modified gold nanoparticles for intracellular gene regulation. Science. May 19, 2006;312(5776):1027-30.
Schmidt, Clinical setbacks for toll-like receptor 9 agonists in cancer. Nat Biotechnol. Aug. 2007;25(8):825-6. Epub Aug. 2, 2007.
Seferos et al., Polyvalent DNA nanoparticle conjugates stabilize nucleic acids. Nano Lett. Jan. 2009;9(1):308-11.
Sigalov, A novel ligand-independent peptide inhibitor of TREM-1 suppresses tumor growth in human lung cancer xenografts and prolongs survival of mice with lipopolysaccharide-induced septic shock. Int Immunopharmacol. Jul. 2014;21(1):208-19. doi: 10.1016/j.intimp.2014.05.001. Epub May 14, 2014.
Sokolova et al., The use of calcium phosphate nanoparticles encapsulating Toll-like receptor ligands and the antigen hemagglutinin to induce dendritic cell maturation and T cell activation. Biomaterials. Jul. 2010;31(21):5627-33. doi: 10.1016/j.biomaterials.2010.03.067. Epub Apr. 24, 2010.
Sood, 'Good cholesterol' nanoparticles seek and destroy cancer cells. The University of Texas MD Anderson Cancer Center. 2011. Downloaded Apr. 4, 2011. http://healthorbit.ca/newsdetail.asp?opt=1&nitid=164032911.
Thaxton, C.S. et al., "Templated Spherical High Density Lipoprotein Nanoparticles," J. Am. Chem. Soc., 2009, 131 (4), 1384-1385.
Tincer et al., Immunostimulatory activity of polysaccharide-poly(I:C) nanoparticles. Biomaterials. Jun. 2011;32(18):4275-82. doi: 10.1016/j.biomaterials.2011.01.028.Epub Apr. 2, 2011.
Tiwari et al., Functionalized gold nanoparticles and their biomedical applications. Nanomaterials. 2011;1:31-63. doi: 10.3390/nano1010031.
Wang et al., Doxorubicin-tethered responsive gold nanoparticles facilitate intracellular drug delivery for overcoming multidrug resistance in cancer cells. ACS Nano. May 24, 2011;5(5):3679-92. doi: 10.1021/nn200007z. Epub Apr. 12, 2011.
Wei et al., Polyvalent immunostimulatory nanoagents with self-assembled CpG oligonucleotide-conjugated gold nanoparticles. Angew Chem Int Ed Engl. Jan. 27, 2012;51(5):1202-6. doi:10.1002/anie.201105187. Epub Dec. 21, 2011.
West et al., Recognition and signaling by toll-like receptors. Annu Rev Cell Dev Biol. 2006;22:409-37.
Wilson et al., pH-Responsive nanoparticle vaccines for dual-delivery of antigens and immunostimulatory oligonucleotides. ACS Nano. May 28, 2013;7(5):3912-25. doi: 10.1021/nn305466z. Epub Apr. 30, 2013.
Yang et al., Biomimetic, synthetic HDL nanostructures for lymphoma. Proc Natl Acad Sci U S A. Feb. 12, 2013;110(7):2511-6. doi: 10.1073/pnas.1213657110. Epub Jan. 23, 2013.
Zhang et al., A general approach to DNA-programmable atom equivalents. Nat Mater. Aug. 2013;12(8):741-6. doi: 10.1038/nmat3647. Epub May 19, 2013.
Zheng et al., A spherical nucleic acid platform based on self-assembled DNA biopolymer for high-performance cancer therapy. ACS Nano. Aug. 27, 2013;7(8):6545-54. doi: n402344v. Epub Jul. 23, 2013.
Agbasi-Porter et al., Transcription inhibition using oligonucleotide-modified gold nanoparticles, Bioconjugate Chem., 17(5):1178-83 (2006).
Akbarzadeh et al., Liposome: classification, preparation, and applications, Nanoscale Res Lett. Feb. 22, 2013;8(1):102. doi: 10.1186/1556-276X-8-102.
Alemdaroglu et al., DNA Block Copolymer Micelles—a Combinatorial Tool for Cancer Nanotechnology. Advanced Materials. Mar. 2008;20(5)899-902. https://doi.org/10.1002/adma.200700866I.
Andrews et al., Conjugation of Lipid and CpG-Containing Oligonucleotide Yields an Efficient Method for Liposome Incorporation. Bioconjuqate Chem. 2011;22:1279-1286.
Bode et al. CpG DNA as a vaccine adjuvant. Expert Rev Vaccines. Apr. 2011;10(4):499-511. doi: 10.1586/erv.10.174.

(56) References Cited

OTHER PUBLICATIONS

Briley et al., Chapter 1: Biochemistry and Biomedical Applications of Spherical Nucleic Acids (SNAs). In Nanomaterials for Biomedicine; American Chemical Society. 2012;1119:1-20.

Bunge et al., Lipophilic oligonucleotides spontaneously insert into lipid membranes, bind complementary DNA strands, and sequester into lipid-disordered domains. Langmuir. Apr. 10, 2007;23(8):4455-64. Epub 2007 ar 17.

Burgess, Liposome preparation—Avanti® Polar Lipids. Sigma-Aldrich. 1998. 3 pages.

Cao et al., Reversible Cell-Specific Drug Delivery with Aptamer-Functionalized Liposomes, Angew. Chem. Int. Ed. 2009;48:6494-8.

Choi et al., Mechanism for the endocytosis of spherical nucleic acid nanoparticle conjugates, Proc. Natl. Acad. Sci. U.S.A. 2013;110:7625-7630.

Combadiere et al., Particle-based vaccines for transcutaneous vaccination. Comp Immunol Microbiol Infect Dis. Mar. 2008;31(2-3):293-315. Epub Oct. 30, 2007. Review.

Cui et al., Topical immunization using nanoengineered genetic vaccines. J Control Release. May 17, 2002;81(1-2):173-84.

Dua et al., Liposome: Methods of Preparation and Applications. (IJPSR (2012) 3(2):14-20).

Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.

Englisch et al., "Chemically Modified Oligonucleotides as Probes and Inhibitors" Angewandte Chemie, International Edition, 30:613-629 (1991).

Farokhzad et al., Nanomedicine: developing smarter therapeutic and diagnostic modalities, Drug Delivery Rev., 58:1456 (2006).

Fishwick et al., Phytochemistry vol. 16, Issue 10, 1977, pp. 1507-1510.

Giljohann et al., Gene regulation with polyvalent siRNA-nanoparticle conjugates. J Am Chem Soc. Feb. 18, 2009;131(6):2072-3. doi: 10.1021/ja808719p.

Guiducci et al., Properties regulating the nature of the plasmacytoid dendritic cell response to Toll-like receptor 9 activation. J Exp Med. Aug. 7, 2006;203(8):1999-2008. Epub Jul. 24, 2006.

Gunnarsson et al., Liposome-Based Chemical barcodes for Single Molecule DNA Detection Using Imaging Mass Spectrometry, Nano. Lett. 2010;10:732-7.

Hope et al., Production of large unilamellar vesicles by a rapid extrusion procedure: characterization of size distribution, trapped volume and ability to maintain a membrane potential. Biochim Biophys Acta. Jan. 10, 1985;812(1):55-65.

Jahn et al., Microfluidic directed formation of liposomes of controlled size. Langmuir. May 22, 2007;23(11):6289-93. ; Epub Apr. 24, 2007.

Jakobsen et al., Assembly of liposomes controlled by triple helix formation, Bioconjugate Chem. 2013;24:1485-95.

Kandimalla et al., Conjugation of Ligands at the 5'-End of CpG DNA Affects Immunostimulatory Activity. Bioconjugate Chemistry 2002 13 (5), 966-974. DOI: 10.1021/bc0200374.

Kelly et al., Targeted Liposomal Drug Delivery to Monocytes and Macrophages. J Drug Delivery. 2011;1-11.

Kim et al., Effect of bovine serum albumin on the stability of methotrexate-encapsulated liposomes, Arch. Pharmacal Res. 1991;14:336.

Krug et al. Identification of CpG oligonucleotide sequences with high induction of IFN-alpha/beta in plasmacytoid dendritic cells. Eur J Immunol. Jul. 2001;31(7):2154-63.

Langer, New methods of drug delivery. Science. Sep. 28, 1990;249(4976):1527-33.

Laouini et al., iPreparation, Characterization and Applications of Liposomes: State of the Art. J Colloid Sci and Biotechnol. 2012;1:147-68.

Lee et al., Imageable antigen-presenting gold nanoparticle vaccines for effective cancer immunotherapy in vivo. Angew Chem. 2012;124(35):8930-5.

Lee et al., Imageable antigen-presenting gold nanoparticle vaccines for effective cancer immunotherapy in vivo. Angew Chem Int Ed Engl. Aug. 27, 2012;51(35):8800-5. doi:10.1002/anie.201203193.

Lesieur et al., Size analysis and stability study of lipid vesicles by high-performance gel exclusion chromatography, turbidity, and dynamic light scattering. Anal Biochem. Feb. 1, 1991;192(2):334-43.

Li et al., Reversible and Chemically Programmable Micelle Assembly with DNA Block-Copolymer Amphiphiles, Nano Lett. 2004;4:1055.

Liu et al., DNA-based micelles: synthesis, micellar properties and size-dependent cell permeability, Chemistry. 2010;16:3791-7.

Lohcharoenkal et al., Protein Nanoparticles as Drug Delivery Carriers for Cancer Therapy. BioMed Research International. 2014; Article ID 180549. 12 pages. http://dx.doi.org/10.1155/2014/180549.

Marshall et al., Novel chimeric immunomodulatory compounds containing short CpG oligodeoxyribonucleotides have differential activities in human cells. Nucleic Acids Res. Sep. 1, 2003;31(17):5122-33.

Martin et al.,Ein neur Zugang zu 2'-O-alkylribonucleosiden and Eigenschaften deren oligonucleotide Hely, Chim. Acta, 78:486-504 (1995).

Mehta et al., Topical and transdermal delivery: What a pharmacist needs to know. InetCE. Jul. 2004:1-10.

Ming et al., Albumin-based nanoconjugates for targeted delivery of ; therapeutic oligonucleotides. Biomaterials. Oct. 2013;34(32):7939-49. doi: 10.1016/j.biomaterials.2013.06.066. Epub Jul. 19, 2013.

Mirkin et al., A DNA-based method for rationally assembling nanoparticles into macroscopic materials, Nature, 382:607-9 (1996).

Mui et al., Immune stimulation by a CpG-containing oligodeoxynucleotide is enhanced when encapsulated and delivered in lipid particles. J Pharmacol Exp Ther. Sep. 2001;298(3):1185-92.

Munde et al., Induced fit conformational changes of a "reversed amidine" heterocycle: optimized interactions in a DNA minor groove complex. J Am Chem Soc. May 2, 2007;129(17):5688-98. Epub Apr. 11, 2007.

Patel et al., Scavenger receptors mediate cellular uptake of polyvalent oligonucleotide-functionalized gold nanoparticles, Bioconj. Chem., 21:2250 (2010).

Patil et al., Temozolomide delivery to tumor cells by a multifunctional nano vehicle based on poly(β-L-malic acid). Pharm Res. Nov. 2010;27(11):2317-29. doi: 10.1007/s11095-010-0091-0. Epub Apr. 13, 2010.

Pfeiffer et al., Bivalent Cholesterol-Based Coupling of Oligonucleotides to Lipid Membrane Assemblies. J. Am. Chem. Soc. 2004;126:10224-10225.

Pfeiffer et al., Quantification of oligonucleotide modifications of small unilamellar lipid vesicles. Anal. Chem. 2006;78:7493-8.

Ramos-Casals et al., Autoimmune diseases induced by TNF-targeted therapies: analysis of 233 cases. Medicine (Baltimore). Jul. 2007;86(4):242-51.

Rosi et al., Nanostructures in biodiagnostics, Chem. Rev., 105:1547 (2005).

Schieren et al., Comparison of large unilamellar vesicles prepared by a petroleum ether vaporization method with multilamellar vesicles: ESR, diffusion and entrapment analyses. Biochim Biophys Acta. Aug. 3, 1978;542(1):137-53.

Schwab et al., An approach for new anticancer drugs: Oncogene-targered antisense DNA. Ann Oncol. 1994;5(Supp14):S55-8.

Senior et al., Stability of small unilamellar liposomes in serum and clearance from the circulation: the effect of the phospholipid and cholesterol components, Life Sci. 30:2123 (1982).

Shukla et al., Development of streptavidin-based ; nanocomplex for siRNA delivery. Mol Pharm. Dec. 2, 2013;10(12):4534-45. doi:; 10.1021/mp400355q. Epub Oct. 25, 2013.

Shukoor et al., CpG-DNA loaded multifunctional MnO nanoshuttles for TLR9-specific cellular cargo delivery, selective immune-activation and MRI. J. Mater. Chem., 2012,22, 8826-8834.

Stengel et al., Determinants for Membrane Fusion Induced by Cholesterol-Modified DNA Zippers, J. Phys. Chem. B., 112:8264-74 (2008).

Stengel et al., DNA-Induced Programmable Fusion of Phospholipid Vesicles, J. Am. Chem. Soc., 129:9584-5 (2007).

(56) References Cited

OTHER PUBLICATIONS

Sulkowski et al., The influence of temperature, cholesterol content and pH on liposome stability, J. Mol. Struct., 744-747: 737 (2005).
Tai et al., Heat-activated sustaining nitric oxide release from zwitterionic diazeniumdiolate loaded in thermo-sensitive liposomes. Nitric Oxide. Aug. 1, 2010;23(1):60-4. doi: 10.1016/j.niox.2010. 04.003. Epub Apr. 22, 2010.
Versluis et al., In situ modification of plain liposomes with lipidated coiled coil forming peptides induces membrane fusion, J. Am. Chem. Soc.. 135:8057 (2013).
Vorobjev et al., Nuclease resistance and RNase H sensitivity of oligonucleotides bridged by oligomethylenediol and oligoethylene glycol linkers. Antisense Nucleic Acid Drug Dev. Apr. 2001;11(2):77-85.
Wang, Synthetic CpG ODNs activate immune cells through the Toll-like receptor (TLR) pathway. Integrated DNA Technologies. Apr. 11, 2017. 3 pages.
Whitehead et al., Knocking down barriers: advances in siRNA delivery, Nat. Rev. Drug. Discov., 8:129 (2009).
Willis et al., Liposome-Anchored Vascular Endothelial Growth Factor Aptamers, Biocon. Chem., 9:573-82 (1998).
Young et al., Hollow spherical nucleic acids for intracellular gene regulation based upon biocompatible silica shells, Nano Lett., 12:3867 (2012).
Zhang et al., Antibody-linked spherical nucleic acids for cellular targeting, J. Am. Chem. Soc., 134:16488-91 (2012).
Zhang et al., Structure-activity relationships of cationic shell-crosslinked knedel-like nanoparticles: shell composition and transfection efficiency/cytotoxicity, Biomaterials, 31:1805 (2010).
Zheng et al., Sterically controlled docking of gold nanoparticles on ferritin; surface by DNA hybridization. Nanotechnology. Jul. 8, 2011;22(27):275312. doi:; 10.1088/0957-4484/22/27/275312. Epub May 26, 2011.
Ali et al., Vaccines Combined with Immune Checkpoint Antibodies Promote Cytotoxic T-cell Activity and Tumor Eradication. Cancer Immunol Res. Feb. 2016;4(2):95-100. doi: 10.1158/2326-6066.CIR-14-0126. Epub Dec. 15, 2015.
Asthana et al., Mannosylated chitosan nanoparticles for delivery of antisense oligonucleotides for macrophage targeting. Biomed Res Int. 2014;2014:526391. doi: 10.1155/2014/526391. Epub Jun. 26, 2014.
Aurasense Therapeutics, NIH grant. Topically-delivered Target Gene Suppression of Immune Activation in Psoriasis. David Giljohann. Accessed on Aug. 2, 2017 from http://grantome.com/grant/NIH/R41-AR066438-01. Accessible online on Feb. 21, 2016 as verified through Wayback Machine.
Boudreault et al., Nanoscale tools to selectively destroy cancer cells. Chem Commun. May 14, 2008;(18):2118-20. doi: 10.1039/b800528a. Epub Apr. 7, 2008.
Dave et al., Programmable assembly of DNA-functionalized liposomes by DNA. ACS Nano. Feb. 22, 2011;5(2):1304-12. doi: 10.1021/nn1030093. Epub Jan. 4, 2011.
Gissot et al., Nucleoside, nucleotide and oligonucleotide based amphiphiles: a successful marriage of nucleic acids with lipids. Org. Biomol. Chem. 2008;6:1324-33.
Gryaznov, Oligonucleotide n3'-->p5' phosphoramidates and thiophoshoramidates as potential therapeutic agents. Chem Biodivers. Mar. 2010;7(3):477-93. doi: 10.1002/cbdv.200900187. Review.
Hartmann et al., Delineation of a CpG phosphorothioate oligodeoxynucleotide for activating primate immune responses in vitro and in vivo. J Immunol. Feb. 1, 2000;164(3):1617-24.
Houot et al., T-cell modulation combined with intratumoral CpG cures lymphoma in a mouse model without the need for chemotherapy. Blood. Apr. 9, 2009;113(15):3546-52. doi: 10.1182/blood-2008-07-170274. Epub Oct. 21, 2008.
Kandimalla et al., Secondary structures in CpG oligonucleotides affect immunostimulatory activity. Biochem Biophys Res Commun. Jul. 11, 2003;306(4):948-53.
Khmelinskaia et al., Effect of anchor positioning on binding and diffusion of elongated 3D DNA nanostructures on lipid membranes. J. Phys. D: Appl. Phys. Apr. 13, 2016;49(19):194001.
Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.
Kwoh et al., Stabilization of poly-L-lysine/DNA polyplexes for in vivo gene delivery to the liver. Biochim Biophys Acta. Feb. 16, 1999;1444(2):171-90.
Lennox et al., Characterization of modified antisense oligonucleotides in Xenopus laevis embryos. Oligonucleotides. 2006 Spring;16(1):26-42.
Liu et al., Structure-based programming of lymph-node targeting in molecular vaccines. Nature. Mar. 27, 2014;507(7493):519-22. doi: 10.1038/nature12978.
Mangsbo et al., Enhanced tumor eradication by combining CTLA-4 or PD-1 blockade with CpG therapy. J Immunother. Apr. 2010;33(3):225-35. doi: 10.1097/CJI.0b013e3181c01fcb.
McKay et al., Characterization of a potent and specific class of antisense oligonucleotide inhibitor of human protein kinase C-alpha expression. J Biol Chem. Jan. 15, 1999;274(3):1715-22.
Monia et al., Nuclease resistance and antisense activity of modified oligonucleotides targeted to Ha-ras. J Biol Chem. Jun. 14, 1996;271(24):14533-40.
Patwa et al., Hybrid lipid oligonucleotide conjugates: synthesis, self-assemblies and biomedical applications. Chem Soc Rev. 2011;40:5844-54.
Pokholenko et al., Lipid oligonucleotide conjugates as responsive nanomaterials for drug delivery. J of Materials Chemistry B. 2013;5329-34.
Polizzi et al., Water-soluble nitric oxide-releasing gold nanoparticles. Langmuir. Apr. 24, 2007;23(9):4938-43. Epub Mar. 22, 2007.
Rothrock et al., Synthesis of nitric oxide-releasing gold nanoparticles. J Am Chem Soc. Jul. 6, 2005;127(26):9362-3.
Rush et al., Intracellular mRNA regulation with self-assembled locked nucleic acid polymer nanoparticles. J Am Chem Soc. May 28, 2014;136(21):7615-8. doi: 10.1021/ja503598z. Epub May 14, 2014.
Saraiva et al., Nanocarriers for nitric oxide delivery. J Drug Deliv. 2011;2011:936438. doi: 10.1155/2011/936438. Epub Aug. 22, 2011.
Sita et al., Dual bioluminescence and near-infrared fluorescence monitoring to evaluate spherical nucleic acid nanoconjugate activity in vivo. Proc Natl Acad Sci U S A. Apr. 18, 2017;114(16):4129-4134. doi: 10.1073/pnas.1702736114. Epub Apr. 3, 2017.
Switaj et al., CpG immunostimulatory oligodeoxynucleotide 1826 enhances antitumor effect of interleukin 12 gene-modified tumor vaccine in a melanoma model in mice. Clin Cancer Res. Jun. 15, 2004;10(12 Pt 1):4165-75.
United States Securities and Exchange Commission Form 8-K Current Report, Date of Report (Date of earliest event reported): Sep. 26, 2017; Exicure, Inc. Dated: Oct. 2, 2017 by David Giljohann Accessed from the internet (Oct. 11, 2018) at https://www.sec.gov/Archives/edgar/data/1698530/000119312517301064/d461080d8k. htm.
Wilton et al. Antisense oligonucleotide-induced exon skipping across the human dystrophin gene transcript. Mol Ther. Jul. 2007;15(7):1288-96. Epub Feb. 6, 2007.
Xiao et al., Mannosylated bioreducible nanoparticle-mediated macrophage-specific TNF-60 RNA interference for IBD therapy. Biomaterials. Oct. 2013;34(30):7471-82. doi: 10.1016/j.biomaterials.2013.06. 008. Epub Jun. 29, 2013.
Yin et al., Supramolecular self-assembled nanoparticles mediate oral delivery of therapeutic TNF-60 siRNA against systemic inflammation. Angew Chem Int Ed Engl. May 27, 2013;52(22):5757-61. doi: 10.1002/anie.201209991. Epub Apr. 22, 2013.
Zhang et al., Informational liposomes: Complexes derived from cholesteryl-conjugated oligonucleotides and liposomes. Tetrahedron Letters. 1996. 37(35):6243-6.
Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas. 1118425109. Epub Jul. 6, 2012.

(56) References Cited

OTHER PUBLICATIONS

U.S. Appl. No. 15/980,428, filed May 15, 2018, Radovic-Moreno et al.
U.S. Appl. No. 15/301,467, filed Oct. 3, 2016, Gryaznov.
U.S. Appl. No. 16/569,007, filed Sep. 12, 2019, Radovic-Moreno et al.
U.S. Appl. No. 16/248,912, filed Jan. 16, 2019, Mader et al.
U.S. Appl. No. 15/543,728, filed Jul. 14, 2017, Daniel et al.
U.S. Appl. No. 16/883,756, filed May 26, 2020, Daniel et al.
U.S. Appl. No. 15/552,115, filed Aug. 18, 2017, Gryaznov et al.
U.S. Appl. No. 15/744,586, filed Jan. 12, 2018, Giljohann.
U.S. Appl. No. 16/074,504, filed Aug. 1, 2018, Kang et al.
U.S. Appl. No. 16/095,134, filed Oct. 19, 2018, Patel et al.
U.S. Appl. No. 16/099,404, filed Nov. 6, 2018, Anderson et al.
U.S. Appl. No. 16/099,409, filed Nov. 6, 2018, Nallagatla et al.
U.S. Appl. No. 16/099,385, filed Nov. 6, 2018, Kang et al.
U.S. Appl. No. 16/608,685, filed Oct. 25, 2019, Kang et al.
U.S. Appl. No. 16/242,704, filed Jan. 8, 2019, Mirkin et al.
[No Author Listed] Spacer 18 (Hexathylene glycol) Oligonucleotide Modification. BioSynthesis. Last accessed Nov. 7, 2019 via https://www.biosyn.com/oligonucleotideproduct/spacer-18-heg-oligonucleotide-modification.aspx. 3 pages.
[No Author Listed] Spacer 18 (hexathyleneglycol) GeneLink. Last accessed Nov. 7, 2019 via http://genelink.com/newsite/products/mod_detail.asp?modid=19. 2 pages.
Abou-alfa et al., Randomized phase III study of exatecan and gemcitabine compared with gemcitabine alone in untreated advanced pancreatic cancer, J. Clin. Oneal. 2006; 24(27):4441-7.
Agasti et al., Photoregulated release of caged anticancer drugs from gold nanoparticles, J. Am. Chem. Soc. 2009; 131(16):5728-9.
Ahmadi et al., Shape-Controlled Synthesis of Colloidal Platinum Nanoparticles. Science. 1996; 272(5270): 1924-1926.
Altieri, Survivin, versatile modulation of cell division and apoptosis in cancer. Oncogene 2003; 22: 8581-9.
Angelini et al., Reversal of P-glycoprotein-mediated multidrug resistance in human sarcoma MES-SA/Dx-5 cells by nonsteroidal anti-inflammatory drugs. Oneal. Rep. 2008;20(4):731-5.
Anton et al., Design and production of nanoparticles formulated from nano-emulsion templates—a review. J. Control Release. 2008; 128(3):185-99.
Baker et al., Dendrimer-mediated cell transfection in vitro. Meth. Malec. Biol. 2004;245: 67-81.
Balasubramanian et al., Biodistribution of gold nanoparticles and gene expression changes in the liver and spleen after intravenous administration in rats. Biomaterials. 2010;31(8):2034-42.
Bardeesy et al., Pancreatic cancer biology and genetics, Nat. Rev. Cancer. 2002;2(12):897-909.
Berton et al., Highly loaded nanoparticulate carrier using an hydrophobic antisense oligonucleotide complex. Eur. J. Pharma. Sci. 1999;9:163-70.
Bisht et al., Polymeric nanoparticle-encapsulated curcumin ("nanocurcumin"): a novel strategy for human cancer therapy. J. Nanobiotechnology. 2007;5:3. 18 pages.
Bitounis et al., Optimizing Druggability through Liposomal Formulations: New Approaches to an Old Concept. ISRN Pharm. 2012;2012:738432. doi: 10.5402/2012/738432. Epub Feb. 9, 2012.
Bonoiu et al., Nanotechnology approach for drug addiction therapy: gene ; silencing using delivery of gold nanorod-siRNA nanoplex in dopaminergic neurons. Proc Natl Acad Sci U S A. Apr. 7, 2009;106(14):5546-50. doi:; 10.1073/pnas.0901715106. Epub Mar. 23, 2009.
Brodin et al., DNA-mediated engineering of multicomponent; enzyme crystals. Proc Natl Acad Sci U S A. Apr. 14, 2015;112(15):4564-9. doi:; 10.1073/pnas.1503533112. Epub Mar. 23, 2015.
Brown et al., Surface treatment of the hydrophobic drug danazol to improve drug dissolution. Int. J. Pharmaceutics. 1998;165:227-37.
Brus, "Quantum Crystallites and Nonlinear Optics," Appl. Phys. A53:465-474 (1991).

Capaccioli et al., Cationic lipids improve antisense oligonucleotide uptake and prevent degradation in cultured cells and inhuman serum. Biochem. Biophys. Res. Commun. 1993;197(2): 818-25.
Cha et al., Hepatocellular carcinoma: current management. Curr. Probl. Surg. 2010;47(1):10-67.
Chari et al., Immunoconjugates containing novel maytansinoids: promising anticancer drugs. Cancer Res. 1992;52(1):127-31.
Charreyre et al., Fluorescence energy transfer study of the conformation of oligonucleotides covalently bound to polystyrene latex particles. Langmuir. 1997;13: 3103-10.
Chavany, et al., Adsorption of oligonucleotides onto polyisohexylcyanoacrylate nanoparticles protects them against nucleases and increases their cellular uptake. Pharma. Res. 1994;11(9):1370-8.
Chen et al., Ionic strength-dependent persistence lengths of single-stranded RNA and DNA. Proc Natl Acad Sci USA. 2012;109:799-804.
Chen et al., MDR1 activation is the predominant resistance mechanism selected by vinblastine in MES-SA cells. Br. J. Cancer. 2000;83(7):892-8.
Chen et al., Nanoparticle-aptamer: an effective growth inhibitor for human cancer cells. IMECE 2009-11966. Jul. 8, 2010;271-2. https://doi.org/10.1115/IMECE2009-11966. 2 pgs.
Cheng et al., Synthesis of linear, beta-cyclodextrin-based polymers and their camptothecin conjugates. Bioconjug Chem. 2003;14:1007-1017.
Cheng et al., Tandem synthesis of core-shell brush copolymers and their transformation to peripherally cross-linked and hollowed nanostructures. J. Am. Chem. Soc. 2006;128(21):6808-9.
Cheung et al., Akt3 and mutant V600E B-Raf cooperate to promote early melanoma development. Cancer Res. 2008;68:3429-39.
Chithrani et al., Determining the size and shape dependence of gold nanoparticle uptake into mammalian cells. Nano Lett. 2006;6(4):662-8.
Chithrani et al., Elucidating the mechanism of cellular uptake and removal of protein-coated gold nanoparticles of different sizes and shapes. Nano Lett. 2007;7: 1542-50.
Cho et al., Immunostimulatory DNA-based vaccines induce cytotoxic lymphocyte activity by a.
Chompoosor et al., Charge dependence of ligand release and monolayer stability of gold nanoparticles by biogenic thiols. Bioconjugate Chem. 2008;19:1342-5.
Chu et al., Effects of photoactivated 5-aminolevulinic acid hexyl ester on MDR1 over-expressing human uterine sarcoma cells. Toxicol. Lett. 2008;181(1):7-12.
Cloud et al., Polyether tethered oligonucleotide probes. J. Am. Chem. Soc. 1991;113(16): 6324-6.
Concise Encyclopedia of Polymer Science and Engineering, "Polynucleotides," J. I. Kroschwitz Ed., John Wiley & Sons, pp. 858-859 (1990).
Connor et al., Gold nanoparticles are taken up by human cells but do not cause acute cytotoxicity. Small. 2005;1(3):325-7.
Crawford et al., A novel B-RAF inhibitor blocks interleukin-8 (IL-8) synthesis in human melanoma xenografts, revealing IL-8 as a potential pharmacodynamic biomarker. Mol. Cancer Ther. 2008;7:492-9.
Dankort et al., A new mouse model to explore the initiation, progression, and therapy of BRAFV600E-induced lung tumors. Genes Dev. 2007;21: 379-84.
Dankort et al., Braf(V600E) cooperates with Pten loss to induce metastatic melanoma. Nat Genet. 2009;41: 544-52.
Davies et al., A novel AKT3 mutation in melanoma tumours and cell lines. Br. J. Cancer. 2008;99: 1265-8.
De Mesmaeker et al., Backbone modifications in oligonucleotides and peptide nucleic acid systems, Curr. Opin. in Struct. Biol., 5: 343-55 (1995).
Deutsch et al., Synthesis of congeners and prodrugs. 3. Water-soluble prodrugs of taxol with potent antitumor activity. J. Med. Chem. 1989;32(4):788-92.
Dhar et al., Targeted single wall carbon nanotube mediated Pt(IV) prodrug delivery using folate as a homing device. J. Am. Chem. Soc. 2008;130(34): 11467-76.

(56) References Cited

OTHER PUBLICATIONS

Dhomen et al., BRAF signaling and targeted therapies in melanoma. Hematol. Oneal. Clin. North Am. 2009;23: 529-45, ix.
Dulkeith et al., Gold nanoparticles quench fluorescence by phase induced radiative rate suppression. Nano Lett. 2005;5: 585-9.
Durand et al., Circular dichroism studies of an oligodeoxyribonucleotide containing a hairpin loop made of a hexaethylene glycol chain: conformation and stability. Nucl. Acids Res. 1990;18(21): 6353-9.
Eckstein, Oligonucleotides and Analogues, 1st Ed. (Oxford University Press, New York) (1991).
Elaissari et al., Effect of charge nature on the adsorption of single-stranded DNA fragments onto latex particles. J. Colloid Interface Sci. 1998;202: 251-60.
Elghanian et al., Selective colorimetric detection of polynucleotides based on the distance-dependent optical properties of gold nanoparticles. Science. 1997;277(5329):1078-81.
Endres et al., DNA-TiO2 nanoconjugates labeled with magnetic resonance contrast agents. J. Am. Chem. Soc. 2007;129(51):15760-1 and supplementary information.
Enustun, et al. "Coagulation of Colloidal Gold," J. Am. Chem. Soc. 85:3317-3328 (1963).
Ferentz et al., Disulfide-crosslinked oligonucleotides. J. Am. Chem. Soc. 1991;113(10): 4000-2.
Freier et al., The ups and downs of nucleic acid duplex stability: structure-stability studies on chemically-modified DNA:RNA duplexes, Nucleic Acids Research, 25:4429-43 (1997).
Fukuda et al., Effective transformation of unactivated alkynes into ketones or acetals by means of Au(III) catalyst. J. Org. Chem. 1991;56(11):3729-31.
Furstner et al., Catalytic carbophilic activation: catalysis by platinum and gold pi acids. Angew Chem Int Ed Engl.. 2007;46(19):3410-49.
Gavrieli et al., Identification of programmed cell death in situ via specific labeling of nuclear DNA fragmentation J. Cell Biol. 1992;119(3):493-501.
Ghosh et al., Gold nanoparticles in delivery applications. Adv. Drug Deliv. Rev. 2008;60(11):1307-15.
Gibson et al., Paclitaxel-functionalized gold nanoparticles. J. Am. Chem. Soc. 2007;129(37):11653-61.
Gigler et al., "DNA-controlled assembly of a NaTl lattice structure from gold and protein nanoparticles," Nat Mater 9(11): 918-922 (2010).
Goel et al., Melanocytic nevus-like hyperplasia and melanoma in transgenic BRAFV600E mice. Oncogene. 2009;28: 2289-98.
Hayashi, Ultrafine particles. J. Vac. Sci. Technol. 1987;5(4):1375-1384.
Hegner et al., Modified DNA immobilized on bioreactive self-assembled monolayer on gold for dynamic force microscopy imaging in aqueous buffer solution. J. Vac. Sci. Technol. B, 1996;14(2):1418-21.
Hellstrom et al., Epitaxial growth of DNA-assembled nanoparticle superlattices on patterned substrates. Nano Lett. 2013;13(12):6084-90. doi: 10.1021/nl4033654. Epub Nov. 20, 2013.
Henglein et al., "Absorption Spectrum and Some Chemical Reactions of Colloidal Platinum in Aaueous Solution," J. Phys. Chem., 99:14129-14136 (1995).
Henglein, "Mechanism of Reactions on Colloidal Microelectrodes and Size Quantization Effects," Topics in Curr. Chem., 143:113-180 (1988).
Hill et al., "Controlling the Lattice Parameters of Gold Nanoparticle FCC Crystals with Duplex DNA Linkers," Nano Lett 8(8): 2341-2344 (2008).
Hotz et al., VEGF antisense therapy inhibits tumor growth and improves survival in experimental pancreatic cancer. Surgery. Feb. 2005:137(2):192-9.
Hu et al., Hollow chitosan/poly(acrylic acid) nanospheres as drug carriers. Biomacromolecules. 2007;8(4):1069-76.
Hwu et al., Targeted Paclitaxel by conjugation to iron oxide and gold nanoparticles. J. Am. Chem. Soc.. 2009;131(1):66-8.
Jain et al., Synthesis of protein-loaded hydrogel particles in an aqueous two-phase system for coincident antigen and CpG oligonucleotide delivery to antigen-presenting cells. Biomacromolecules. Sep-Oct. 2005:6(5):2590-600.
Jaschke et al., Automated incorporation of polyethylene glycol in synthetic oligonucleotides. Tetrahedron Lett. 1993;34: 301-4.
Jen et al., A nonviral transfection approach in vitro: the design of a gold nanoparticle vector joint with microelectromechanical systems. Langmuir, 2004;20(4): 1369-74.
Jeong et al., Novel intracellular delivery system of antisense oligonucleotide by self-assembled hybrid micelles composed of DNA/PEG conjugate and cationic fusogenic peptide. Bioconjugate Chem. 2003;14: 473-9.
Jin et al., Radiosensitization of paclitaxel, etanidazole and paclitaxel+ etanidazole nanoparticles on hypoxic human tumor cells in vitro. Biomaterials. 2007;28(25):3724-30.
Kan et al., Distribution and effect of iodized poppyseed oil in the liver after hepatic artery embolization: experimental study in several animal species. Radiology. 1993;186(3):861-6.
Kan et al., Role of Kupffer cells in iodized oil embolization. Invest. Radiol. 1994;29(11 ):990-3.
Kasuya et al., Chapter 8—Bio-nanocapsule-liposome conjugates for in vivo pinpoint drug and gene delivery. Methods Enzymol. 2009;464:147-66.
Katz, "The reversible reaction of sodium thymonucleate and mercuric chloride," J. Am. Chem. Soc., 74:2238-2245 (1951).
Kim et al., Direct synthesis of polymer nanocapsules with a noncovalently tailorable surface. Angew. Chem. Int. Ed. Engl. 2007;46(19):3471-4.
Kim et al., Direct synthesis of polymer nanocapsules: self-assembly of polymer hollow spheres through irreversible covalent bond formation. J. Am. Chem. Soc. 2010;132(28):9908-19.
Kim et al., Facile, template-free synthesis of stimuli-responsive polymer nanocapsules for targeted drug delivery. Angew. Chem. Int. Ed. Engl. 2010;49(26):4405-8.
Kimura-Suda et al., Base-Dependent Competive Adsorption of Single-Stranded DNA on Gold. Journal of the American Chemical Society. 2003;125: 9014-9015.
Kolarova et al., Preparation of magnetic oligo (dT) particles. Biotechniques. 1996;20: 196-8.
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Krieg, Toll-like receptor 9 (TLR9) agonists in the treatment of cancer.; Oncogene. Jan. 7, 2008;27(2):161-7. doi: 10.1038/sj.onc. 1210911.
Landfester et al., From polymeric particles to multifunctional nanocapsules for biomedical applications using the miniemulsion process. J. Polymer Sci. Part A.2010; 48(3):493-515.
Lee et al., A DNA-Gold Nanoparticle-Based Colormetric Competition Assay for the Detection of Cysteine. Nano Letter. 2008;8(2):529-533.
Lee et al., All-in-one target-cell-specific magnetic nanoparticles for simultaneous molecular imaging and siRNA delivery. Angew Chem Int Ed Engl. 2009;48(23):4174-9. doi:10.1002/anie.200805998.
Lee et al., Chip-based scanometric detection of mercuric ion using DNA-functionalized gold nanoparticles. Anal. Chem. 2008;80(17):6805-8.
Lee et al., Colorimetric detection of mercuric ion (Hg2+) in aqueous media using DNA-functionalized gold nanoparticles. Angew Chem Int Ed Engl. 2007;46(22):4093-6.
Lee et al., Silver nanoparticle-oligonucleotide conjugates based on DNA with triple cyclic disulfide moieties, Nano Lett., 7: 2112 (2007).
Leslie et al., A new tool for oligonucleotides import into cells. Clin. Chem. 009;55: 609-10.
Lewis, Ch.1: Controlled release of bioactive agents from lactide/glycolide polymer. pp. 1-41, in Chasin et al. (eds.), Biodegradable Polymers as Drug Delivery Systems, Marcel Dekker (1990).
Li et al., Dual-reactive surfactant used for synthesis of functional nanocapsules in miniemulsion. J. Am. Chem. Soc. 2010;132(23):7823-5.

(56) References Cited

OTHER PUBLICATIONS

Li et al., Reversible and chemically programmable micelle assembly with DNA block-copolymer amiphiphiles. Nano Lett.. 2004;4(6):1055-8.

Li et al., Thermal stability of DNA functionalized gold nanoparticles, Bioconjugate Chem., 24:1790-7 (2013).

Lin et al., Effector/memory but not naive regulatory T cells are responsible for the loss of concomitant tumor immunity. J. Immunol. 2009;182: 6095-104.

Lin et al., Modeling genomic diversity and tumor dependency in malignant melanoma. Cancer Res. 2003;68: 664-73.

Liu et al., Accelerated color change of gold nanoparticles assembled by DNAzymes for simple and fast colorimetric Pb2+ detection. J. Am. Chem. Soc. 2004;126: 12298-305.

Liu et al., Cross-linked polynorbornene-coated gold nanoparticles: dependence of particle stability on cross-linking position and cross-linker structure. Langmuir. 2008;24:11169-74.

Liu et al., De-N-acetyl GM3 promotes melanoma cell migration and invasion through urokinase plasminogen activator receptor signaling-dependent MMP-2 activation. Cancer Res. 2009;69: 8662-9.

Liu et al., New poly(d-glucaramidoamine)s induce DNA nanoparticle formation and efficient gene delivery into mammalian cells. J. Am. Chem. Soc. 2004;126: 7422-3.

Liu et al., Silica Nanoparticle Supported Lipid Bilayers for Gene Delivery, Chem. Commun., 2009, 5100-5102.

Liu et al., Synthesis, stability, and cellular internalization of gold nanoparticles containing mixed peptide-poly(ethylene glycol) monolayers. Anal. Chem. 2007;79: 2221-9.

Ljubimova et al., Nanoconjugate based on polymalic acid for tumor targeting. Chem Biol Interact. Jan. 30, 2008;171(2):195-203. Epub Feb. 8, 2007.

Llovet et al., Arterial embolisation or chemoembolisation versus symptomatic treatment in patients with unresectable hepatocellular carcinoma: a randomised controlled trial. Lancet. 2002;359(9319):1734-9.

Love et al., Self-assembled monolayers of thiolates on metals as a form of nanotechnology. Chem. Rev. 2005;105: 1103-69.

Luo et al., Synthetic DNA delivery systems. Nat Biotechnol. Jan. 2000;18(1):33-7.

Ma et al., Design and synthesis of RNA miniduplexes via a synthetic linker approach. Biochemistry. 1993;32(7): 1751-8.

Major, M. et al., "Characterisation and Phase Behaviour of Phospholipid Bilayers Adsorbed on Spherical Polysaccharidic Nanoparticles," Biochimica et Biophysica Acta, 1997, 1327, 32-40.

Marabelle et al. Depleting tumor-specific Tregs at a single site eradicates disseminated tumors, J Clin Invest. 2013; 123(6):2447-2463.

Marinakos et al., "Gold Nanoparticles as Templates for the Synthesis of Hollow Nanometer-Sized Conductive Polymer Capsules," Adv. Mater. 11:34-37 (1999).

Martinson et al., Impact of Class A, B and C CpG-oligodeoxynucleotides on in vitro activation of innate immune cells in human immunodeficiency virus-1 infected individuals. Immunology. 2007;120(4):526-35.

Maruyama, et al., Nanoparticle DNA carrier with poly(L-lysine) grafted polysaccharide copolymer and poly(D,L-lactic acid). Bioconjugate Chem.. 1997;8: 735-742.

Maxwell et al., Self-assembled nanoparticle probes for recognition and detection of biomolecules. J. Am. Chem. Soc. 2002;124: 9606-12.

Maye et al., A simple method for kinetic control of DNA-induced nanoparticle assembly. J. Am. Chem. Soc. 2006; 128: 14020-1.

McAllister et al., Polymeric nanogels produced via inverse microemulsion polymerization as potential gene and antisense delivery agents, J. Am. Chem. Soc., 124:15198 (2002).

Mendell, MicroRNAs: critical regulators of development, cellular physiology and malignancy. Cell Cycle. 2005;4(9):1179-84.

Moughton et al., Hollow nanostructures from self-assembled supramolecular metallo-triblock copolymers. Soft Matter. 2009;5(12):2361-70.

Naghavi et al., Nitric oxide donors for cardiovascular implant applications. Small. Jan. 14, 2013;9(1):22-35. doi: 10.1002/smll.201200458. Epub Nov. 8, 2012. Review.

Nam et al., Nanoparticle-based bio-bar codes for the ultrasensitive detection of proteins. Science. Sep. 26, 2003;301(5641):1884-6.

Nykypanchuk et al., DNA-guided crystallization of colloidal nanoparticles. Nature. 2008;451:549-52.

Ohishi et al., Hepatocellular carcinoma detected by iodized oil. Use of anticancer agents. Radiology. 1985;154(1):25-9.

Okayasu et al., Selective and persistent deposition and gradual drainage of iodized oil, Lipiodol in the hepatocellular carcinoma after injection into the feeding hepatic artery. Am. J. Clin. Pathol. 1988;90(5):536-44.

Olshaysky et al., "Organometallic Synthesis of GaAs Crystallites Exhibiting Quantum Confinement," J. Am. Chem. Soc., 112:9438-9439 (1990).

O'Meara et al., Capture of single-stranded DNA assisted by oligonucleotide modules. Anal. Biochem. 1998;255: 195-203.

Opalinska et al., Nucleic-acid therapeutics: basic principles and recent applications. Nat Rev Drug Discov. Jul. 2002;1(7):503-14.

Ozpolat et al., Nanomedicine based approaches for the delivery of siRNA in cancer. J. Intern. Med. 2010;267(1):44-53.

Paciotti et al., Colloidal gold: a novel nanoparticle vector for tumor directed drug delivery. Drug Deliv. 2004;11(3):169-83.

Parrish et al., Soluble Camptothecin Derivatives Prepared by Click Cycloaddition Chemistry on Functional Aliphatic Polyesters. Bioconjugate Chem. 2006;18: 263-267.

Patil et al., Evidence for Novel Interdigitated Bilayer Formation of Fatty Acids During Three-Dimensional Self-Assembly on Silver Colloidal Particles. J. Am. Chem. Soc., 1997, 119 (39), 9281-9282.

Plant et al., Self-assembled phospholipid/alkanethiol biomimetic bilayers on gold. Langmuir. 1993;9:2764-7.

Platt al., Role for the class A macrophage scavenger receptor in the phagocytosis of apoptotic thymocytes in vitro. Proc Natl Acad Sci U S A. Oct. 29, 1996;93(22):12456-60.

Prasad et al., Oligonucleotides tethered to a short polyguanylic acid stretch are targeted to macrophages: enhanced antiviral activity of a vesicular stomatitis virus-specific antisense oligonucleotide. Antimicrob Agents Chemother. Nov. 1999;43(11):2689-96.

Rethore et al., Preparation of chitosan/polyglutamic acid spheres based on the use of polystyrene template as nonviral gene carrier. Tissue Engineering, 2009;15(4): 605-13.

Rethore et al., Use of templates to fabricate nanoscale spherical structures for defined architectural control. Small, 2010;6(4):488-98.

Rihova et al., Receptor-mediated targeted drug or toxin delivery. Adv. Drug Deliv. Rev., 1998;29(3): 273-89.

Rudiuk et al., Enhancement and modulation of enzymatic; activity through higher-order structural changes of giant DNA-protein multibranch conjugates. Angew Chem Int Ed Engl. Dec. 14, 2012;51(51):12694-8. doi: 10.1002/anie.201206962. Epub Nov. 9, 2012.

Sadauskas et al., Protracted elimination of gold nanoparticles from mouse liver, Nanomedicine, 2009;5(2):162-9.

Seferos et al., Locked nucleic acid-nanoparticle conjugates, Chem. Bio. Chem., 8:1230 (2007).

Sharma et al., Mutant V599EB-Raf regulates growth and vascular development of malignant melanoma tumors. Cancer Res., 2005;65: 2412-21.

Sharma et al., Targeting Akt3 signaling in malignant melanoma using isoselenocyanates. Clin. Cancer Res., 2009;15:.1674-85.

Shu et al., Gradient cross-linked biodegradable polyelectrolyte nanocapsules for intracellular protein drug delivery. Biomaterials, 2010;31 (23):6039-49.

Skwarczynski et al., Paclitaxel prodrugs: toward smarter delivery of anticancer agents. J. Med. Chem. 2006;49(25):7253-69.

Smith et al., Bioconjugated quantum dots for in vivo molecular and cellular imaging. Adv. Drug Deliv. Rev., 2008;60(11):1226-40.

Stoeva et al., Multiplexed detection of protein cancer markers with biobarcoded nanoparticle probes. J. Am. Chem. Soc., 2006;128: 8378-9.

(56) References Cited

OTHER PUBLICATIONS

Storhoff et al., One-pot colorimetric differentiation of polynucleotides with single base imperfections using gold nanoparticle probes. J. Am. Chem. Soc., 1998;120:1959-64.
Storhoff et al., Sequence-Dependent Stability of DNA-Modified Gold Nanoparticles. Langmuir. 2002;18: 6666-6670.
Storhoff et al., What controls the optical properties of DNA-linked gold nanoparticle assemblies? J. Am. Chem. Soc., 2000;122: 4640-50.
Sugihara et al., One-pot synthesis of biomimetic shell cross-linked micelles and nanocages by ATRP in alcohol/water mixtures. Angew. Chem. Int. Ed. Engl., 2010;48(20):3500-3.
Sundaram et al., Particle-mediated delivery of recombinant expression vectors to rabbit skin induces high-titered polyclonal antisera (and circumvents purification of a protein immunogen). Nucl. Acids Res., 1996;24(7): 1375-7.
Tan et al., Facile synthesis of hybrid silica nanocapsules by interfacial templating condensation and their application in fluorescence imaging. Chem. Commun. (Camb.), Nov. 2009; 7(41):6240-2.
Taton et al., Scanometric DNA array detection with nanoparticle probes. Science, 2000;289(5485):1757-60.
Thomas et al., Conjugation to gold nanoparticles enhances polyethylenimine's transfer of plasmid DNA into mammalian cells. Proc. Natl. Acad. Sci. USA, 2003;100(16): 9138-43.
Thurn et al., Labeling TiO2 nanoparticles with dyes for optical fluorescence microscopy and determination of TiO2-DNA nanoconjuqate stability. Small, 2009;5(11):1318-25.
Tkachenko et al., Cellular trajectories of peptide-modified gold particle complexes: comparison of nuclear localization signals and peptide transduction domains. Bioconjugate Chem., 2004;15(3): 482-90.
Tondelli, et al., Highly efficient cellular uptake of c-myb antisense oligonucleotides through specifically designed polymeric nanospheres. Nucl. Acids Res. 1998;26:5425-5431.
Tsao et al., Genetic interaction between NRAS and BRAF mutations and PTEN/MMAC1 inactivation in melanoma. J. Invest. Dermatol., 2004;122: 337-41.
Virmani et al., Comparison of two different methods for inoculating VX2 tumors in rabbit livers and hind limbs. J. Vasc. Interv. Radial., 2008;19(6):931-6.
Wang et al., Nanoparticles for multiplex diagnostics and imaging. Nanomedicine (Land.), 2006;1: 413-26.
Wang et al., Superparamagnetic sub-5 nm Fe@C nanoparticles: isolation, structure, magnetic properties, and directed assembly. Nano Lett., 2008;8(11):3761-5.
Wellbrock et al., V599EB-RAF is an oncogene in melanocytes. Cancer Res., 2004;64: 2338-42.
Whitesides, Proceedings of the Robert A. Welch Foundation 39th Conference on Chemical Research Nanophase Chemistry, Houston, Tex., pp. 109-121 (1995).
Wolf et al., Rapid hybridization kinetics of DNA attached to submicron latex particles. Nucl. Acids Res., 1987;15: 2911-26.
Wolfrum et al., Mechanisms and optimization of in vivo delivery of lipophilic siRNAs. Nat Biotechnol. Oct. 2007;25(10):1149-57. Epub Sep. 16, 2007.
Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.
Xing et al., Selective delivery of an anticancer drug with aptamer-functionalized liposomes to breast cancer cells in vitro and in vivo, J. Mater. Chem. B., 1:5288 (2013).
Xu et al., A gold-nanoparticle-based real-time colorimetric screening method for endonuclease activity and inhibition. Angew. Chem. Int. Ed. Engl., 2007;46(19):3468-70.
Xu et al., Homogeneous detection of nucleic acids based upon the light scattering properties of silver-coated nanoparticle probes. Anal. Chem., 2007;79(17):6650-4.
Xu et al., Thermodynamics of DNA hybridization on gold nanoparticles. J. Am. Chem. Soc., 2005;127(38): 13227-31.
Yin Win et al., Effects of particle size and surface coating on cellular uptake of polymeric nonparticles for oral delivery of anticancer drugs. Biomaterials, 2005;26: 2713-22.
You et al., Engineering the nanoparticle-biomacromolecule interface. Soft Matter, 2006;2: 190-204.
Zabner et al., Cellular and molecular barriers to gene transfer by a cationic lipid. J. Biol. Chem., 1995;270: 18997-9007.
Zamai et al., Camptothecin Poly[N-(2-Hydroxypropyl) Methacrylamide] Copolymers in Antitopoisomerase-1 Tumor Therapy: Intratumor Release and Antitumor Efficacy. Mol Cancer Ther 2003;2: 29-40.
Zhang et al., A novel paclitaxel-loaded poly(epsilon-caprolactone)/Poloxamer 188 blend nanoparticle overcoming multidrug resistance for cancer treatment. Acta Biomater., 2010;6(6):2045-52.
Zhang et al., Cationic shell-crosslinked knedel-like nanoparticles for highly efficient gene and oligonucleotide transfection of mammalian cells. Biomaterials, 2009;30(5):968-77.
Zhang et al., Nanopod formation through gold nanoparticle templated and catalyzed cross-linking of polymers bearing pendant propargyl ethers. J Am Chem Soc. Nov. 3, 2010;132(43):15151-3.
Zhang et al., Single-quantum-dot-based DNA sensor. Nat. Mater., 2005;4: 826-31.
Zhang et al., TLR9-mediated siRNA delivery for targeting of normal and malignant human hematopoietic cells in vivo. Blood. Feb. 21, 2013;121(8):1304-15. doi: 10.1182/blood-2012-07-442590. Epub Jan. 3, 2013.
Zhao et al., A rapid bioassay for single bacterial cell quantitation using bioconjugated nanoparticles. Proc. Natl. Acad. Sci. USA, 2004;101(42):15027-32.
Zimmer, Antisense oligonucleotide delivery with polyhexylcyanoacrylate nanoparticles as carriers. Methods, 1999;18: 286-95.

* cited by examiner

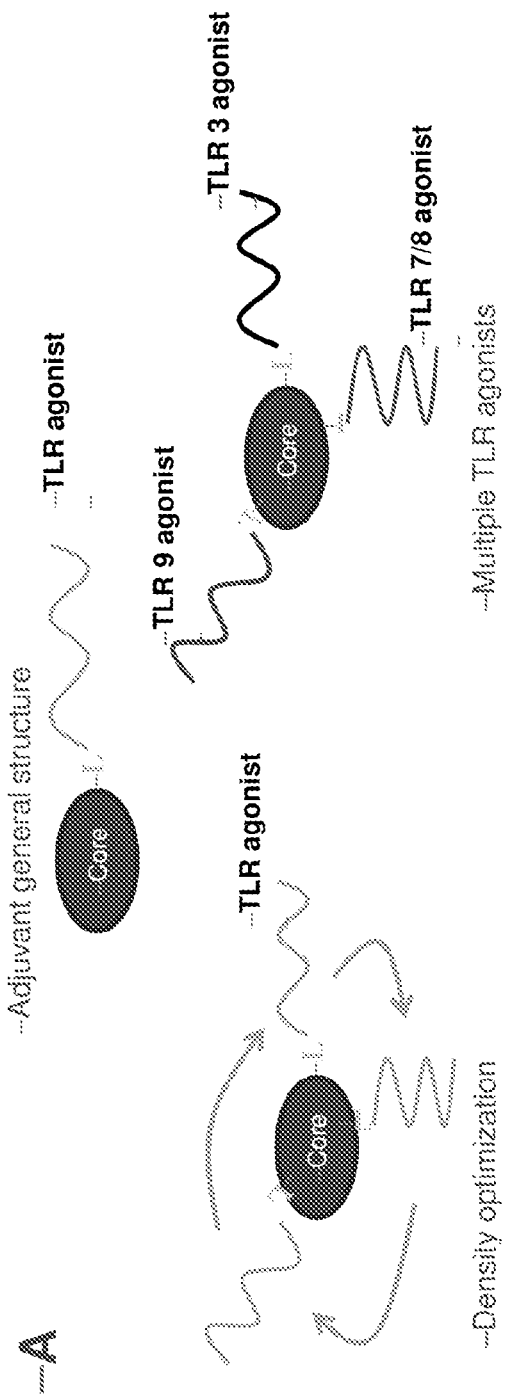
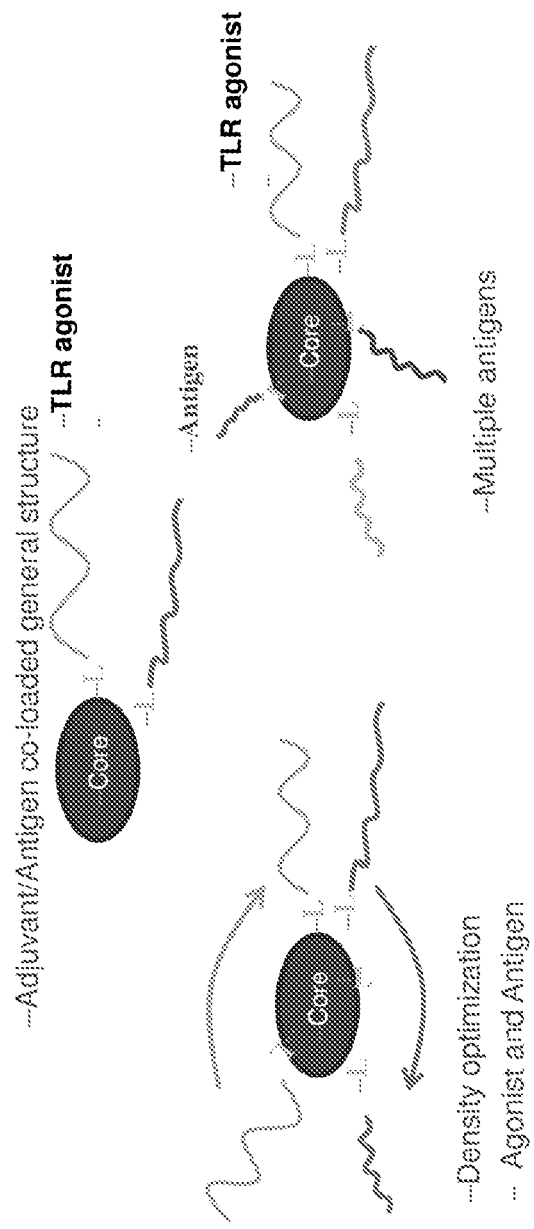
Figure 1—A
Figure 1—B

Innate and adaptive immune responses

SPHERICAL NUCLEIC ACID-BASED CONSTRUCTS AS IMMUNOSTIMULATORY AGENTS FOR PROPHYLACTIC AND THERAPEUTIC USE

RELATED APPLICATIONS

This application is a National Stage Application under 35 U.S.C. § 371 of International Application Serial No. PCT/US2014/048291, entitled "Spherical Nucleic Acid-Based Constructs As Immunostimulatory Agents For Prophylactic And Therapeutic Use" filed on Jul. 25, 2014, which claims priority under 35 U.S.C. § 119(e) to U.S. Provisional Application Ser. No. 61/858,558, entitled "SPHERICAL NUCLEIC ACID-BASED CONSTRUCTS AS IMMUNOSTIMULATORY AGENTS FOR PROPHYLACTIC AND THERAPEUTIC USE" filed on Jul. 25, 2013, the contents of each of which is herein incorporated by reference in its entirety.

FIELD OF INVENTION

The invention relates to nanoscale constructs of agonists of nucleic acid-interacting complexes, such as agonists of TLR, as well as methods and compositions thereof.

BACKGROUND OF INVENTION

The immune system is a highly evolved, exquisitely precise endogenous mechanism for clearing foreign, harmful, and unnecessary material including pathogens and senescent or malignant host cells. It is known that modulating the immune system for therapeutic or prophylactic purposes is possible by introducing compounds that modulate the activity of specific immune cells. A primary example is vaccines, which have shown the ability to induce protection against pathogens as well as cancerous cells. The first modern vaccine formulations included live/attenuated or inactivated pathogens, but these were deemed too toxic in many instances or did not provide protective immunity. Purified protein derivatives and other antigenic subunit vaccine strategies have been pursued, but these typically lead to mildly protective or inefficient responses. It is now appreciated that effective immunity, in most instances, is known to require use of immunostimulatory compounds, which, among other things, provide the necessary signals to induce more robust, specific, and long-lived responses, including cell-mediated immunity and immunologic memory. The nature of these responses can be modulated by the type of immunostimulatory compound(s) introduced. Indeed, it has been postulated that immunostimulatory compounds administered together in the presence of appropriate antigenic stimuli can be used to elicit a wide variety of immune responses, with the potential to treat or prevent various ailments, including infectious diseases and cancer. These can also potentially be used to vaccinate immunocompromised populations, such as children and the elderly.[1]

Existing vaccines fail to induce effective immune responses in a variety of diseases with critical worldwide impact, including AIDS, malaria, *chlamydia*, various malignancies and allergies or allergic diseases, such as asthma. Among the immunostimulatory compounds being developed, agonists of Toll-like receptors (TLR) have demonstrated outstanding potential. Agonists of TLR4, such as monophosphoryl lipid A (MPL) have reached late stages of clinical trials and approval in various countries in some instances.[2] Despite these promising results, there is still a clear and significant need for compounds which can safely and effective induce responses that can clear intracellular pathogens and cancers, such as inducers of cell-mediated immunity. Agonists of TLR 3, TLR 7/8 and TLR 9 have excellent potential due to their potent ability to induce Th1 cell-mediated immune responses. A synthetic TLR 7/8 agonist, imiquimod, has been approved to treat various skin diseases, including superficial carcinomas and genital warts, and is being developed for a variety of other indications. Similarly, agonists of TLR 9 are in various stages of clinical development, for treatment of various diseases with large unmet medical needs. However, concerns due to lack of efficacy, off-target phosphorothioate effects, and toxicity have slowed effective clinical translation of TLR 7/8 and 9 agonists.

SUMMARY OF INVENTION

Described herein are novel methods and compositions for enhancing immune responses and activating nucleic acid interacting complexes such as TLRs using a nanoscale construct. Aspects of the invention relate to nanoscale constructs having a corona of an agonist of nucleic acid-interacting complexes wherein the surface density of the agonist of nucleic acid-interacting complexes is at least 0.3 pmol/cm$^2$.

In other aspects the invention is a nanoscale construct having a corona of an agonist of nucleic acid-interacting complexes, and an antigen incorporated into the corona. In some embodiments the surface density of the antigen is at least 0.3 pmol/cm$^2$. In other embodiments the antigen includes at least two different types of antigen.

In yet other aspects the invention is a nanoscale construct having a corona with at least two agonists of nucleic acid-interacting complexes incorporated, wherein the agonists are selected from the group consisting of TLR 3, 7/8, and/or 9 agonists.

In some embodiments the agonist of nucleic acid-interacting complexes contains a spacer.

In other embodiments the agonist of nucleic acid-interacting complexes is RNA or DNA. The agonists of nucleic acid-interacting complexes may be, for instance, a double stranded RNA, such as poly(I:C). Alternatively the agonist of nucleic acid-interacting complexes may be a single stranded RNA such as an RNA containing UUG-motifs. In some embodiments the agonist of nucleic acid-interacting complexes is an unmethylated deoxyribonucleic acid, such as a CpG oligonucleotide.

The nanoscale construct, in some embodiments, contains a nanoparticle core at the center of the corona which is optionally metallic. The metallic core may be selected from the group consisting of gold, silver, platinum, aluminum, palladium, copper, cobalt, indium, nickel and mixtures thereof. In some embodiments the nanoparticle core comprises gold. In other embodiments the nanoscale construct is degradable.

In certain embodiments, the diameter of the nanoscale construct is from 1 nm to about 250 nm in mean diameter, about 1 ran to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 ran in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, or about 1 nm to about 10 nm in mean diameter.

In other aspects the invention is a nanoscale construct of a corona of an agonist of nucleic acid-interacting complexes, wherein the agonist is nucleic acid having at least one phosphodiester internucleotide linkage. In some embodiments the agonist is a CpG oligonucleotide. In other embodiments each internucleotide linkage of the nucleic acid is a phosphodiester linkage.

In embodiments of the invention the corona is a spherical corona.

A vaccine composed of a nanoscale construct described herein and a carrier is provided according to other aspects of the invention.

A method for delivering a therapeutic agent to a cell by delivering the nanoscale construct of the invention to the cell is provided in other aspects.

A method for regulating expression of a target molecule is provided in other aspects of the invention. The method involves delivering the nanoscale construct of the invention to the cell. In some embodiments the target molecule is a TLR selected from the group consisting of TLR3, 7, 8, and 9.

A method for activating a TLR by delivering the nanoscale construct as described herein to the cell is provided in other aspects of the invention.

According to other aspects the invention is a method of treating a subject, involving administering to the subject the nanoscale construct as described herein in an effective amount to stimulate an immune response. In some embodiments the subject has an infectious disease, a cancer, an autoimmune disease, allergy, or an allergic disease such as asthma.

In yet other embodiments, the invention is a method of inducing an immune response in a subject, by administering to the subject a nanoscale construct of a corona of an agonist of nucleic acid-interacting complexes, wherein the agonist is nucleic acid having at least one phosphodiester internucleotide linkage in an effective amount to stimulate an immune response.

In certain embodiments, the method involves delivering a therapeutic or detection modality to a cell.

Further aspects of the invention relate to a kit comprising: a nanoscale construct optionally including a nanoparticle core; and having an agonist of nucleic acid-interacting complexes and instructions for assembly of an agonist of nucleic acid-interacting complexes-corona. In certain embodiments, the kit further comprises instructions for use.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 1A-1B show a schematic non-limiting example of a nanoscale construct of the invention. A. A general structure of an adjuvant nanoscale construct having a core and one or more agonists of nucleic acid interacting complexes, such as TLR agonists bound thereto is shown. B. A general structure of an adjuvant nanoscale construct having a core and one or more TLR agonists and one or more antigens bound thereto is shown.

FIG. 6 shows that the SNAs can co-present a therapeutic vaccine antigen and adjuvant on a single nanoparticle, and may simultaneously target multiple immunostimulatory receptors (e.g. TLR 3, 4, 7/8, 9).

FIG. 17A shows the expression levels of TNF, IL-12, and IL-6 induced by CTL oligo, CTL SNA, CpG 1826, and AST-008. FIG. 17B presents the NF-κB activation stemming from the indicated agents.

FIG. 21A schematically represents the protocol: splenocytes were grown for 28 days, challenged on Day 0 and Day 21, and then restimulated with SIINFEKL and probed for INF-γ with ELISPOT on Day 28. FIG. 21B is a graph depicting the results. ****p<0.0001.

FIG. 22A illustrates the protocol: the right flanks of C57BL/6 mice were injected with 1×10$^6$ E.G7-OVA lymphoma (11 per group). The mice were then challenged three times with 100 µg OVA s.c., 1.8 µg OVA$_{257-264}$ s.c., and 0.92 nmol oligo in AST-008, and sacrificed at 2000 mm$^3$. FIG. 22B is a graph of the results. *p<0.05 using Two-way ANOVA.

DETAILED DESCRIPTION

Figure 2:
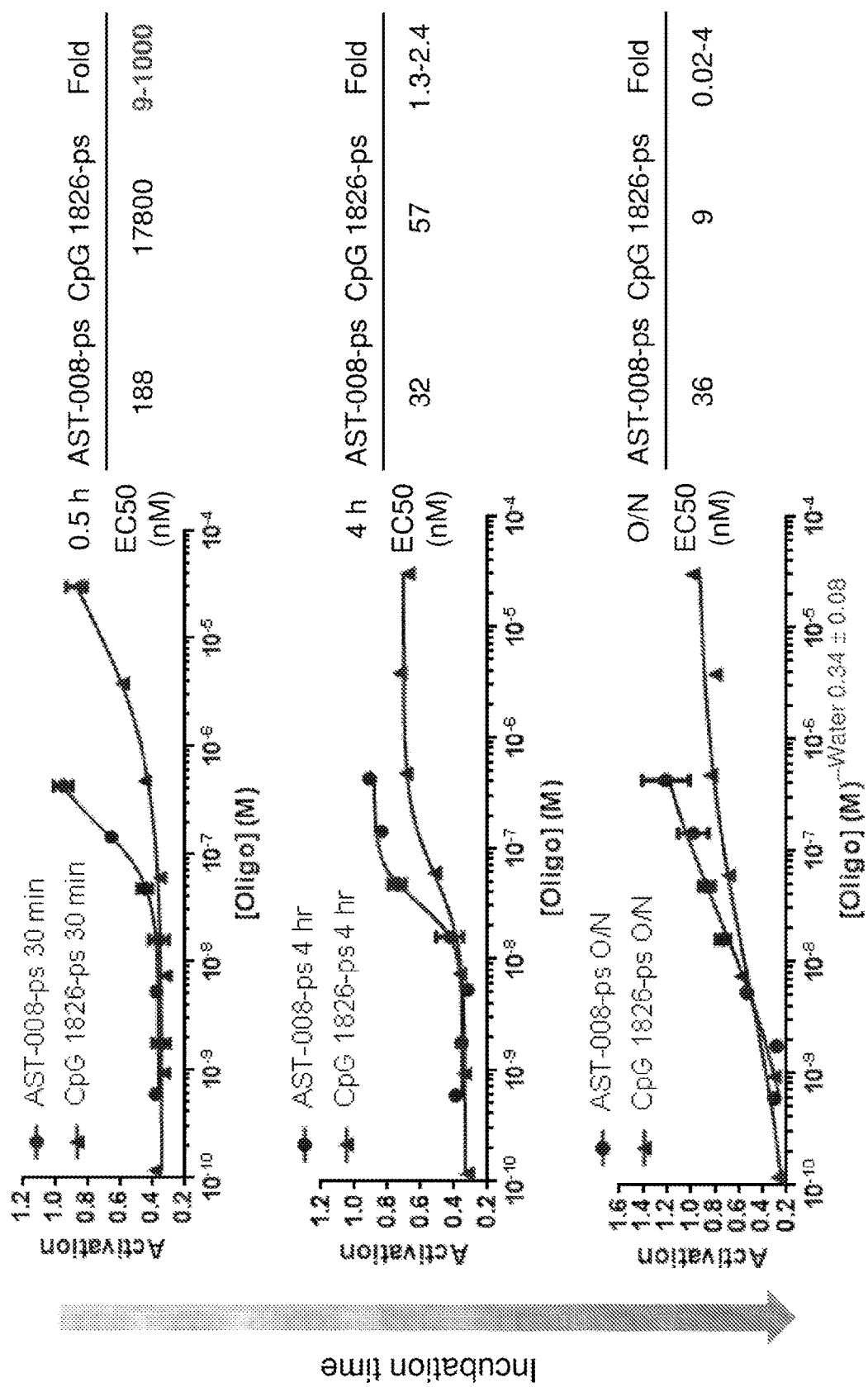
FIG. 2 is a set of graphs depicting markedly enhanced potency in macrophages of the nanoscale constructs of the invention over agonists of nucleic acid-interacting complexes (CpG oligonucleotides) in solution.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention, in some aspects, overcomes several major hurdles encountered by conventional TLR 3, TLR 7/8, and TLR 9 agonists by achieving faster activation, creating a multivalent structure, changing cellular distribution, and facilitating simple and scalable synthesis of various adjuvant and antigen-containing structures, among others. The constructs of the invention result in more effective vaccines for prophylactic or therapeutic uses in treating a wide variety of diseases/infections including, for example, AIDS, malaria, chlamydia, campylobacter, cytomegalovirus, dengue, Epstein-Ban mononucleosis, foot and mouth disease, rabies, Helicobacter pylori gastric ulcers, hepatitis A, B, C, herpes simplex, influenza, leishmaniasis, cholera, diphtheria, Haemophilus influenza, meningococcal meningitis, plague, pneumococcal pneumonia, tetanus, typhoid fever, respiratory synctial virus, rhinovirus, schistosomiasis, shigella, streptococcus group A and B, tuberculosis, vibrio cholera, salmonella, aspergillus, blastomyces, histoplasma, candida, cryptococcus, pneumocystis, and urinary tract infections; various food allergies such as peanut, fruit, garlic, oats, meat, milk, fish, shellfish, soy, tree nut, wheat, gluten, egg, sulphites; various drug allergies such as to tetracycline, Dilantin, carbamazepine, penicillins, cephalosporins, sulfonamides, NSAIDs, intravenous contrast dye, local anesthetics; autoimmune diseases such as multiple sclerosis, lupus, inflammatory bowel disease, Crohn's disease, ulcerative colitis, asthma, and COPD; and cancers such as melanoma, breast cancer, prostate cancer, bladder cancer, NSCLC, glioblastoma multiforme, among others.

A set of exemplary nanoscale constructs of the invention is shown in the schematic of FIG. 1. The platform described herein is useful for loading one or multiple agonists of nucleic acid-interacting complexes (A) or one or multiple agonists of nucleic acid-interacting complexes and antigen (B). Optimization of: (1) nucleic acid interacting complex, such as a TLR that is targeted (TLR 3, 7/8, and/or 9), (2) density of agonist of nucleic acid-interacting complexes, (3) antigen density, (4) multiple antigen presentation, (5) core composition, size, and charge, and (6) core linker chemistry "L", and (7) agonist chemical structure is expected to yield novel paradigms in vaccine development. In particular, agonists of nucleic acid-interacting complexes include double stranded RNA (such as poly(I:C), TLR 3), single stranded RNA (such as strands containing UUG-motifs, TLR 7/8), and unmethylated deoxyribonucleic acid and derivatives (such as strands containing CpG motifs).

Aspects of the invention relate to nanoscale constructs. A nanoscale construct refers to a nanometer sized construct having one or more nucleic acids held in a geometrical position. The nanoscale construct typically is referred to as a corona of a set of nucleic acids. A corona, as used herein, refers to an exterior shell composed of nucleic acid molecules. The corona may have a nanoparticle core composed of nucleic acids or other materials, such as metals. Alternatively, the corona may simply be a set of nucleic acids arranged in a geometric shape with a hollow core, i.e. a 3-dimensionally shaped layer of nucleic acids. Typically, but not always, the corona has a spherical shape.

In the instance, when the corona includes a nanoparticle core the nucleic acids may be linked directly to the core. Some or all of the nucleic acids may be linked to other nucleic acids either directly or indirectly through a covalent or non-covalent linkage. The linkage of one nucleic acid to another nucleic acid may be in addition to or alternatively to the linkage of that nucleic acid to a core. One or more of the nucleic acids may also be linked to other molecules such as an antigen.

When the corona does not include a nanoparticle core, the nucleic acids may be linked to one another either directly or indirectly through a covalent or non-covalent linkage. In some embodiments the corona that does not include a nanoparticle core may be formed by layering the nucleic acids on a lattice or other dissolvable structure and then dissolving the lattice or other structure to produce an empty center.

As used herein, the nano scale construct is a construct having an average diameter on the order of nanometers (i.e., between about 1 nm and about 1 micrometer. For example, in some instances, the diameter of the nanoparticle is from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 ran in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, about 1 nm to about 20 nm in mean diameter, about 1 nm to about 10 nm in mean diameter, about 5 nm to about 150 nm in mean diameter, about 5 to about 50 nm in mean diameter, about 10 to about 30 nm in mean diameter, about 10 to 150 nm in mean diameter, about 10 to about 100 nm in mean diameter, about 10 to about 50 nm in mean diameter, about 30 to about 100 nm in mean diameter, or about 40 to about 80 nm in mean diameter.

In some instances the corona includes a nanoparticle core that is attached to one or more agonists of nucleic acid-interacting complexes and/or antigens. As used herein, a nanoparticle core refers to the nanoparticle component of a nanoparticle construct, without any attached modalities. In some instances, the nanoparticle core is metallic. It should be appreciated that the nanoparticle core can comprise any metal. Several non-limiting examples of metals include gold, silver, platinum, aluminum, palladium, copper, cobalt, indium, nickel and mixtures thereof. In some embodiments, the nanoparticle core comprises gold. For example, the nanoparticle core can be a lattice structure including degradable gold. Nanoparticles can also comprise semiconductor and magnetic materials.

Non-limiting examples of nanoparticles compatible with aspects of the invention are described in and incorporated by reference from: U.S. Pat. No. 7,238,472, US Patent Publication No. 2003/0147966, US Patent Publication No. 2008/0306016, US Patent Publication No. 2009/0209629, US Patent Publication No. 2010/0136682, US Patent Publication No. 2010/0184844, US Patent Publication No. 2010/0294952, US Patent Publication No. 2010/0129808, US Patent Publication No. 2010/0233270, US Patent Publication No. 2011/0111974, PCT Publication No. WO 2002/096262, PCT Publication No. WO 2003/08539, PCT Publication No. WO 2006/138145, PCT Publication No. WO 2008/127789, PCT Publication No. WO 2008/098248, PCT Publication No. WO 2011/079290, PCT Publication No. WO 2011/053940, PCT Publication No. WO 2011/017690 and PCT Publication No. WO 2011/017456. Nanoparticles associated with the invention can be synthesized according to any means known in the art or can be obtained commercially. For example, several non-limiting examples of commercial suppliers of nanoparticles include: Ted Pella, Inc., Redding, Calif., Nanoprobes, Inc., Yaphank, N.Y., Vacuum Metallurgical Co, Ltd., Chiba, Japan and Vector Laboratories, Inc., Burlington, Calif.

Agonists of Nucleic Acid-Interacting Complexes

A nucleic acid-interacting complex as used herein refers to a molecule or complex of molecules that interact with a nucleic acid molecule and are stimulated to produce an immune response in response to that interaction. The molecule or complex of molecules may be a receptor, for instance. In some embodiments a nucleic acid-interacting complex is a pattern recognition receptor (PRR) complex. PRRs are a primitive part of the immune system composed of proteins expressed by cells of the innate immune system to identify pathogen-associated molecular patterns (PAMPs), which are associated with microbial pathogens or cellular stress, as well as damage-associated molecular patterns (DAMPs), which are associated with cell components released during cell damage. PRRs include but are not limited to membrane-bound PRRs, such as receptor kinases, toll-like receptors (TLR), and C-type lectin Receptors (CLR) (mannose receptors and asialoglycoprotein receptors); Cytoplasmic PRRs such as RIG-I-like receptors (RLR), RNA Helicases, Plant PRRs, and NonRD kinases; and secreted PRRs.

Nucleic acid-interacting complexes include but are not limited to TLRs, RIG-I, transcription factors, cellular translation machinery, cellular transcription machinery, nucleic-acid acting enzymes, and nucleic acid associating autoantigens. Nucleic acid molecules that are agonists of a nucleic acid-interacting complex include but are not limited to TLR agonists, and agonists of RIG-I, transcription factors, cellular translation machinery, cellular transcription machinery, nucleic-acid acting enzymes, and nucleic acid associating autoantigens.

In some embodiments an agonist of a nucleic acid-interacting complex is a TLR agonist. A TLR agonist, as used herein is a nucleic acid molecule that interacts with and stimulates the activity of a TLR.

Toll-like receptors (TLRs) are a family of highly conserved polypeptides that play a critical role in innate immunity in mammals. At least ten family members, designated TLR1-TLR10, have been identified. The cytoplasmic domains of the various TLRs are characterized by a Toll-interleukin 1 (IL-1) receptor (TIR) domain. Medzhitov R et al. (1998) *Mol Cell* 2:253-8. Recognition of microbial invasion by TLRs triggers activation of a signaling cascade that is evolutionarily conserved in *Drosophila* and mammals. The TIR domain-containing adaptor protein MyD88 has been reported to associate with TLRs and to recruit IL-1 receptor-associated kinase (IRAK) and tumor necrosis factor (TNF) receptor-associated factor 6 (TRAF6) to the TLRs. The MyD88-dependent signaling pathway is believed to lead to activation of NF-κB transcription factors and c-Jun NH₂ terminal kinase (Jnk) mitogen-activated protein kinases (MAPKs), critical steps in immune activation and production of inflammatory cytokines. For a review, see Aderem A et al. (2000) Nature 406:782-87.

TLRs are believed to be differentially expressed in various tissues and on various types of immune cells. For example, human TLR7 has been reported to be expressed in placenta, lung, spleen, lymph nodes, tonsil and on plasmacytoid precursor dendritic cells (pDCs). Chuang T-H et al. (2000) Eur Cytokine Netw 11:372-8); Kadowaki N et al. (2001) J Exp Med 194:863-9. Human TLR8 has been reported to be expressed in lung, peripheral blood leukocytes (PBL), placenta, spleen, lymph nodes, and on monocytes. Kadowaki N et al. (2001) J Exp Med 194:863-9; Chuang T-H et al. (2000) Eur Cytokine Netw 11:372-8. Human TLR9 is reportedly expressed in spleen, lymph nodes, bone marrow, PBL, and on pDCs, and B cells. Kadowaki N et al. (2001) J Exp Med 194:863-9; Bauer S et al. (2001) Proc Natl Acad Sci USA 98:9237-42; Chuang T-H et al. (2000) Eur Cytokine Netw 11:372-8.

Nucleotide and amino acid sequences of human and murine TLR7 are known. See, for example, GenBank Accession Nos. AF240467, AF245702, NM_016562, AF334942, NM_133211; and AAF60188, AAF78035, NP_057646, AAL73191, and AAL73192, the contents of all of which are incorporated herein by reference. Human TLR7 is reported to be 1049 amino acids long. Murine TLR7 is reported to be 1050 amino acids long. TLR7 polypeptides include an extracellular domain having a leucine-rich repeat region, a transmembrane domain, and an intracellular domain that includes a TIR domain.

Nucleotide and amino acid sequences of human and murine TLR8 are known. See, for example, GenBank Accession Nos. AF246971, AF245703, NM_016610, XM_045706, AY035890, NM_133212; and AAF64061, AAF78036, NP_057694, XP_045706, AAK62677, and NP_573475, the contents of all of which is incorporated herein by reference. Human TLR8 is reported to exist in at least two isoforms, one 1041 amino acids long and the other 1059 amino acids long. Murine TLR8 is 1032 amino acids long. TLR8 polypeptides include an extracellular domain having a leucine-rich repeat region, a transmembrane domain, and an intracellular domain that includes a TIR domain.

Nucleotide and amino acid sequences of human and murine TLR9 are known. See, for example, GenBank Accession Nos. NM_017442, AF259262, AB045180, AF245704, AB045181, AF348140, AF314224, NM_031178; and NP_059138, AAF72189, BAB19259, AAF78037, BAB19260, AAK29625, AAK28488, and NP_112455, the contents of all of which are incorporated herein by reference. Human TLR9 is reported to exist in at least two isoforms, one 1032 amino acids long and the other 1055 amino acids. Murine TLR9 is 1032 amino acids long. TLR9 polypeptides include an extracellular domain having a leucine-rich repeat region, a transmembrane domain, and an intracellular domain that includes a TIR domain.

As used herein, the term "TLR signaling" refers to any aspect of intracellular signaling associated with signaling through a TLR. As used herein, the term "TLR-mediated immune response" refers to the immune response that is associated with TLR signaling.

A TLR7-mediated immune response is a response associated with TLR7 signaling. TLR7-mediated immune response is generally characterized by the induction of IFN-α and IFN-inducible cytokines such as IP-10 and I-TAC. The levels of cytokines IL-1α/β, IL-6, IL-8, MIP-1α/β and MIP-3α/β induced in a TLR7-mediated immune response are less than those induced in a TLR8-mediated immune response.

A TLR8-mediated immune response is a response associated with TLR8 signaling. This response is further characterized by the induction of pro-inflammatory cytokines such as IFN-γ, IL-12p40/70, TNF-α, IL-1α/β, IL-6, IL-8, MIP-1α/β and MIP-3α/β.

A TLR9-mediated immune response is a response associated with TLR9 signaling. This response is further characterized at least by the production/secretion of IFN-γ and IL-12, albeit at levels lower than are achieved via a TLR8-mediated immune response.

As used herein, a "TLR7/8 agonist" collectively refers to any nucleic acid that is capable of increasing TLR7 and/or TLR8 signaling (i.e., an agonist of TLR7 and/or TLR8). Some TLR7/8 ligands induce TLR7 signaling alone (e.g., TLR7 specific agonists), some induce TLR8 signaling alone (e.g., TLR8 specific agonists), and others induce both TLR7 and TLR8 signaling.

The level of TLR7 or TLR8 signaling may be enhanced over a pre-existing level of signaling or it may be induced over a background level of signaling. TLR7 ligands include, without limitation, guanosine analogues such as C8-substituted guanosines, mixtures of ribonucleosides consisting essentially of G and U, guanosine ribonucleotides and RNA or RNA-like molecules (PCT/US03/10406), and adenosine-based compounds (e.g., 6-amino-9-benzyl-2-(3-hydroxypropoxy)-9H-purin-8-ol, and similar compounds made by Sumitomo (e.g., CL-029)).

As used herein, the term "guanosine analogues" refers to a guanosine-like nucleotide (excluding guanosine) having a chemical modification involving the guanine base, guanosine nucleoside sugar, or both the guanine base and the guanosine nucleoside sugar. Guanosine analogues specifically include, without limitation, 7-deaza-guanosine.

Guanosine analogues further include C8-substituted guanosines such as 7-thia-8-oxoguanosine (immunosine), 8-mercaptoguanosine, 8-bromoguanosine, 8-methylguanosine, 8-oxo-7,8-dihydroguanosine, C8-arylamino-2'-deoxyguanosine, C8-propynyl-guanosine, C8- and N7-substituted guanine ribonucleosides such as 7-allyl-8-oxoguanosine (loxoribine) and 7-methyl-8-oxoguanosine, 8-aminoguanosine, 8-hydroxy-2'-deoxyguanosine, 8-hydroxyguanosine, and 7-deaza 8-substituted guanosine.

TLR8 ligands include mixtures of ribonucleosides consisting essentially of G and U, guanosine ribonucleotides and RNA or RNA-like molecules (PCT/US03/10406). Additional TLR8 ligands are also disclosed in Gorden et al. J. Immunol. 2005, 174:1259-1268).

As used herein, the term "TLR9 agonist" refers to any agent that is capable of increasing TLR9 signaling (i.e., an agonist of TLR9). TLR9 agonists specifically include, without limitation, immunostimulatory nucleic acids, and in particular CpG immunostimulatory nucleic acids.

As used herein, the term "immunostimulatory CpG nucleic acids" or "immunostimulatory CpG oligonucleotides" refers to any CpG-containing nucleic acid that is capable of activating an immune cell. At least the C of the CpG dinucleotide is typically, but not necessarily, unmethylated. Immunostimulatory CpG nucleic acids are described in a number of issued patents and published patent applications, including U.S. Pat. Nos. 6,194,388; 6,207,646; 6,218,371; 6,239,116; 6,339,068; 6,406,705; and 6,429,199.

In some embodiments the agonists of nucleic acid-interacting complexes is an immunostimulatory oligonucleotide. An "immunostimulatory oligonucleotide" as used herein is any nucleic acid (DNA or RNA) containing an immunostimulatory motif or backbone that is capable of inducing an immune response. An induction of an immune response refers to any increase in number or activity of an immune cell, or an increase in expression or absolute levels of an immune factor, such as a cytokine. Immune cells include, but are not limited to, NK cells, CD4+T lymphocytes, CD8+T lymphocytes, B cells, dendritic cells, macrophage and other antigen-presenting cells. Cytokines include, but are not limited to, interleukins, TNF-α, IFN-α,β and γ, Flt-ligand, and co-stimulatory molecules. Immunostimulatory motifs include, but are not limited to CpG motifs and T-rich motifs.

A non-limiting set of immunostimulatory oligonucleotides includes:

```
dsRNA (TLR 3): poly(A:C) and poly(I:C)
ssRNA (TLR7/8):
                                        (SEQ ID NO: 13)
CCGUCUGUUGUGUGACUC (SEQ ID NO: 14)
GCCACCGAGCCGAAGGCACC (SEQ ID NO: 15)
UAUAUAUAUAUAUAUAUAUA (SEQ ID NO: 16)
UUAUUAUUAUUAUUAUUAUU (SEQ ID NO: 17)
UUUUAUUUUAUUUUAUUUUA (SEQ ID NO: 18)
UGUGUGUGUGUGUGUGUGUG (SEQ ID NO: 19)
UUGUUGUUGUUGUUGUUGUU (SEQ ID NO: 20)
UUUGUUUGUUUGUUUGUUUG (SEQ ID NO: 21)
UUAUUUAUUUAUUUAUUUAU (SEQ ID NO: 22)
UUGUUUGUUUGUUUGUUUGU (SEQ ID NO: 23)
GCCCGUCUGUUGUGUGACUC (SEQ ID NO: 24)
GUCCUUCAAGUCCUUCAA DNA (TLR9):
                                        (SEQ ID NO: 25)
GGTGCATCGATGCAGGGGGG (SEQ ID NO: 26)
TCCATGGACGTTCCTGAGCGTT (SEQ ID NO: 27)
TCGTCGTTCGAACGACGTTGAT (SEQ ID NO: 28)
TCGTCGACGATCCGCGCGCGCG (SEQ ID NO: 29)
GGGGTCAACGTTGAGGGGGG (SEQ ID NO: 30)
TCGTCGTTTTGTCGTTTTGTCGTT (SEQ ID NO: 31)
TCGTCGTTGTCGTTTTGTCGTT
```

```
                                        (SEQ ID NO: 32)
GGGGGACGATCGTCGGGGGG (SEQ ID NO: 33)
GGGGACGACGTCGTGGGGGGG (SEQ ID NO: 34)
TCGTCGTTTTCGGCGCGCGCCG (SEQ ID NO: 35)
TCGTCGTCGTTCGAACGACGTTGAT
```

The immunostimulatory oligonucleotides may be linked to the core or to one another or to other molecules such an antigens. For instance, the oligonucleotides may be conjugated to a linker via the 5' end or the 3' end. E.g. [Sequence, 5'-3']-Linker or Linker-[Sequence, 5'-3'].

The terms "oligonucleotide" and "nucleic acid" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymidine (T) or uracil (U)) or a substituted purine (e.g., adenine (A) or guanine (G)). Thus, the term embraces both DNA and RNA oligonucleotides. The terms shall also include polynucleosides (i.e., a polynucleotide minus the phosphate) and any other organic base containing polymer. Oligonucleotides can be obtained from existing nucleic acid sources (e.g., genomic or cDNA), but are preferably synthetic (e.g., produced by nucleic acid synthesis). A polynucleotide of the nanoscale construct and optionally attached to a nanoparticle core can be single stranded or double stranded. A double stranded polynucleotide is also referred to herein as a duplex. Double-stranded oligonucleotides of the invention can comprise two separate complementary nucleic acid strands.

As used herein, "duplex" includes a double-stranded nucleic acid molecule(s) in which complementary sequences are hydrogen bonded to each other. The complementary sequences can include a sense strand and an antisense strand. The antisense nucleotide sequence can be identical or sufficiently identical to the target gene to mediate effective target gene inhibition (e.g., at least about 98% identical, 96% identical, 94%, 90% identical, 85% identical, or 80% identical) to the target gene sequence.

A double-stranded polynucleotide can be double-stranded over its entire length, meaning it has no overhanging single-stranded sequences and is thus blunt-ended. In other embodiments, the two strands of the double-stranded polynucleotide can have different lengths producing one or more single-stranded overhangs. A double-stranded polynucleotide of the invention can contain mismatches and/or loops or bulges. In some embodiments, it is double-stranded over at least about 70%, 80%, 90%, 95%, 96%, 97%, 98% or 99% of the length of the oligonucleotide. In some embodiments, the double-stranded polynucleotide of the invention contains at least or up to 1, 2, 3, 4, 5, 6, 7, 8, 9, 10, 11, 12, 13, 14, or 15 mismatches.

Polynucleotides associated with the invention can be modified such as at the sugar moiety, the phosphodiester linkage, and/or the base. As used herein, "sugar moieties" includes natural, unmodified sugars, including pentose, ribose and deoxyribose, modified sugars and sugar analogs. Modifications of sugar moieties can include replacement of a hydroxyl group with a halogen, a heteroatom, or an aliphatic group, and can include functionalization of the hydroxyl group as, for example, an ether, amine or thiol.

Modification of sugar moieties can include 2'-O-methyl nucleotides, which are referred to as "methylated." In some instances, polynucleotides associated with the invention may only contain modified or unmodified sugar moieties, while in other instances, polynucleotides contain some sugar moieties that are modified and some that are not.

In some instances, modified nucleomonomers include sugar- or backbone-modified ribonucleotides. Modified ribonucleotides can contain a non-naturally occurring base such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides can have the 2'—OH group replaced by an H, alkoxy (or OR), R or alkyl, halogen, SH, SR, amino (such as $NH_2$, NHR, $NR_2$,), or CN group, wherein R is lower alkyl, alkenyl, or alkynyl. In some embodiments, modified ribonucleotides can have the phosphodiester group connecting to adjacent ribonucleotides replaced by a modified group, such as a phosphorothioate group.

In some aspects, 2'-O-methyl modifications can be beneficial for reducing undesirable cellular stress responses, such as the interferon response to double-stranded nucleic acids. Modified sugars can include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—$OCH_2CH=CH_2$), 2'-propargyl, 2'-propyl, ethynyl, ethenyl, propenyl, and cyano and the like. The sugar moiety can also be a hexose.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In some embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In some embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "hydrophobic modifications' refers to modification of bases such that overall hydrophobicity is increased and the base is still capable of forming close to regular Watson-Crick interactions. Non-limiting examples of base modifications include 5-position uridine and cytidine modifications like phenyl, 4-pyridyl, 2-pyridyl, indolyl, and isobutyl, phenyl ($C_6H_5OH$); tryptophanyl ($C_8H_6N$)$CH_2CH$ ($NH_2$)CO), Isobutyl, butyl, aminobenzyl; phenyl; naphthyl, The term "heteroatom" includes atoms of any element other than carbon or hydrogen. In some embodiments, preferred heteroatoms are nitrogen, oxygen, sulfur and phosphorus. The term "hydroxy" or "hydroxyl" includes groups with an —OH or —$O^-$ (with an appropriate counterion). The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}OR'$, $(CR'R'')_{0-3}CO_2R'$, or $(CR'R'')_{0-3}OR'$ groups; wherein each R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In some aspects, the nucleomonomers of a polynucleotide of the invention are RNA nucleotides, including modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

As used herein, the term "linkage" includes a naturally occurring, unmodified phosphodiester moiety (—O—($PO^{2-}$)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothioate linkages.

In some aspects, polynucleotides of the invention comprise 3' and 5' termini (except for circular oligonucleotides). The 3' and 5' termini of a polynucleotide can be substantially protected from nucleases, for example, by modifying the 3' or 5' linkages (e.g., U.S. Pat. No. 5,849,902 and WO 98/13526). Oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. Antisense Res. Dev. 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3'linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

In some aspects, polynucleotides can comprise both DNA and RNA.

In some aspects, at least a portion of the contiguous polynucleotides are linked by a substitute linkage, e.g., a phosphorothioate linkage. The presence of substitute linkages can improve pharmacokinetics due to their higher affinity for serum proteins.

CpG sequences, while relatively rare in human DNA are commonly found in the DNA of infectious organisms such as bacteria. The human immune system has apparently evolved to recognize CpG sequences as an early warning sign of infection and to initiate an immediate and powerful immune response against invading pathogens without causing adverse reactions frequently seen with other immune stimulatory agents. Thus CpG containing nucleic acids, relying on this innate immune defense mechanism can utilize a unique and natural pathway for immune therapy. The effects of CpG nucleic acids on immune modulation have been described extensively in U.S. Pat. No. 6,194,388, and published patent applications, such as PCT US95/01570), PCT/US97/19791, PCT/US98/03678; PCT/US98/10408; PCT/US98/04703; PCT/US99/07335; and PCT/US99/09863.

A "CpG oligonucleotide" is a nucleic acid which includes at least one unmethylated CpG dinucleotide. In some embodiments, the nucleic acid includes three or more unmethylated CpG dinucleotides. A nucleic acid containing at least one "unmethylated CpG dinucleotide" is a nucleic acid molecule which contains an unmethylated cytosine in a cytosine-guanine dinucleotide sequence (i.e. "CpG DNA" or DNA containing a 5' cytosine followed by 3' guanosine and linked by a phosphate bond) and activates the immune system.

The immunostimulatory oligonucleotides of the nanoscale construct are preferably in the range of 6 to 100 bases in length. However, nucleic acids of any size greater than 6 nucleotides (even many kb long) are capable of inducing an immune response according to the invention if sufficient immunostimulatory motifs are present. Preferably the immunostimulatory nucleic acid is in the range of between 8 and 100 and in some embodiments between 8 and 50 or 8 and 30 nucleotides in size.

In some embodiments the immunostimulatory oligonucleotides have a modified backbone such as a phosphorothioate (PS) backbone. In other embodiments the immunostimulatory oligonucleotides have a phosphodiester (PO) backbone. In yet other embodiments immunostimulatory oligonucleotides have a mixed PO and PS backbone.

Attachment of Modalities to Nanoparticle Cores

Modalities associated with the invention, including agonists of nucleic acid-interacting complexes and antigens, can be attached to nanoparticle cores by any means known in the art. Methods for attaching oligonucleotides to nanoparticles are described in detail in and incorporated by reference from US Patent Publication No. 2010/0129808.

A nanoparticle can be functionalized in order to attach a polynucleotide. Alternatively or additionally, the polynucleotide can be functionalized. One mechanism for functionalization is the alkanethiol method, whereby oligonucleotides are functionalized with alkanethiols at their 3' or 5' termini prior to attachment to gold nanoparticles or nanoparticles comprising other metals, semiconductors or magnetic materials. Such methods are described, for example Whitesides, Proceedings of the Robert A. Welch Foundation 39th Conference On Chemical Research Nanophase Chemistry, Houston, Tex., pages 109-121 (1995), and Mucic et al. Chem. Commun. 555-557 (1996). Oligonucleotides can also be attached to nanoparticles using other functional groups such as phosphorothioate groups, as described in and incorporated by reference from U.S. Pat. No. 5,472,881, or substituted alkylsiloxanes, as described in and incorporated by reference from Burwell, Chemical Technology, 4, 370-377 (1974) and Matteucci and Caruthers, J. Am. Chem. Soc., 103, 3185-3191 (1981). In some instances, polynucleotides are attached to nanoparticles by terminating the polynucleotide with a 5' or 3' thionucleoside. In other instances, an aging process is used to attach polynucleotides to nanoparticles as described in and incorporated by reference from U.S. Pat. Nos. 6,361,944, 6,506,569, 6,767,702 and 6,750,016 and PCT Publication Nos. WO 1998/004740, WO 2001/000876, WO 2001/051665 and WO 2001/073123.

In some instances, the nucleic acid and/or antigen are covalently attached to the nanoparticle core, such as through a gold-thiol linkage. A spacer sequence can be included between the attachment site and the uptake control moiety and/or the binding moiety. In some embodiments, a spacer sequence comprises or consists of an oligonucleotide, a peptide, a polymer or an oligoethylene.

Nanoscale constructs can be designed with multiple chemistries. For example, a DTPA (dithiol phosphoramidite) linkage can be used. The DTPA resists intracellular release of flares by thiols and can serve to increase signal to noise ratio.

The conjugates produced by the methods described herein are considerably more stable than those produced by other methods. This increased stability is due to the increased density of the oligonucleotides on the surfaces of a nanoparticle core or forming the surface of the corona. By performing the salt additions in the presence of a surfactant, for example approximately 0.01% sodium dodecylsulfate (SDS), Tween, or polyethylene glycol (PEG), the salt aging process can be performed in about an hour.

The surface density may depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically. Generally, a surface density of at least 10 picomoles/cm will be adequate to provide stable nanoparticle-oligonucleotide conjugates. Preferably, the surface density is at least 15 picomoles/cm. Since the ability of the oligonucleotides of the conjugates to hybridize with targets may be diminished if the surface density is too great, the surface density optionally is no greater than about 35-40 picomoles/cm$^2$. Methods are also provided wherein the oligonucleotide is bound to the nanoparticle at a surface density of at least 10 pmol/cm$^2$, at least 15 pmol/cm$^2$, at least 20 pmol/cm$^2$, at least 25 pmol/cm$^2$, at least 30 pmol/cm$^2$, at least 35 pmol/cm$^2$, at least 40 pmol/cm$^2$, at least 45 pmol/cm, at least 50 pmol/cm$^2$, or 50 pmol/cm$^2$ or more.

Therapeutics

Aspects of the invention relate to delivery of nanoscale constructs to a subject for therapeutic and/or diagnostic use. The particles may be administered alone or in any appropriate pharmaceutical carrier, such as a liquid, for example saline, or a powder, for administration in vivo. They can also be co-delivered with larger carrier particles or within administration devices. The particles may be formulated. The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients. In some embodiments, nanoscale constructs associated with the invention are mixed with a substance such as a lotion (for example, aquaphor) and are administered to the skin of a subject, whereby the nanoscale constructs are delivered through the skin of the subject. It should be appreciated that any method of delivery of nanoparticles known in the art may be compatible with aspects of the invention.

For use in therapy, an effective amount of the particles can be administered to a subject by any mode that delivers the particles to the desired cell. Administering pharmaceutical compositions may be accomplished by any means known to the skilled artisan. Routes of administration include but are not limited to oral, parenteral, intramuscular, intravenous, subcutaneous, mucosal, intranasal, sublingual, intratracheal, inhalation, ocular, vaginal, dermal, rectal, and by direct injection.

Thus, the invention in one aspect involves the finding that agonists of nucleic acid-interacting complexes are highly effective in mediating immune stimulatory effects. These agonists of nucleic acid-interacting complexes are useful therapeutically and prophylactically for stimulating the immune system to treat cancer, infectious diseases, allergy, asthma, autoimmune disease, and other disorders and to help protect against opportunistic infections following cancer chemotherapy. The strong yet balanced, cellular and humoral immune responses that result from, for example, TLR agonist stimulation reflect the body's own natural defense system against invading pathogens and cancerous cells.

Thus the agonists of nucleic acid-interacting complexes useful in some aspects of the invention as a vaccine for the treatment of a subject at risk of developing or a subject having allergy or asthma, an infection with an infectious organism or a cancer in which a specific cancer antigen has been identified. The agonists of nucleic acid-interacting complexes can also be given without the antigen or allergen for protection against infection, allergy or cancer, and in this case repeated doses may allow longer term protection. A subject at risk as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, i.e., during pollen season, then that subject is at risk of exposure to the antigen.

A subject having an infection is a subject that has been exposed to an infectious pathogen and has acute or chronic detectable levels of the pathogen in the body. The CpG immunostimulatory oligonucleotides can be used with or without an antigen to mount an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

A subject having an allergy is a subject that has or is at risk of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

A subject shall mean a human or vertebrate animal including but not limited to a dog, cat, horse, cow, pig, sheep, goat, turkey, chicken, primate, e.g., monkey, and fish (aquaculture species), e.g. salmon. Thus, the invention can also be used to treat cancer and tumors, infections, and allergy/asthma in non human subjects.

As used herein, the term treat, treated, or treating when used with respect to an disorder such as an infectious disease, cancer, allergy, or asthma refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites and allergens. The term antigen broadly includes any type of molecule which is recognized by a host immune system as being foreign. Antigens include but are not limited to cancer antigens, microbial antigens, and allergens.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. A cancer antigen is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research*, 54:1055, by partially purifying the antigens, by recombinant technology, or by de novo synthesis of known antigens.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of viruses that have been found in humans include but are not limited to: *Retroviridae* (e.g. human immunodeficiency viruses, such as HIV-1 (also referred to as HDTV-III, LAVE or HTLV-III/LAV, or HIV-III; and other isolates, such as HIV-LP; *Picornaviridae*(e.g. polio viruses, hepatitis A virus; enteroviruses, human Coxsackie viruses, rhinoviruses, echoviruses); *Calciviridae* (e.g. strains that cause gastroenteritis); *Togaviridae* (e.g. equine encephalitis viruses, rubella viruses); *Flaviridae* (e.g. dengue viruses, encephalitis viruses, yellow fever viruses); *Coronoviridae* (e.g. coronaviruses); *Rhabdoviradae* (e.g. vesicular stomatitis viruses, rabies viruses); Filoviridae (e.g. ebola viruses); *Paramyxoviridae* (e.g. parainfluenza viruses, mumps virus, measles virus, respiratory syncytial virus); *Orthomyxoviridae* (e.g. influenza viruses); *Bungaviridae* (e.g. Hantaan viruses, bunga viruses, phleboviruses and Nairo viruses); Arena viridae (hemorrhagic fever viruses); *Reoviridae* (e.g. reoviruses, orbiviurses and rotaviruses); *Birnaviridae; Hepadnaviridae* (Hepatitis B virus); *Parvovirida* (parvoviruses); *Papovaviridae* (papilloma viruses, polyoma viruses); *Adenoviridae*(most adenoviruses); *Herpesviridae* (herpes simplex virus (HSV) 1 and 2, varicella zoster virus, cytomegalovirus (CMV), herpes virus; *Poxviridae* (variola viruses, vaccinia viruses, pox viruses); and *Iridoviridae* (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to, *Pasteurella* species, Staphylococci species, and *Streptococcus* species. Gram negative bacteria include, but are not limited to, *Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelli*.

Examples of fungi include *Cryptococcus neoformans, Histoplasma capsulatum, Coccidioides immitis, Blastomyces dermatitidis, Chlamydia trachomatis, Candida albicans*. Other infectious organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see C. G. A Thomas, *Medical Microbiology*, Bailliere Tindall, Great Britain 1983, the entire contents of which is hereby incorporated by reference.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: Canine (*Canis familiaris*); *Dermatophagoides* (e.g. *Dermatophagoides farinae*); *Felis* (*Felis domesticus*); *Ambrosia* (*Ambrosia artemiisfolia; Lolium* (e.g. *Lolium perenne* or *Lolium multiflorum*); *Cryptomeria* (*Cryptomeria japonica*); *Alternaria* (*Alternaria alternata*); Alder; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum*(e.g. *Sorghum halepensis*); and *Bromus* (e.g. *Bromus inermis*).

The nanoscale constructs of the invention may also be coated with or administered in conjunction with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that nonspecific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

The constructs of the invention may also be administered in conjunction with a therapeutic or diagnostic antibody. In one embodiment, the antibody may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab, rituxan, bevacizumab, and ImmuRAIT-CEA.

The agonists of nucleic acid-interacting complexes are also useful for treating and preventing autoimmune disease. Autoimmune disease is a class of diseases in which an subject's own antibodies react with host tissue or in which immune effector T cells are autoreactive to endogenous self peptides and cause destruction of tissue. Thus an immune response is mounted against a subject's own antigens, referred to as self antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to the destruction of the tumor or cancer. Thus, in some aspects of the invention aimed at treating autoimmune disorders it is not recommended that the CpG immunostimulatory nucleic acids be administered with self antigens, particularly those that are the targets of the autoimmune disorder.

In other instances, the CpG immunostimulatory nucleic acids may be delivered with low doses of self-antigens. A number of animal studies have demonstrated that mucosal administration of low doses of antigen can result in a state of immune hyporesponsiveness or "tolerance." The active mechanism appears to be a cytokine-mediated immune deviation away from a Th1 towards a predominantly Th2 and Th3 (i.e., TGF-β dominated) response. The active suppression with low dose antigen delivery can also suppress an unrelated immune response (bystander suppression) which is of considerable interest in the therapy of autoimmune diseases, for example, rheumatoid arthritis and SLE. Bystander suppression involves the secretion of Th1-counter-regulatory, suppressor cytokines in the local environment where proinflammatory and Th1 cytokines are released in either an antigen-specific or antigen-nonspecific manner. "Tolerance" as used herein is used to refer to this phenomenon. Indeed, oral tolerance has been effective in the treatment of a number of autoimmune diseases in animals including: experimental autoimmune encephalomyelitis (EAE), experimental autoimmune myasthenia gravis, collagen-induced arthritis (CIA), and insulin-dependent diabetes mellitus. In these models, the prevention and suppression of autoimmune disease is associated with a shift in antigen-specific humoral and cellular responses from a Th1 to Th2/Th3 response.

In another aspect, the present invention is directed to a kit including one or more of the compositions previously discussed. A "kit," as used herein, typically defines a package or an assembly including one or more of the compositions of the invention, and/or other compositions associated with the invention, for example, as previously described. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions that may be associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

In some embodiments, a kit associated with the invention includes one or more nanoparticle cores, such as a nanoparticle core that comprises gold. A kit can also include one or more agonists of nucleic acid-interacting complexes. A kit can also include one or more antigens.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the use of the compositions, for example, for a particular use, e.g., to a sample. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein. As used herein, "promoting" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or subcontractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1

Materials and Methods

Synthesis of Immunostimulatory SNAs

Synthesis of immunostimulatory SNAs (isSNA) is achieved as described elsewhere[7-12] with the following essential modifications. In brief, 20 mL 13 nm gold colloid is mixed with 10% Tween 20 and TLR agonist sequence of sulfhydryl-modified nucleic acid (TLR 3, 7/8, 9) at appropriate concentration, such as 5 uM and allowed to react overnight. Addition of antigen can be achieved similar to methods as described elsewhere.[10] Purification of SNAs can be achieved by repeated ultracentrifugation at 75,000×g for 30 min.

Cell Lines

RAW 264.7 cell lines were obtained from ATCC. RAW-Blue macrophages were obtained from InVivoGen. Ramos-Blue and THP1-XBlue cells were obtained from InVivoGen. All were cultured according to the distributor recommendations.

Results and Discussion

It was found that the nanoscale constructs of the invention markedly enhance potency in macrophages over unformulated agonists of nucleic acid-interacting complexes (CpG oligonucleotides) in solution (FIG. 2). RAW-Blue macrophages were plated at 65 k cells per well and allowed to adhere overnight. On the day of experiments, cells were treated with AST-008-ps or CpG 1826-ps at the indicated concentration of oligo for 30 min (top panel), 4 h (middle panel), or overnight (bottom panel). For 30 min and 4 h time points, the entire supernatant was aspirated, the cells were washed, and complete growth medium without test agents were administered. At the overnight time point, the activation state of the cells was determined using the QuantiBlue assay kit. The results show that particularly at short time points, AST-008-ps demonstrates a significantly lower EC50 than CpG 1826-ps of 188 nM as compared to 17800 nM (9-1000-fold reduction one standard deviation from the mean). At 4 h, AST-008-ps demonstrates a lower EC50 (32 nM vs 57 nm) and greater activation state than CpG 1826-ps. This difference became narrower following overnight incubation, at which point the EC50s were not statistically different from each other. This suggests that under conditions where residence time of the agent with the target cell is limited, particularly to 30 minutes or below, the AST-008-ps formulation may result in more rapid and robust immune activation.

Figure 3:
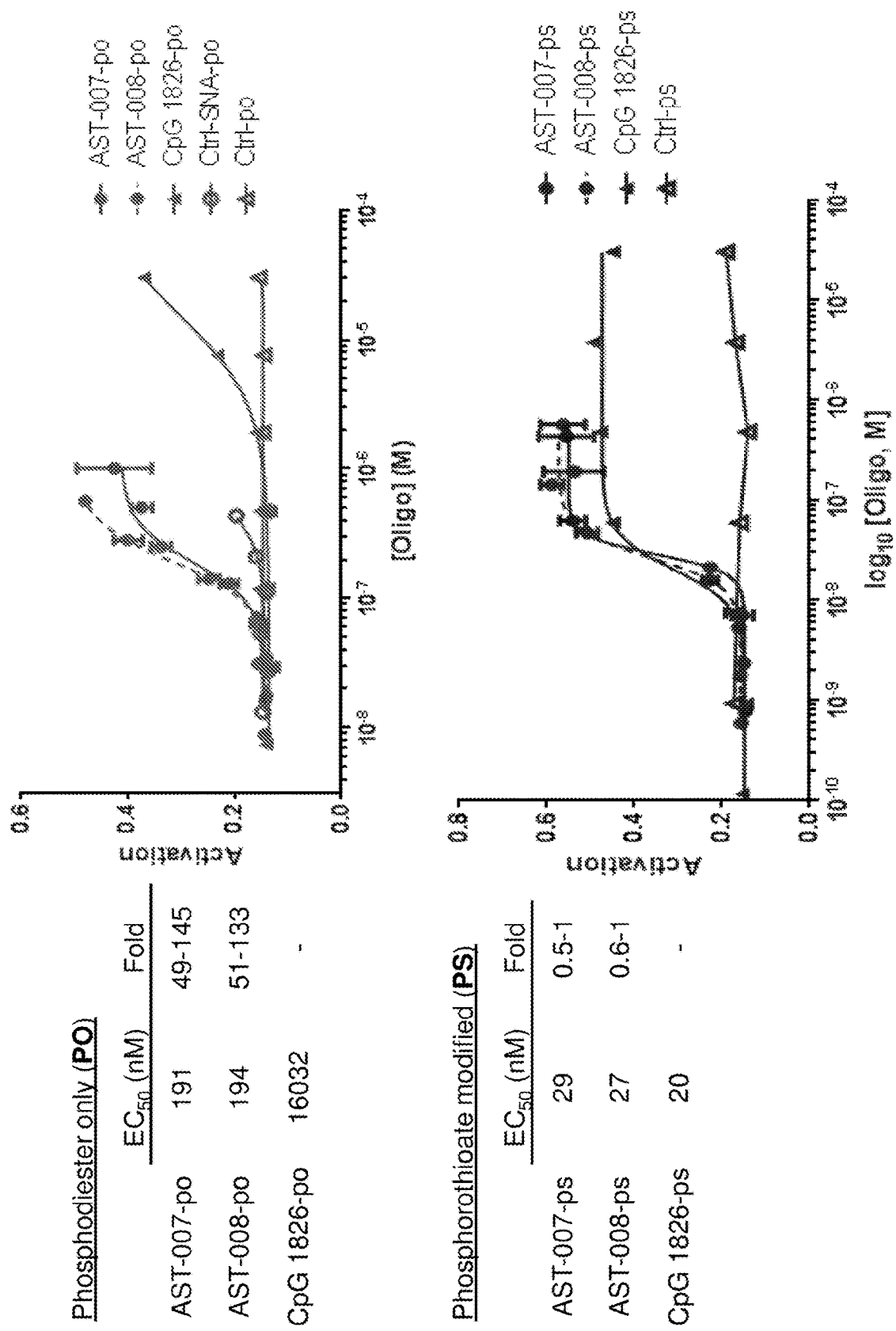
FIG. 3 is a set of graphs depicting markedly enhanced potency in macrophages of the nanoscale constructs of the invention over agonists of nucleic acid-interacting complexes (CpG oligonucleotides) in solution following overnight incubation.

It was also demonstrated that the nanoscale constructs of the invention markedly enhanced potency in macrophages over unformulated agonists of nucleic acid-interacting complexes (CpG oligonucleotides) in solution following overnight incubation (FIG. 3). RAW-Blue macrophages were plated at 65 k cells per well and allowed to adhere overnight. On the day of experiments, AST-007-po, AST-007-ps, AST-008-po, AST-008-ps, CpG 1826-po, CpG 1826-ps were incubated with the cells overnight. The degree of activation was then determined using the QuantiBlue assay kit. The results show that for compounds containing only phosphodiester (-po) linkages (top panel), AST-007-po and AST-008-po are ~50-150 fold more potent as determined by their EC50 values than CpG 1826-po (191 nM and 194 nM as compared to 16032 nM, respectively). With phosphorothioate-modified compounds (-ps, bottom panel), AST-007-ps and AST-008-ps are approximately equivalent to CpG 1826-ps, with an EC50 of 29 nM, 27 nM, and 20 nM, respectively.

Figure 4:
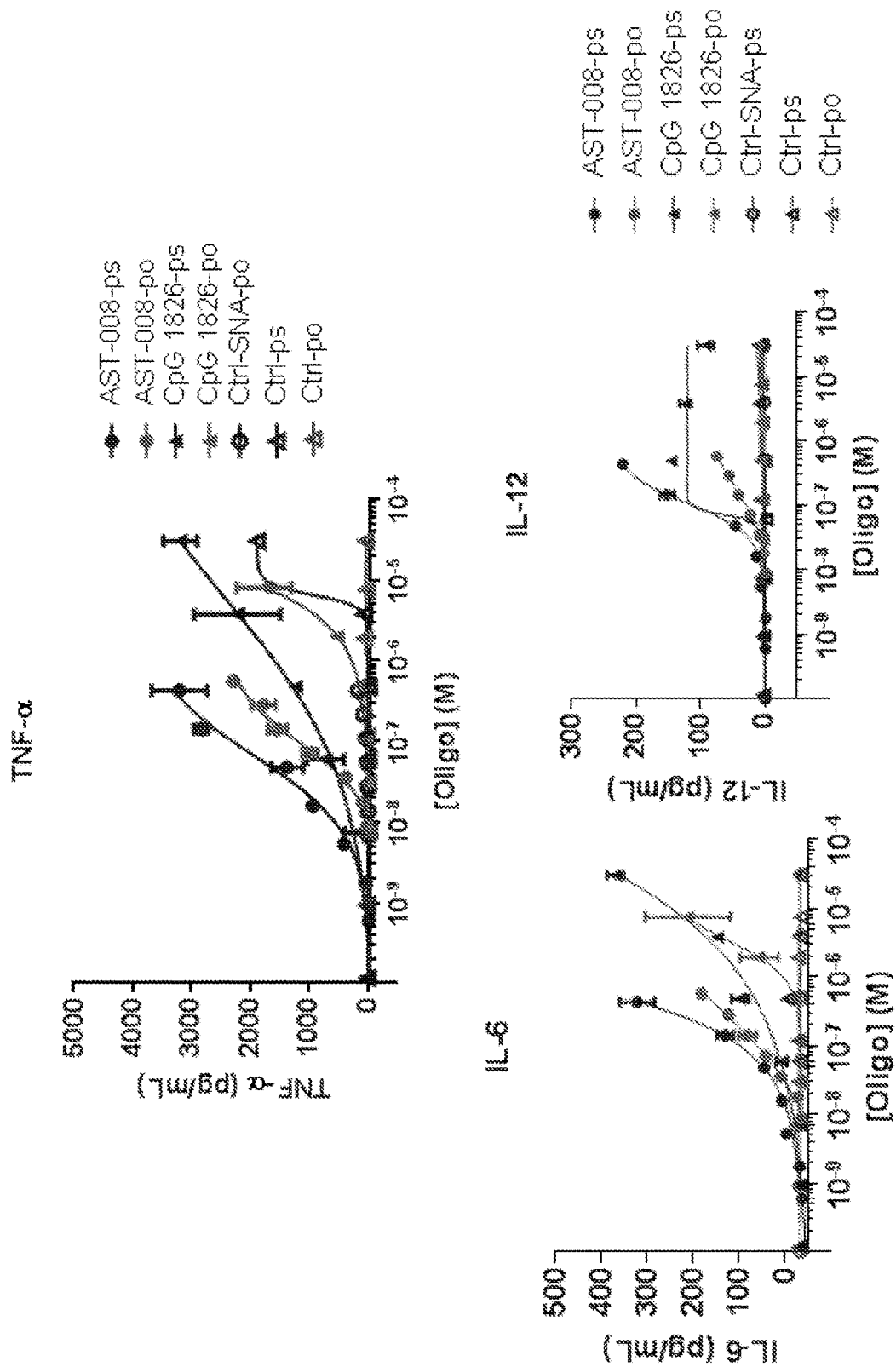
FIG. 4 is a set of graphs depicting an enhanced level of cytokine secretion with the nanoscale constructs of the invention over agonists of nucleic acid-interacting complexes (CpG oligonucleotides) in solution. The effect on cytokine induction was examined for both oligonucleotides having phosphodiester and phosphorothioate internucleotide linkages in both the nanoscale construct and the TRL agonist groups.

Levels of cytokine secretion following exposure to the nanoscale constructs of the invention versus unformulated agonists of nucleic acid-interacting complexes (CpG oligonucleotides) in solution was examined. The effect on cytokine induction was examined for both oligonucleotides having phosphodiester and phosphorothioate internucleotide linkages in both the nanoparticle and the TRL agonist groups (FIG. 4). RAW-Blue macrophages were plated at 65 k cells per well and allowed to adhere overnight. On the day of experiments, the indicated compounds were incubated with the cells overnight. The degree of cytokine secretion was determined by collecting the supernatant and measuring the concentration of the indicated cytokines by ELISA (TNF-alpha-top panel, IL-12-bottom right panel, IL-6-bottom left panel). The results show significantly higher cytokine secretion at lower doses are possible using AST-008-ps and AST-008-po than CpG 1826-ps, CpG 1826-po, and the indicated controls. For example, to achieve greater than 2000 pg/mL TNF-alpha, less than 100 nM AST-008-ps was needed and less than 1000 nM AST-007-po was needed, but greater than 1000 nM CpG 1826-ps was required.

Figure 5:
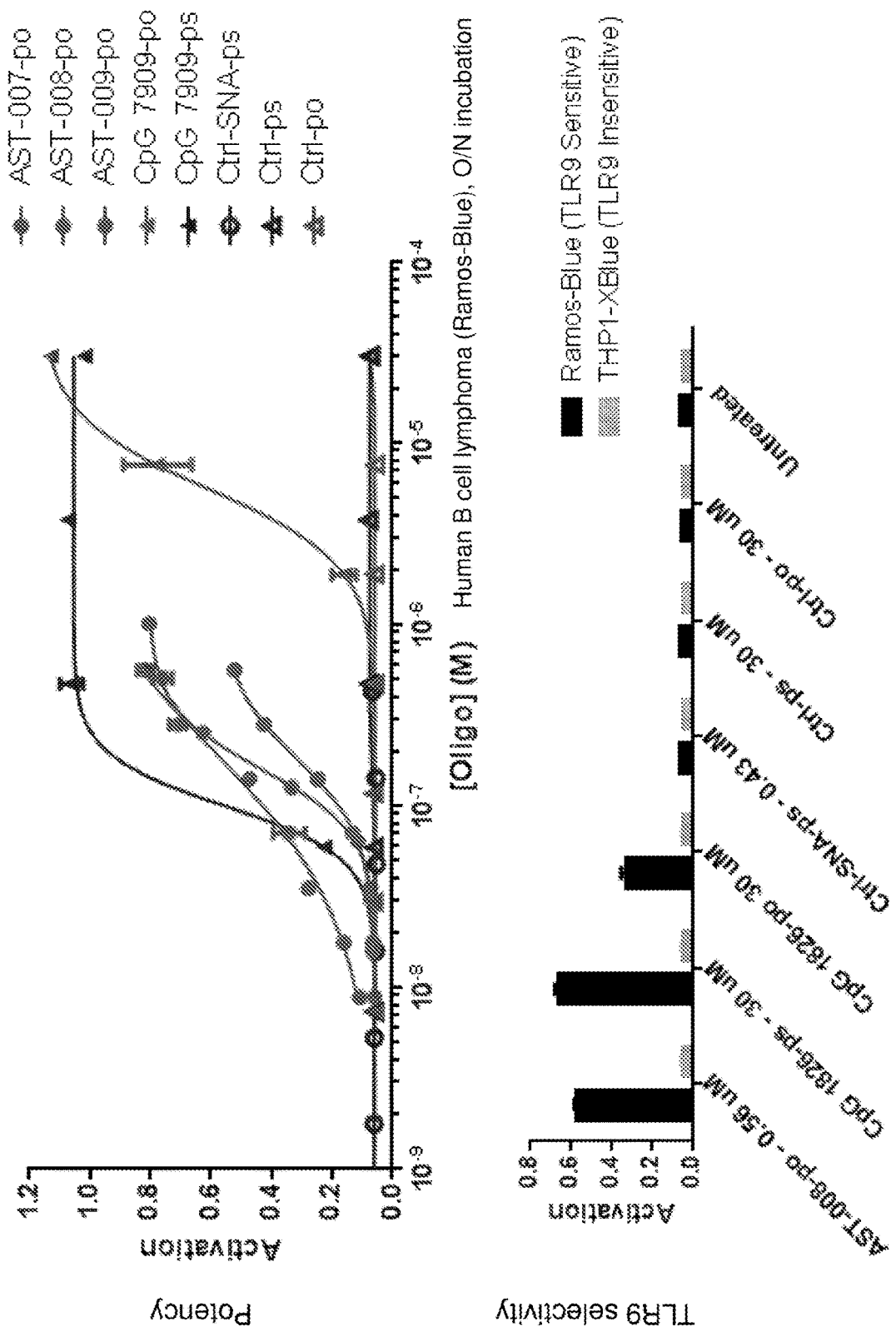
FIG. 5 is a line and bar graph depicting TLR9 activation in response to stimulation with a nanoscale construct of the invention having a phosphodiester CpG oligonucleotide in comparison with phosphodiester and phosphorothioate CpG oligonucleotides in solution.

Next, TLR9 activation in response to stimulation with a nanoscale of the invention having a phosphodiester CpG oligonucleotide in comparison with phosphodiester and phosphorothioate CpG oligonucleotides in solution was examined (FIG. 5). Ramos-Blue or THP1-XBlue cells were seeded and activated according to the manufacturer's recommended protocol using the indicated compounds and controls. Remarkably, AST-007-po, AST-008-po, and AST-009-po demonstrate comparable activation at similar doses than CpG 7909-ps, a known and optimized TLR 9 agonist. In addition, activation appeared to be dependent on TLR 9, as the TLR 9 agonist insensitive THP1-XBlue cells did not demonstrate any activation.

Figure 6:
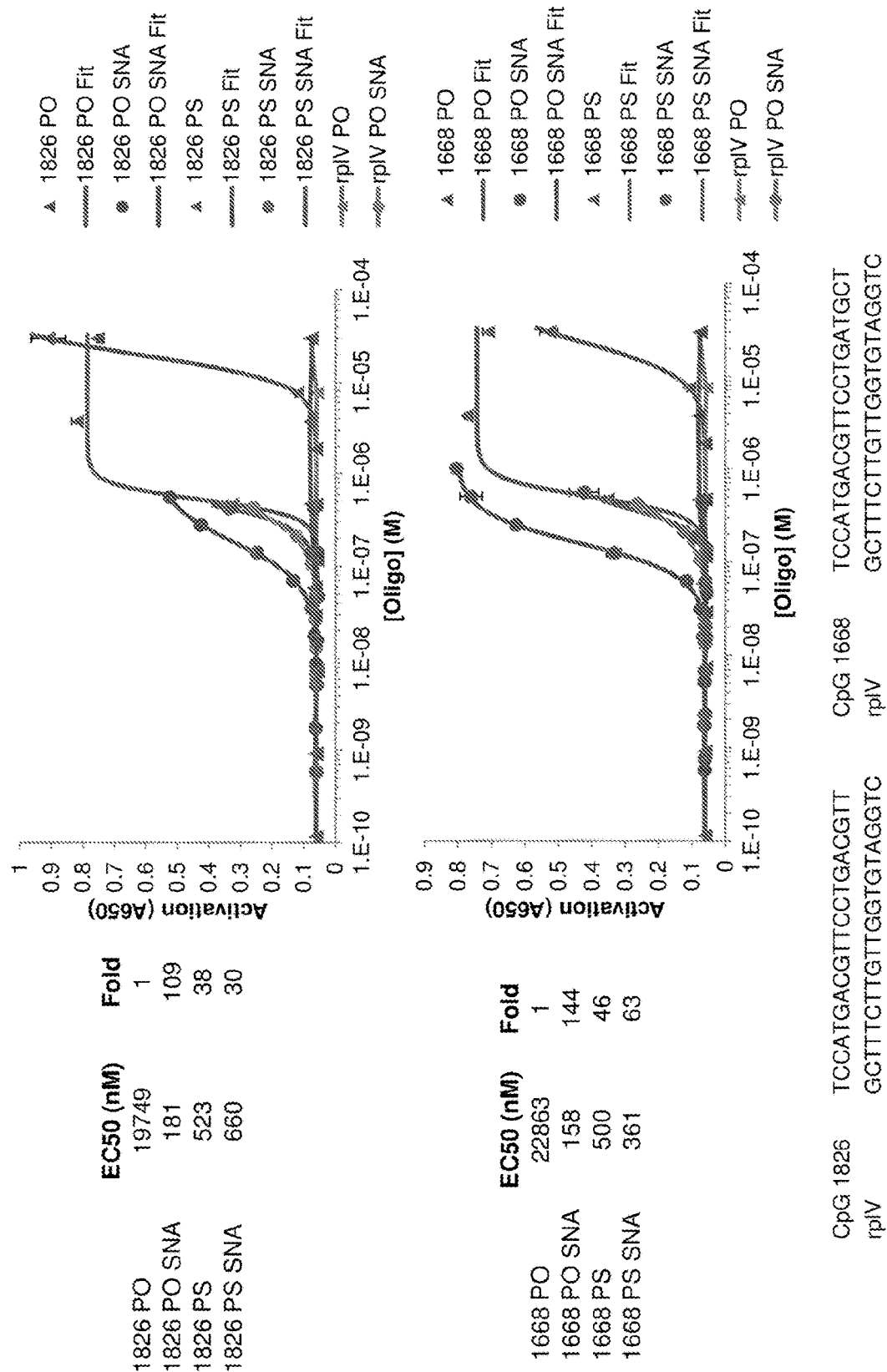
FIG. 6 is a set of graphs depicting multiple fold increase in potency of a nanoscale construct of the invention over several different CpG oligonucleotide sequences. CpG 1826 is SEQ ID NO: 1 and the rp1V below it is SEQ ID NO: 2. CpG 1668 is SEQ ID NO: 3 and the rp1V below it is SEQ ID NO: 4.

It was determined that a nanoscale construct of the invention had a multiple fold increase in potency of over several different CpG oligo sequences (FIG. 6). Ramos-Blue cells were seeded and activated according to the manufacturer's recommended protocol using the indicated compounds and controls. Oligo 1826 (top panel) and 1668 (bottom panel) were tested. Notably, SNA compounds demonstrate significantly lower EC50 values than free oligos, independent of chemistry, as compared to controls. This suggests that for these sequences, the SNA formulation of oligos is several fold more potent.

Figure 7:
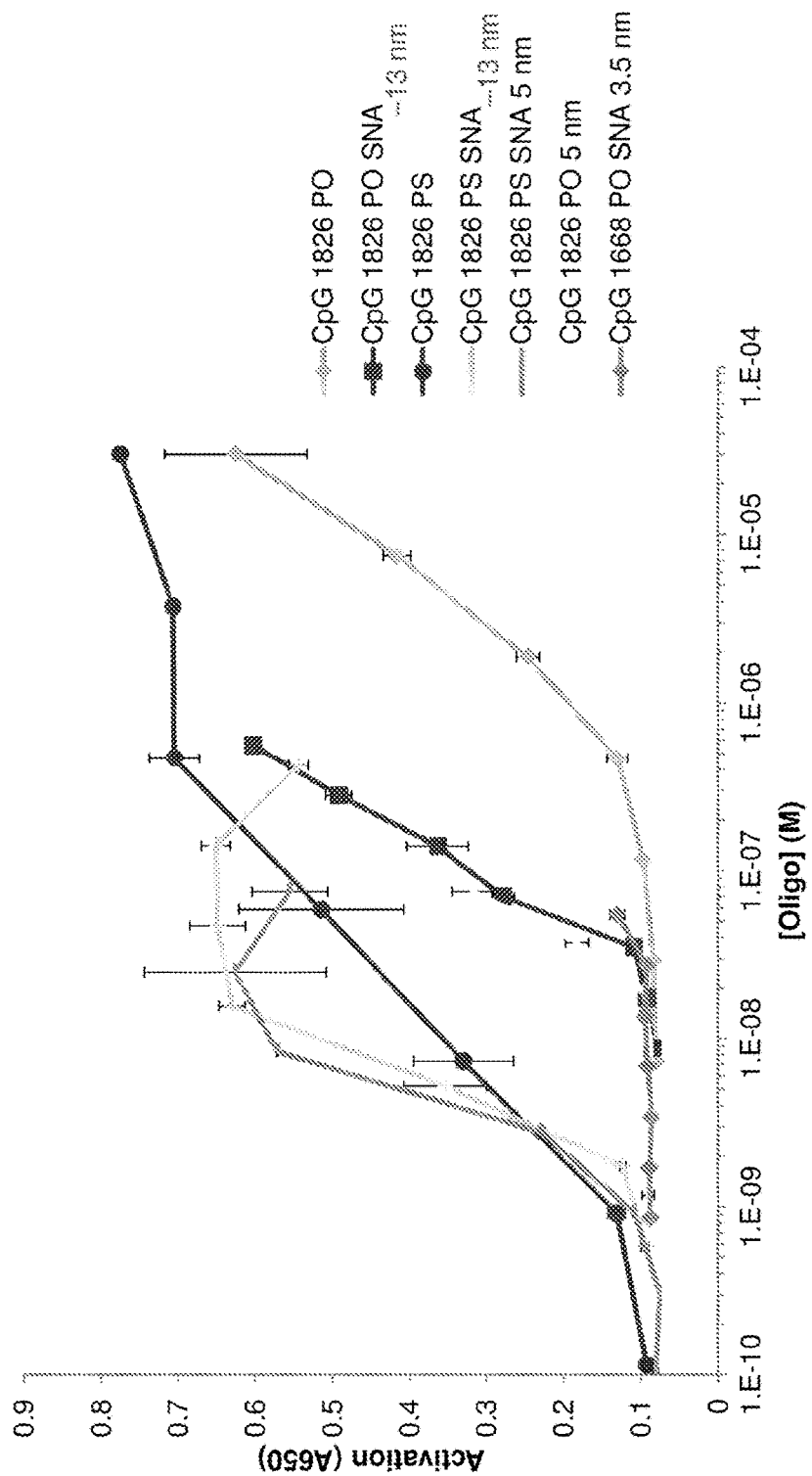
FIG. 7 is a set of graphs depicting the effects of modulating nanoscale construct core size suggests on the enhancement of agonist activity.
Figure 7:
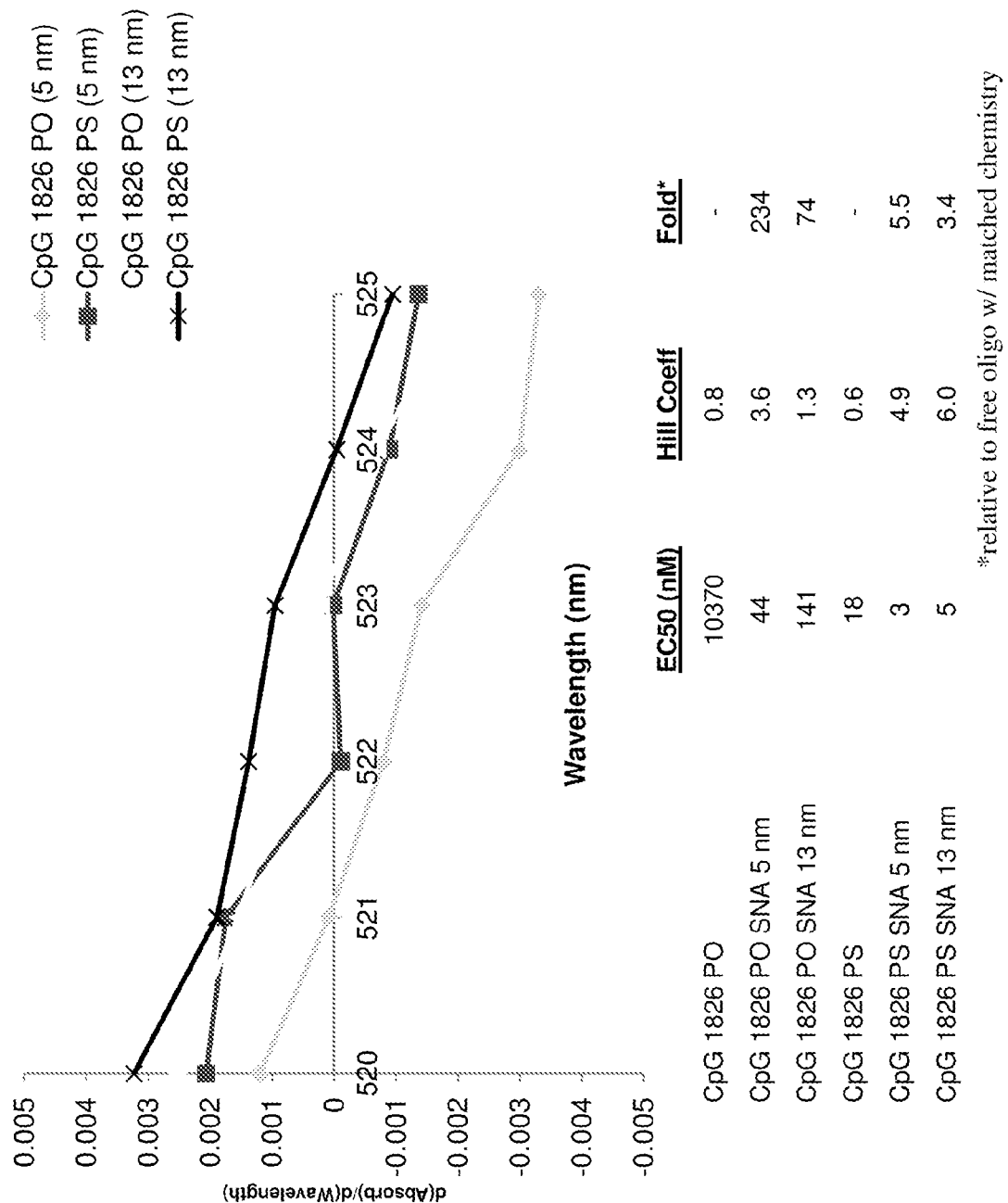

The effects of modulating nanoparticle core size was examined (FIG. 7). Raw Blue cells were plated and treated with the indicated agonists with different gold core sizes, ranging from 3.5 nm to 13 nm using the indicated oligos. The results show that smaller gold core sizes appear to demonstrate the potential to enhance agonist activity in vitro.

Figure 8:
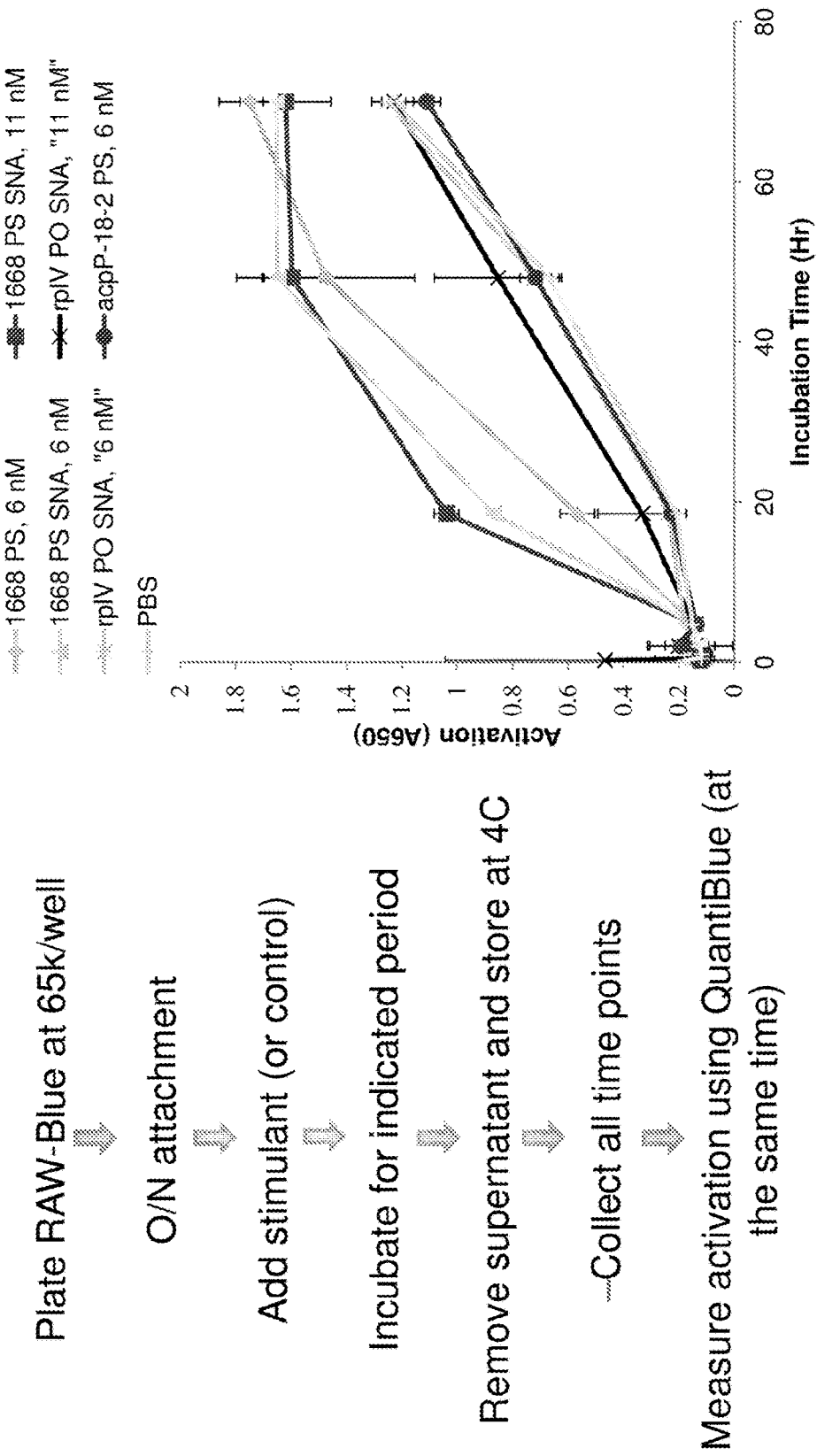
FIG. 8 shows a graph depicting more rapid and sustained activation than CpG oligonucleotide.

The nanoscale constructs of the invention were observed to have a more rapid and sustained activation than CpG oligo (FIG. 8). Cells were plated as described and activation was measured using QuantiBlue. The results show that at 6 nM oligo, the PS SNAs demonstrate significantly more activation than free 1668 PS oligos.

Figure 9:
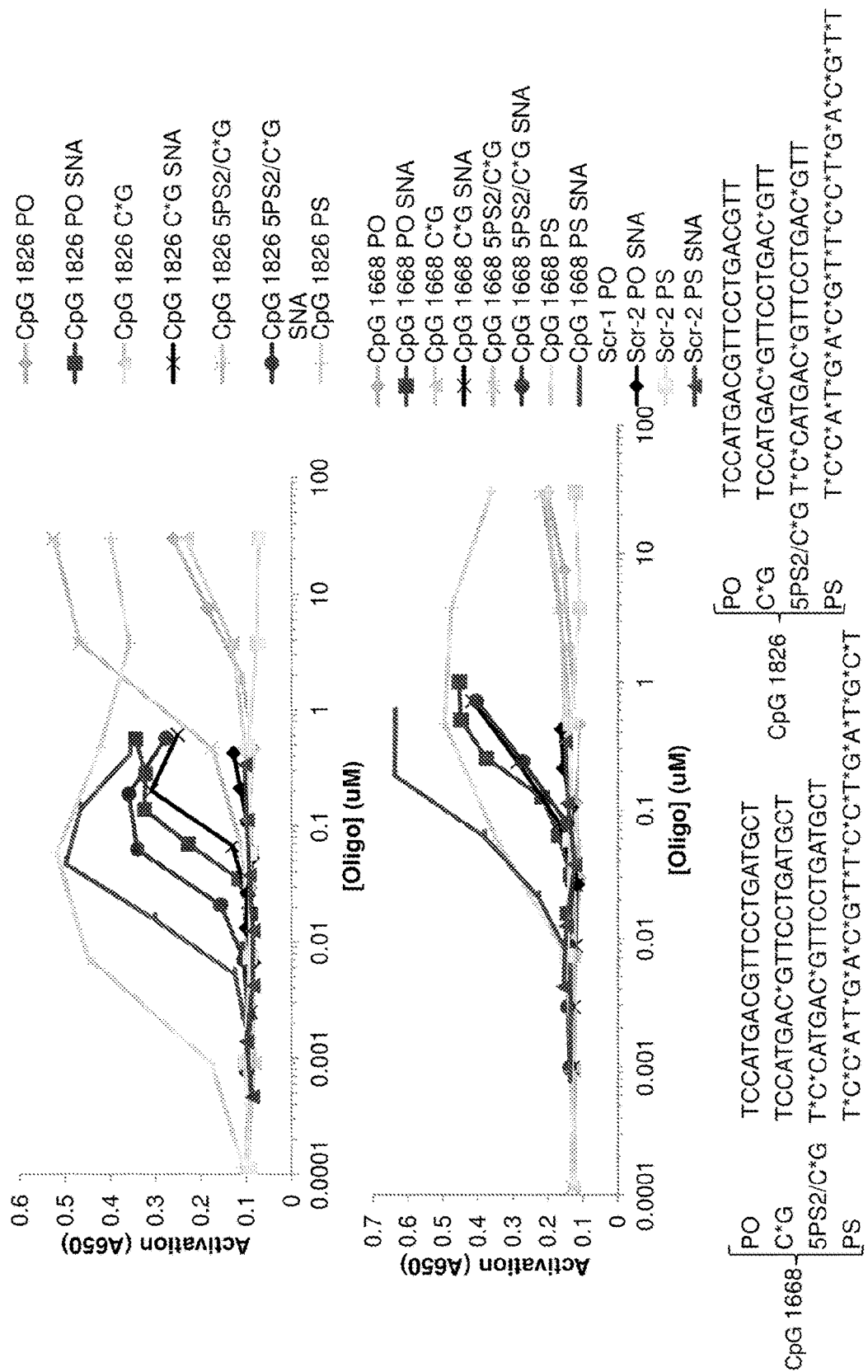
FIG. 9 is a set of graphs depicting the ability of phosphorothioate modifications to modulate agonist activity in a sequence-dependent manner. For CpG 1668: PO is SEQ ID NO: 5, C*G is SEQ ID NO: 6, 5PS2/C*G is SEQ ID NO: 7, and PS is SEQ ID NO: 8. For CpG 1826: PO is SEQ ID NO: 9, C*G is SEQ ID NO: 10, 5PS2/C*G is SEQ ID NO: 11, and PS is SEQ ID NO: 12.

The ability of phosphorothioate modifications to modulate agonist activity in a sequence-dependent manner was examined (FIG. 9). Raw Blue cells were plated and treated with the indicated agonists. Oligo 1826 (top panel) and 1668 (bottom panel) were tested. The results show that internal phosphorothioate modifications (C*G) and two 5' phosphorothioate linkages (5'PS2) have an effect on the activity of immunostimulatory SNAs that appears to be sequence dependent.

Figure 10:
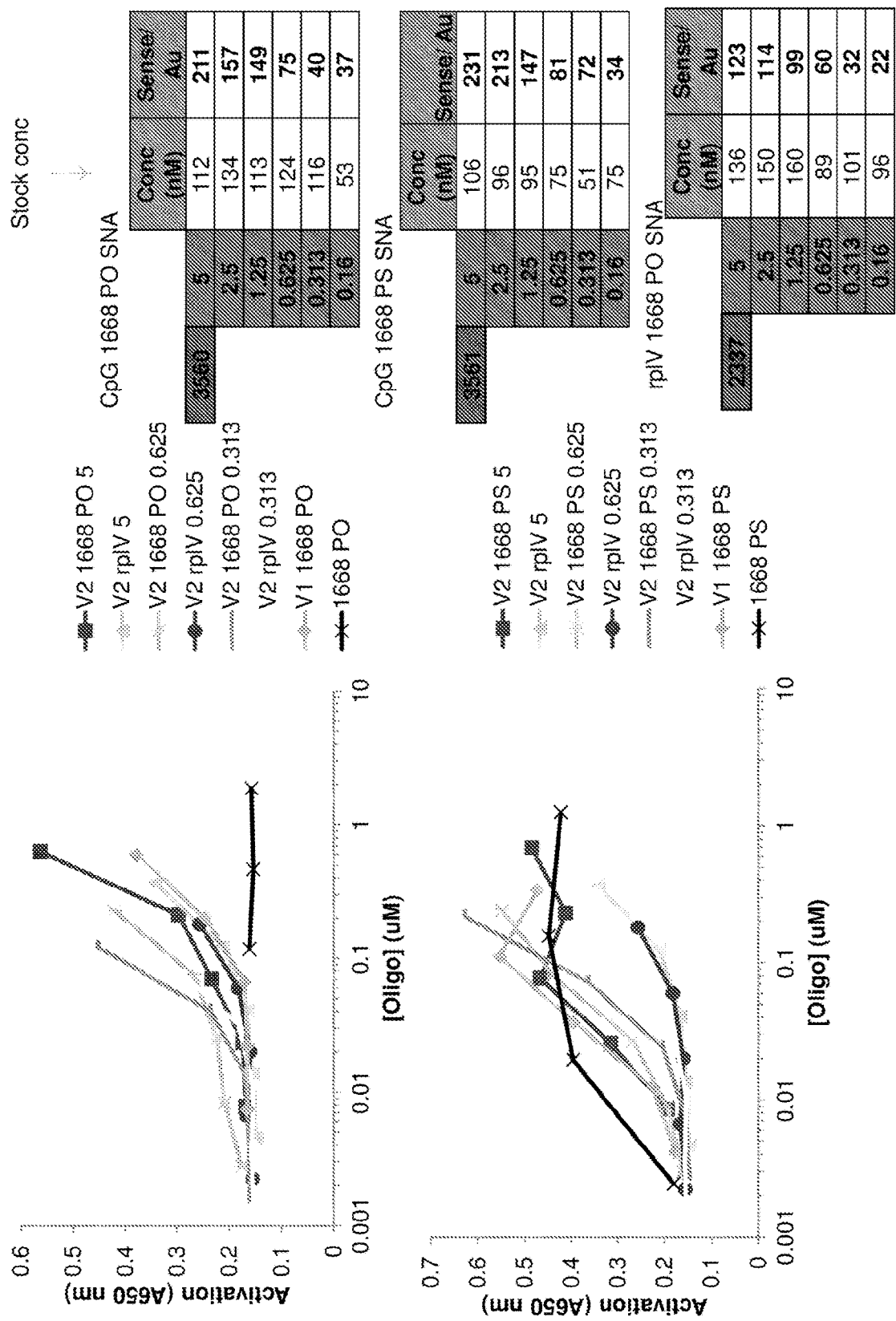
FIG. 10 is a set of graphs depicting the ability of oligonucleotide loading density to affect agonist activity.

The ability of oligonucleotide loading density to affect agonist activity was assessed (FIG. 10). V2 indicates that the construct was completely gold coated prior to oligo addition to the gold core. Phosphodiester oligonucleotides (top panel) and phosphorothioate oligonucleotides (bottom panel) were tested. The data shows that the density of oligonucleotide on the surface of the gold will modulate the activity of the immunostimulatory construct.

Figure 11:
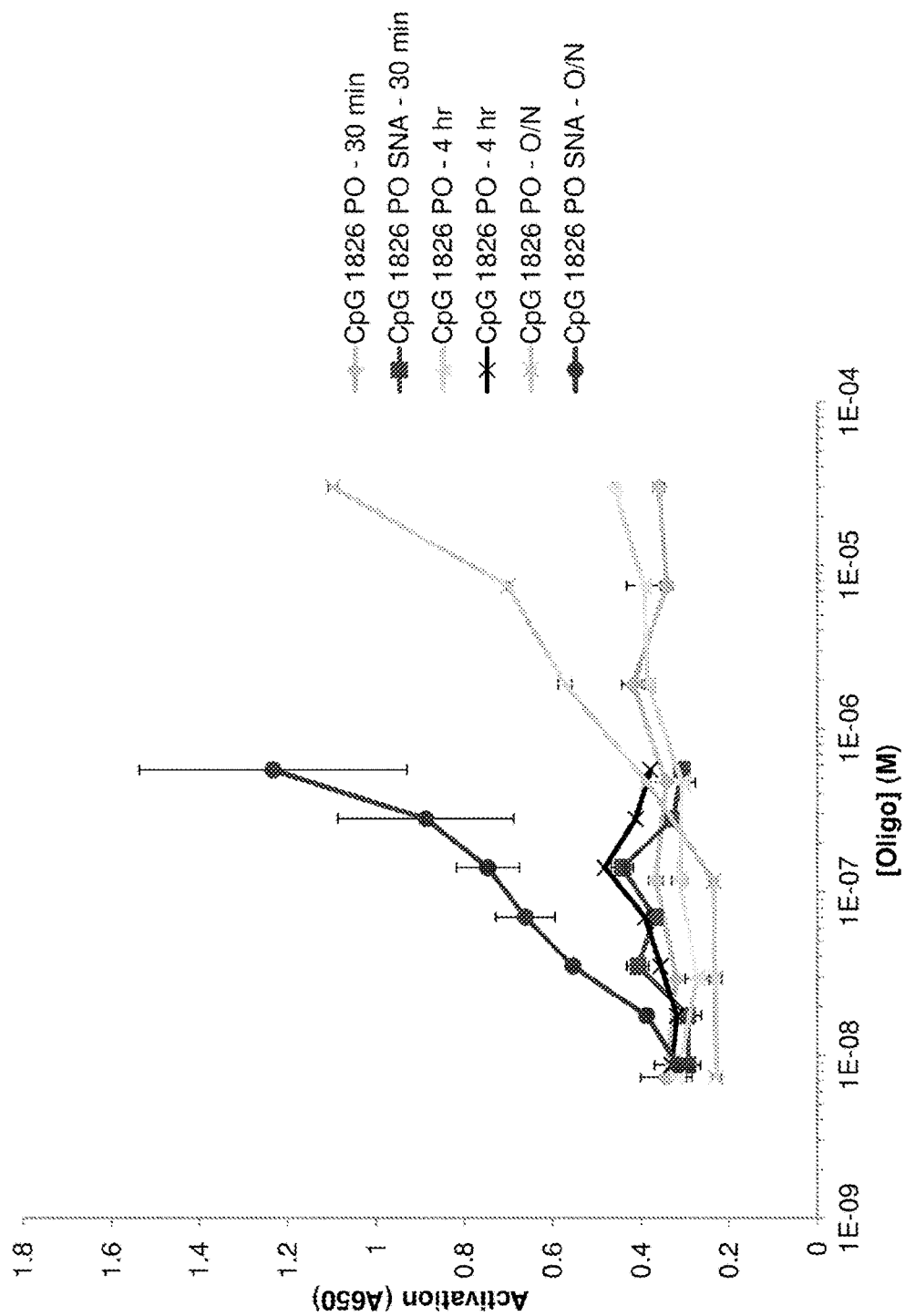
FIG. 11 shows a graph depicting a time course of activation of CpG PO/PO nanoscale constructs. The tested constructs are not activated until >4 hr of incubation.

A time course of activation of CpG PO/PO nanoscale constructs was studied (FIG. 11). The tested constructs are not activated until >4 hr of incubation. Raw Blue cells were plated and treated with the indicated agonists. The results show that PO and PO SNAs do not robustly activate adherent RAW Blue cells until greater than 4 hours of incubation.

Figure 12:
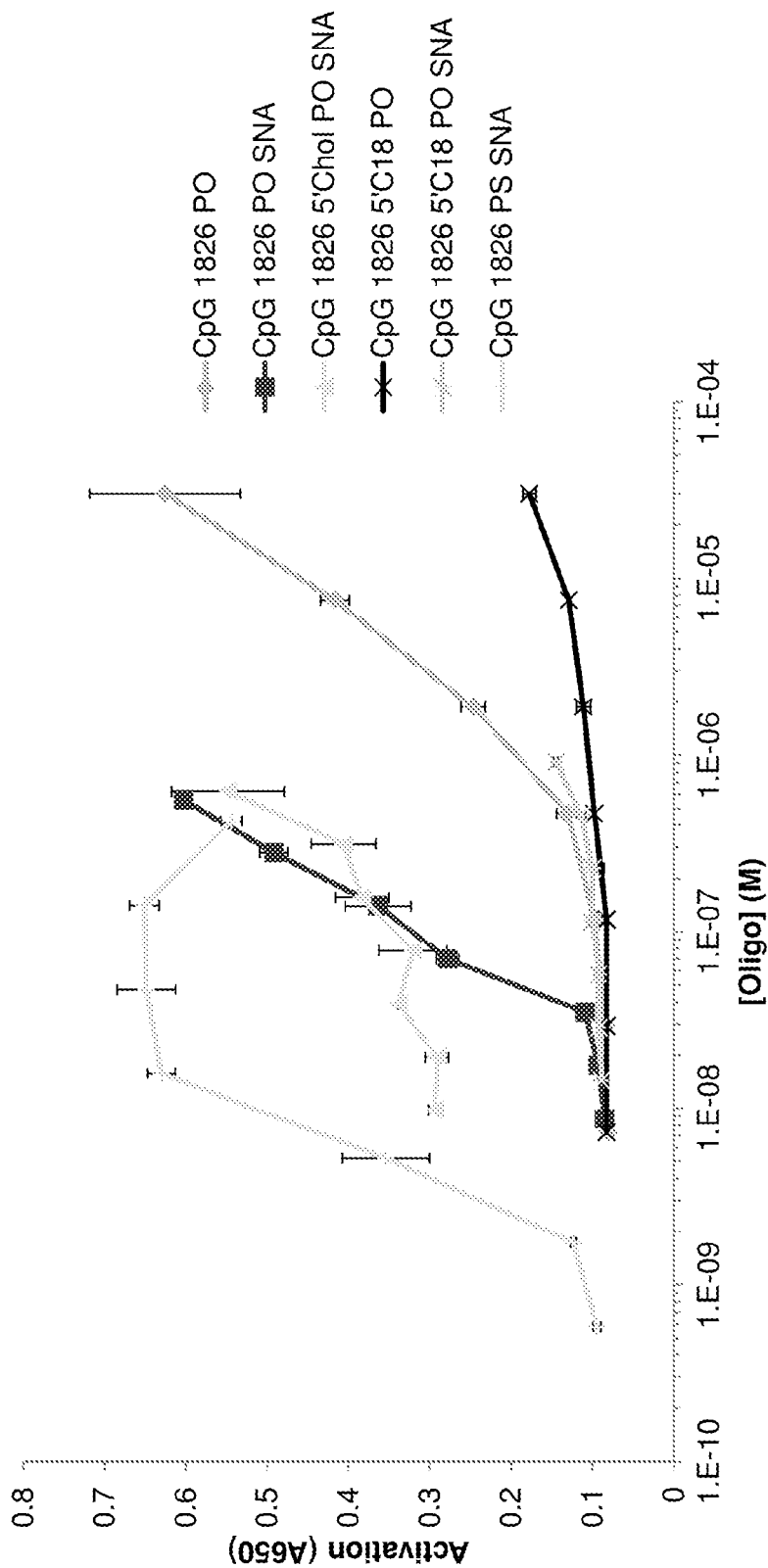
FIG. 12 shows a graph demonstrating that 5'Chol CpG PO nanoscale constructs show activation in low nM range, and 5'C18 abrogated the activity.

5'Chol CpG PO nanoscale constructs showed activation in low nM range, while 5'C18 abrogated the activity (FIG. 12). A 5' cholesterol modification (5'Chol) may increase the potency of the agonist, particularly at low concentrations in a oligo-dose-independent manner. Modification of the 5' end with a C18 molecule (5'C18) appears to eliminate the activity altogether.

Figure 13:
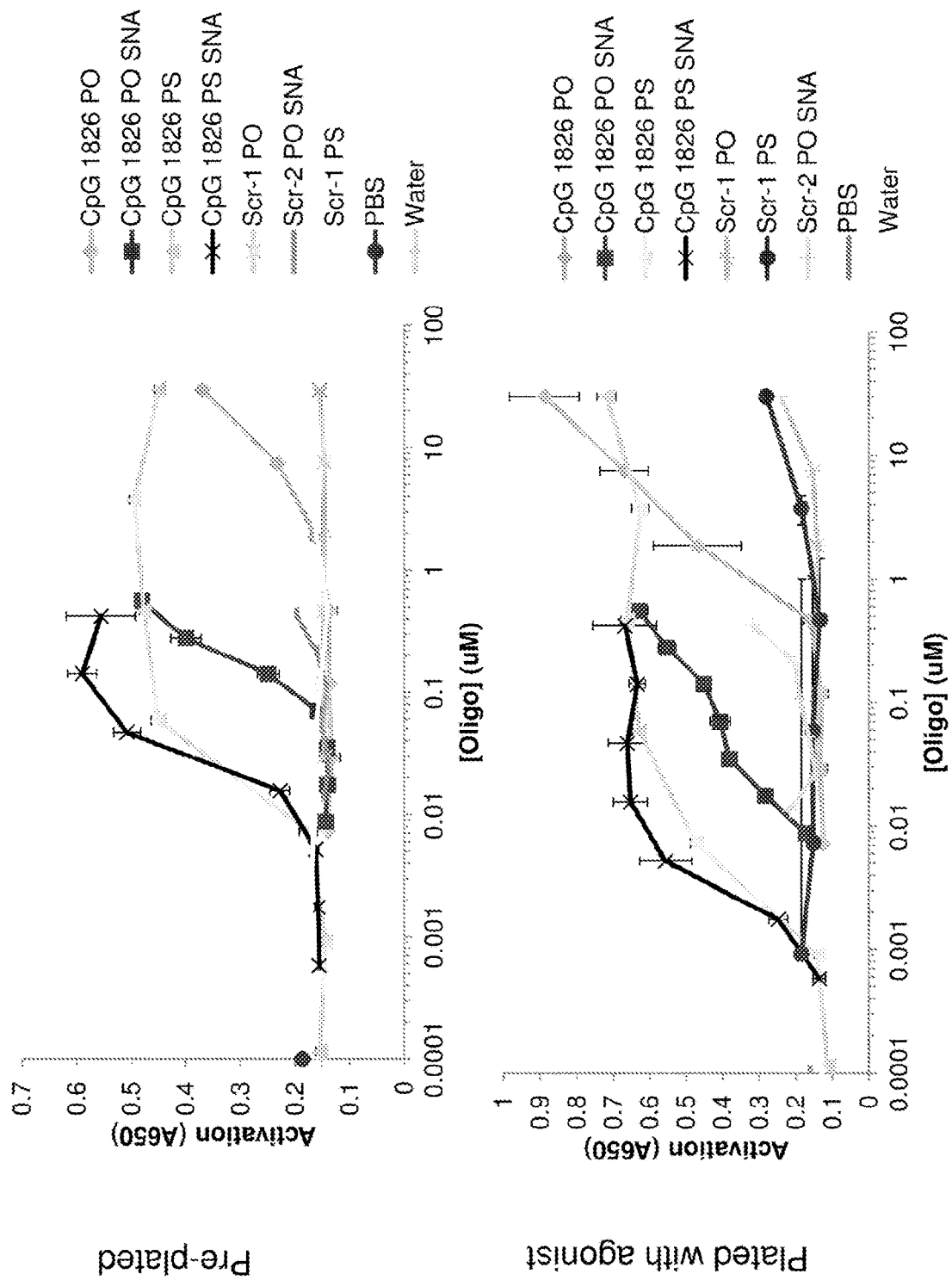
FIG. 13 is a set of graphs demonstrating that pre-plated macrophages are more primed for subsequent activation.

Pre-plated macrophages are more primed for subsequent activation (FIG. 13). RAW Blue macrophages that were plated overnight prior to addition of the agonist compounds (top) generally demonstrate greater activation than when the cells are plated at the same time as the agonist compound is added (bottom).

Figure 14:
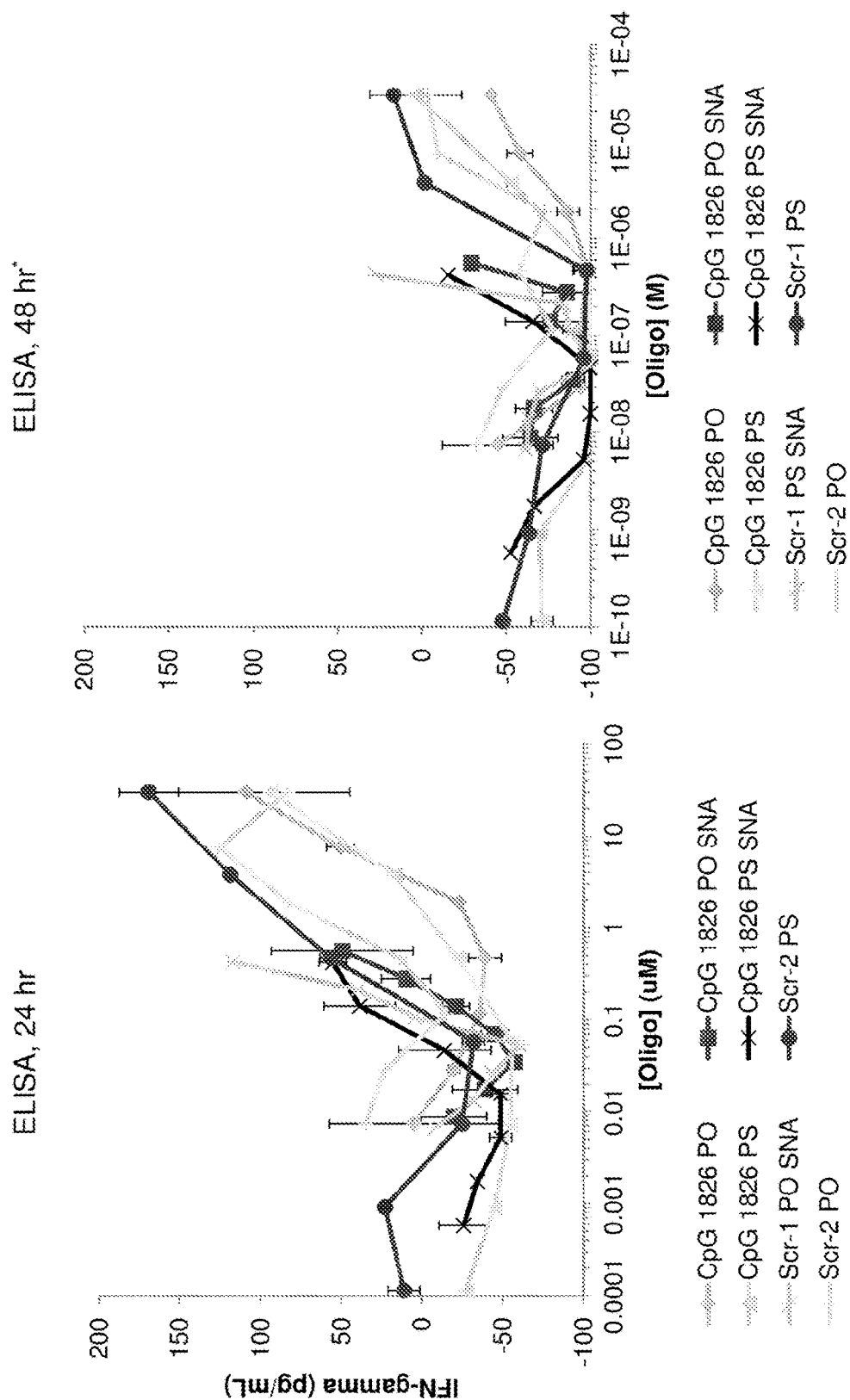
FIG. 14 is a set of graphs demonstrating low levels of IFN-gamma secretion by macrophages.

It was demonstrated that low levels of IFN-gamma secretion by macrophages (FIG. 14). RAW-Blue macrophages were plated at 65 k cells per well and allowed to adhere overnight. On the day of experiments, the indicated compounds were incubated with the cells overnight. The degree of cytokine secretion (either 24 hours-left panel or 48 hours-right panel after treatment) was determined by collecting the supernatant and measuring the concentration of the indicated cytokines by ELISA. The results show that IFN-gamma is not produced to an appreciable extent by RAW Blue macrophages stimulated with these compounds.

Example 2

Immuno-Oncology and Immunotherapies

Immunotherapeutic SNAs (i.e., AST-008) provide a novel and versatile technology platform. Their multi-valent immunomodulator delivery optimizes responses, while profound tumor reduction in a lymphoma model has been observed. Additionally, they trigger a potent and balanced T cell response in vivo greater than that of free oligonucleotide or alum. SNAs can co-present therapeutic vaccine antigen and adjuvant on a single nanoparticle and have enhanced activity and faster kinetics than free immunostimulatory CpG oligodeoxynucleotides. Furthermore, SNAs have the potential to simultaneously target multiple immunostimulatory receptors (e.g. TLR 3, 4, 7/8, 9). They can be used, for example, in cancer immunotherapy and vaccines (prophylactic or therapeutic).

Figure 15:
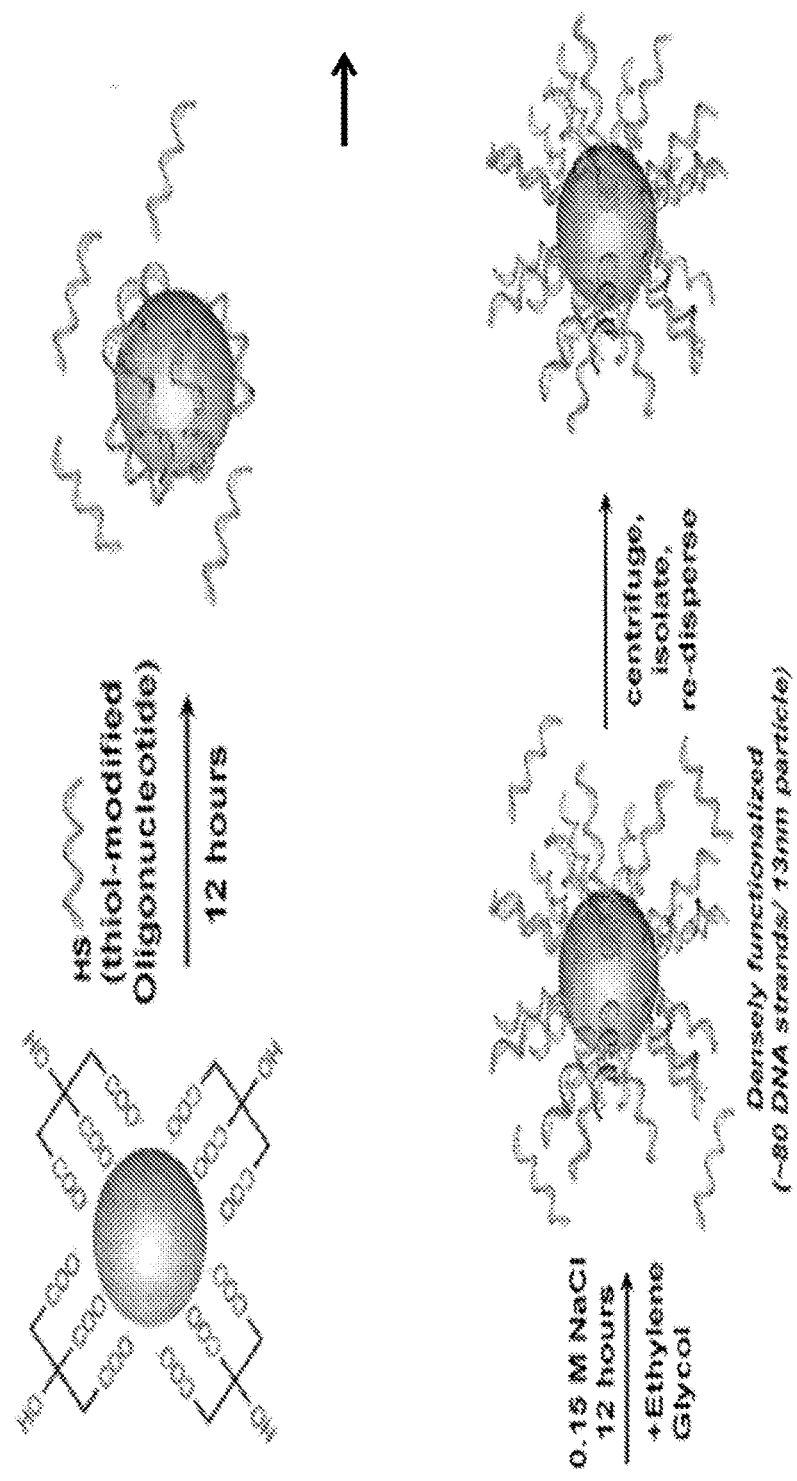
FIG. 15 shows a representation of an immunotherapeutic SNA (AST-008).

A schematic of an immunotherapeutic SNA (AST-008) is shown in FIG. 15. The SNAs can co-present a therapeutic vaccine antigen and adjuvant on a single nanoparticle, and may simultaneous target multiple immunostimulatory receptors (e.g. TLR 3, 4, 7/8, 9).

Figure 16:
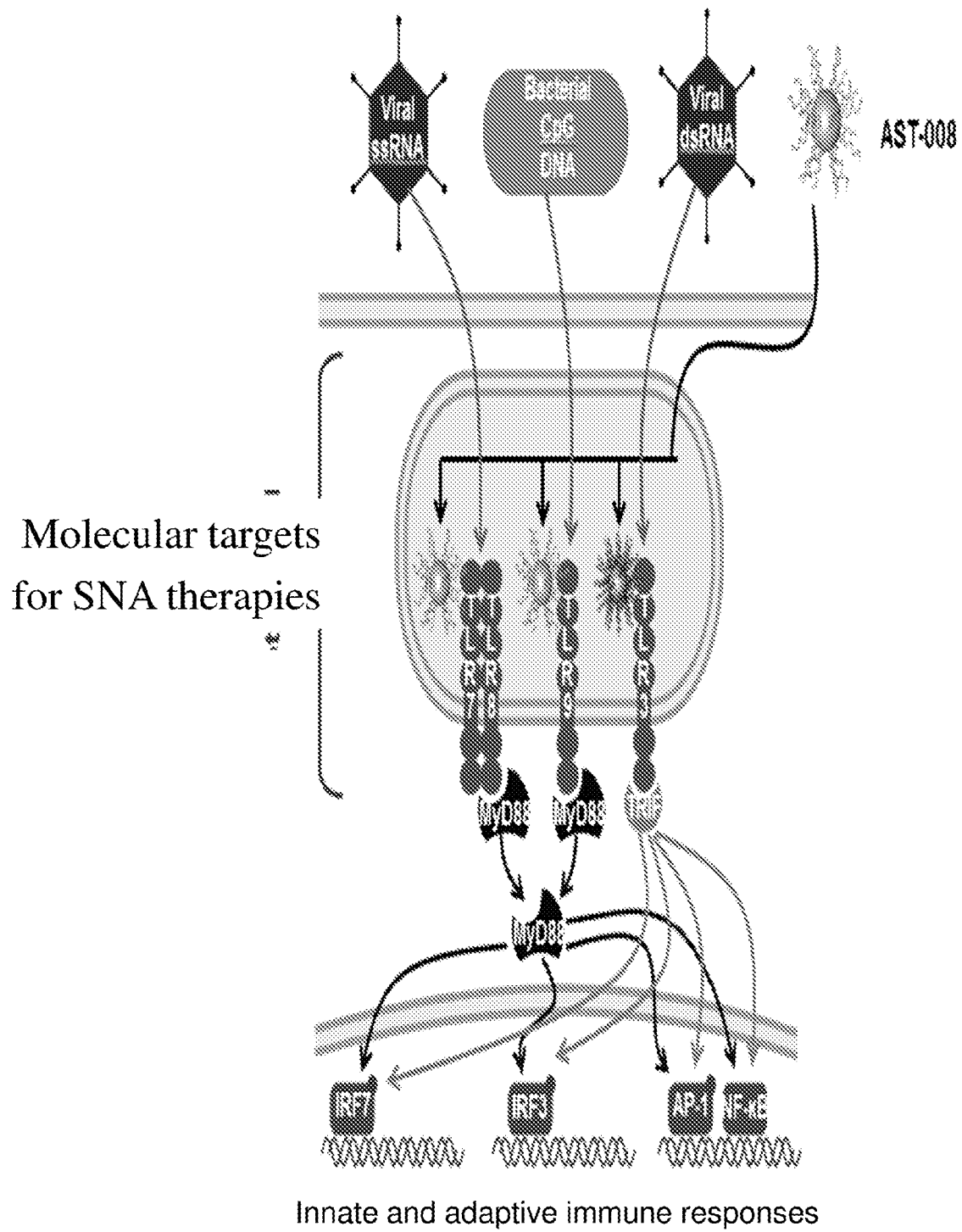
FIG. 16 is a schematic demonstrating how AST-008 can enter endosomes via triggered endocytosis, where it then can be used for versatile immune system stimulation. Within the endosome, AST-008 stimulates immune system signaling via the TLR 9 receptor, a molecular target for SNA therapy, leading to both innate and adaptive immune responses. AST-008 may also target TLR 3, 4, 7/8, resulting in innate and adaptive immune responses.

A schematic demonstrating how AST-008 can enter endosomes via triggered endocytosis is shown in FIG. 16. AST-008 once in the endosomes can be used for versatile immune system stimulation. Within the endosome, AST-008 stimulates immune system signaling via the TLR 9 receptor, a molecular target for SNA therapy, leading to both innate and adaptive immune responses. AST-008 may also target TLR 3, 4, 7/8, resulting in innate and adaptive immune responses.

Figure 17:
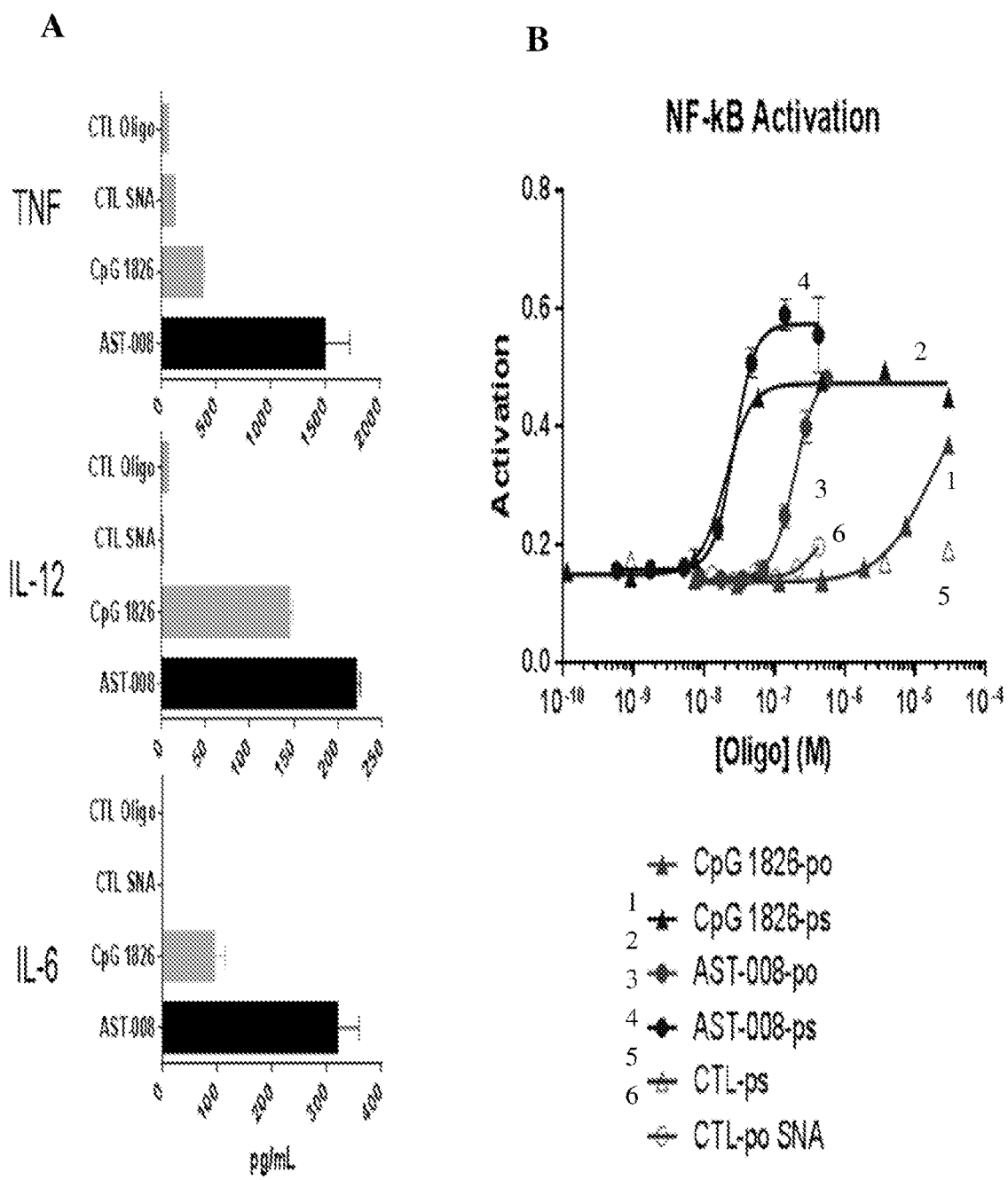
FIGS. 17A and 17B are a set of graphs showing that AST-008 induces higher pro-inflammatory responses than corresponding CpG oligodeoxynucleotides (oligo) in vitro.

AST-008 induces higher pro-inflammatory responses than corresponding CpG oligodeoxynucleotides (oligo) in vitro. An assay demonstrating this finding was conducted. The data is shown as a set of graphs in FIGS. 17A and 17B. FIG. 17A shows the expression levels of TNF, IL-12, and IL-6 induced by CTL oligo, CTL SNA, CpG 1826, and AST-008. FIG. 17B presents the NF-κB activation stemming from the indicated agents.

Figure 18:
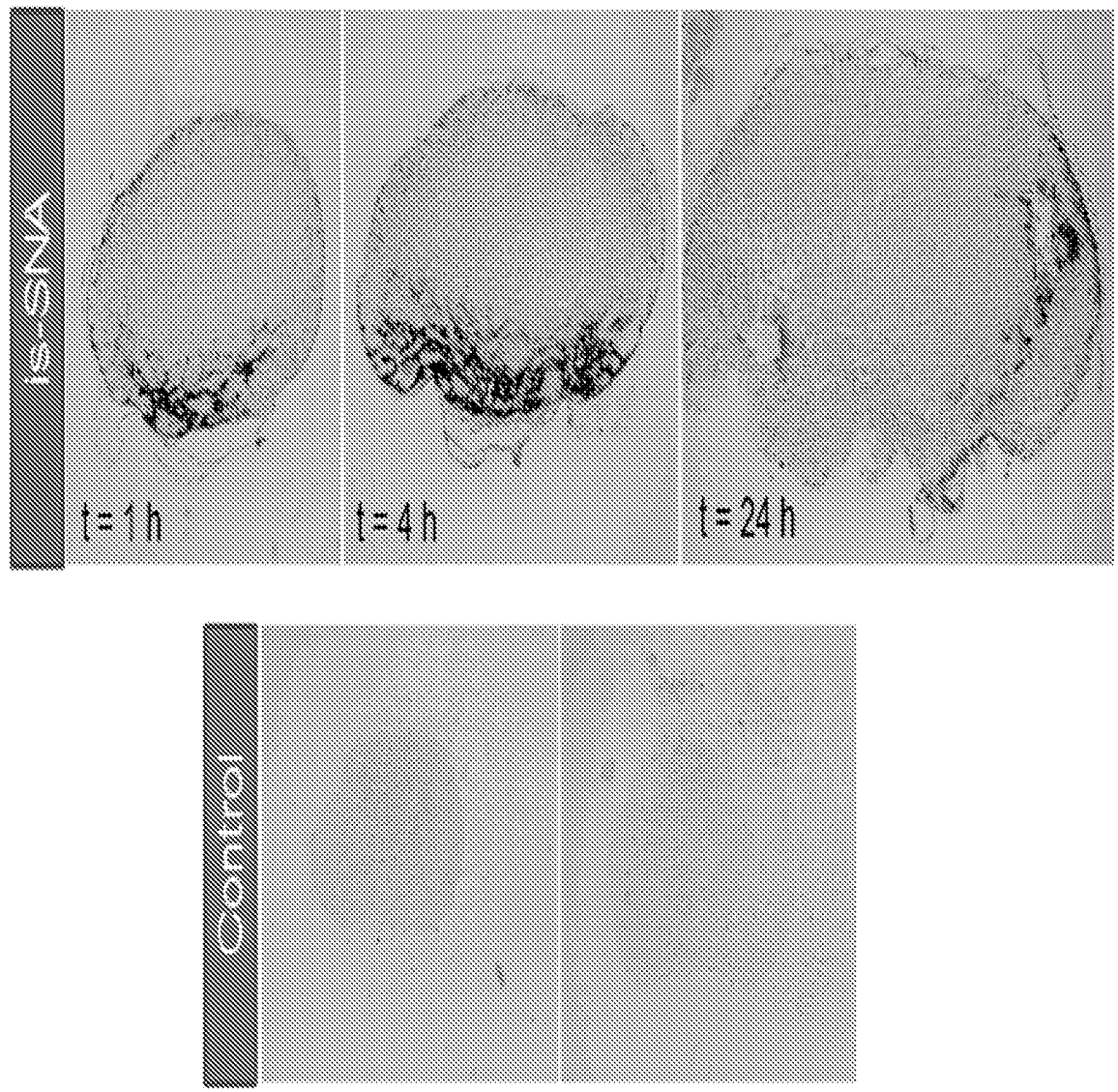
FIG. 18 demonstrates that AST-008 targets draining lymph nodes after administration of a single subcutaneous dose. AST-008 was silver-stained to enhance light scattering of the gold core, and then counterstained with eosin. 4× bright field magnification was used.

AST-008 also targets draining lymph nodes after administration of a single subcutaneous dose. AST-008 was silver-stained to enhance light scattering of the gold core, and then counterstained with eosin. 4× bright field magnification was used. The data is shown in FIG. 18.

Figure 19:
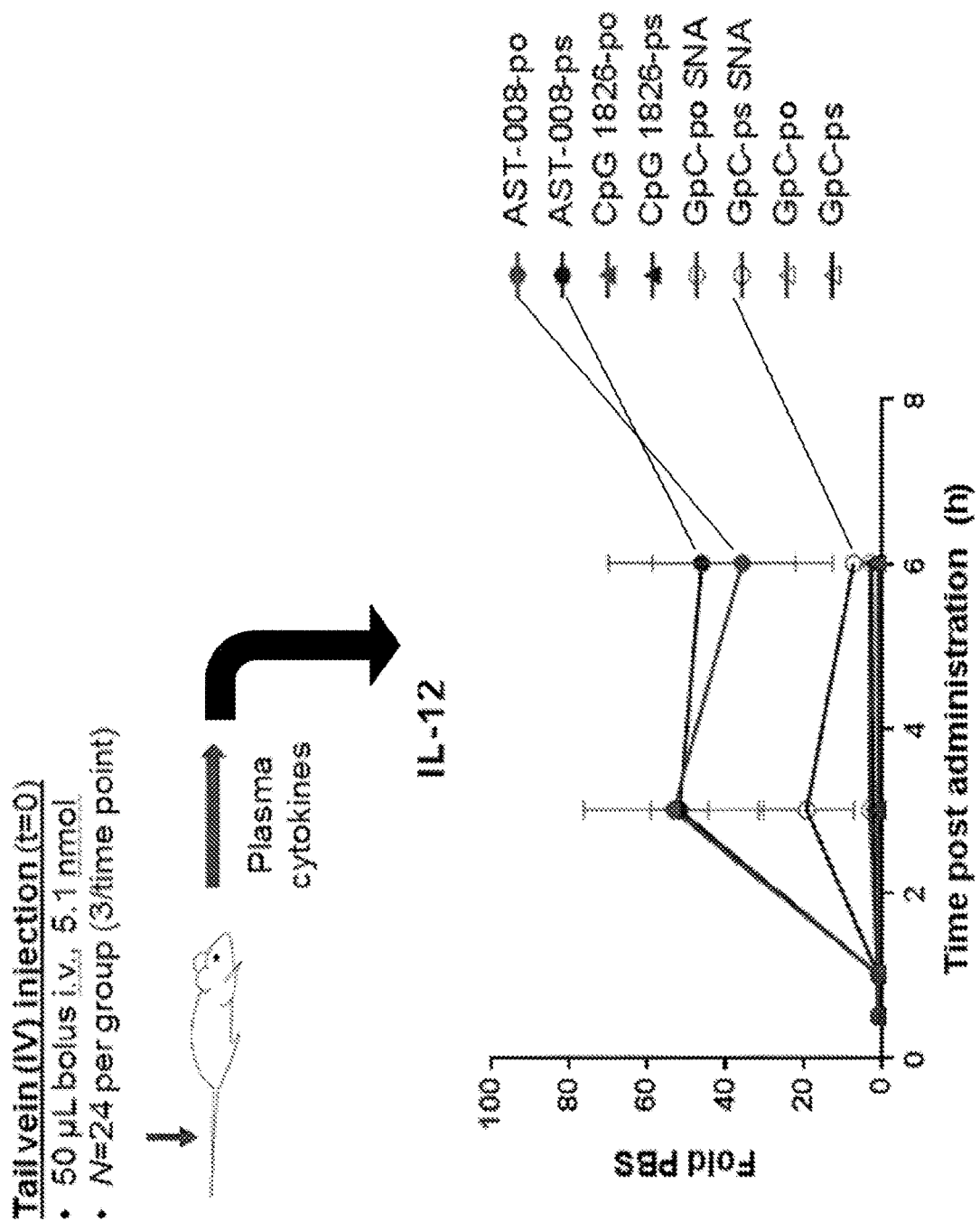
FIG. 19 is a graph illustrating the in vivo activity of AST-008. Mice were given a 50 µL bolus tail vein (intravenous) injection of 5.1 nmol solution (AST-008-po, AST-008-ps, CpG 1826-po, CpG 1826-ps, GpC-po SNA, GpC-ps SNA, GpC-po, or GpC-ps) and then analyzed for IL-12 expression 1, 3, and 6 hours after injection (24 mice per group, 3 per each time point). IL-12 levels are expressed as the fold over PBS. AST-008 architecture enhances the induction of IL-12 by approximately 20-fold over free oligodeoxynucleotides, and the effect was sustained for over six hours after the initial administration.
Figure 20:
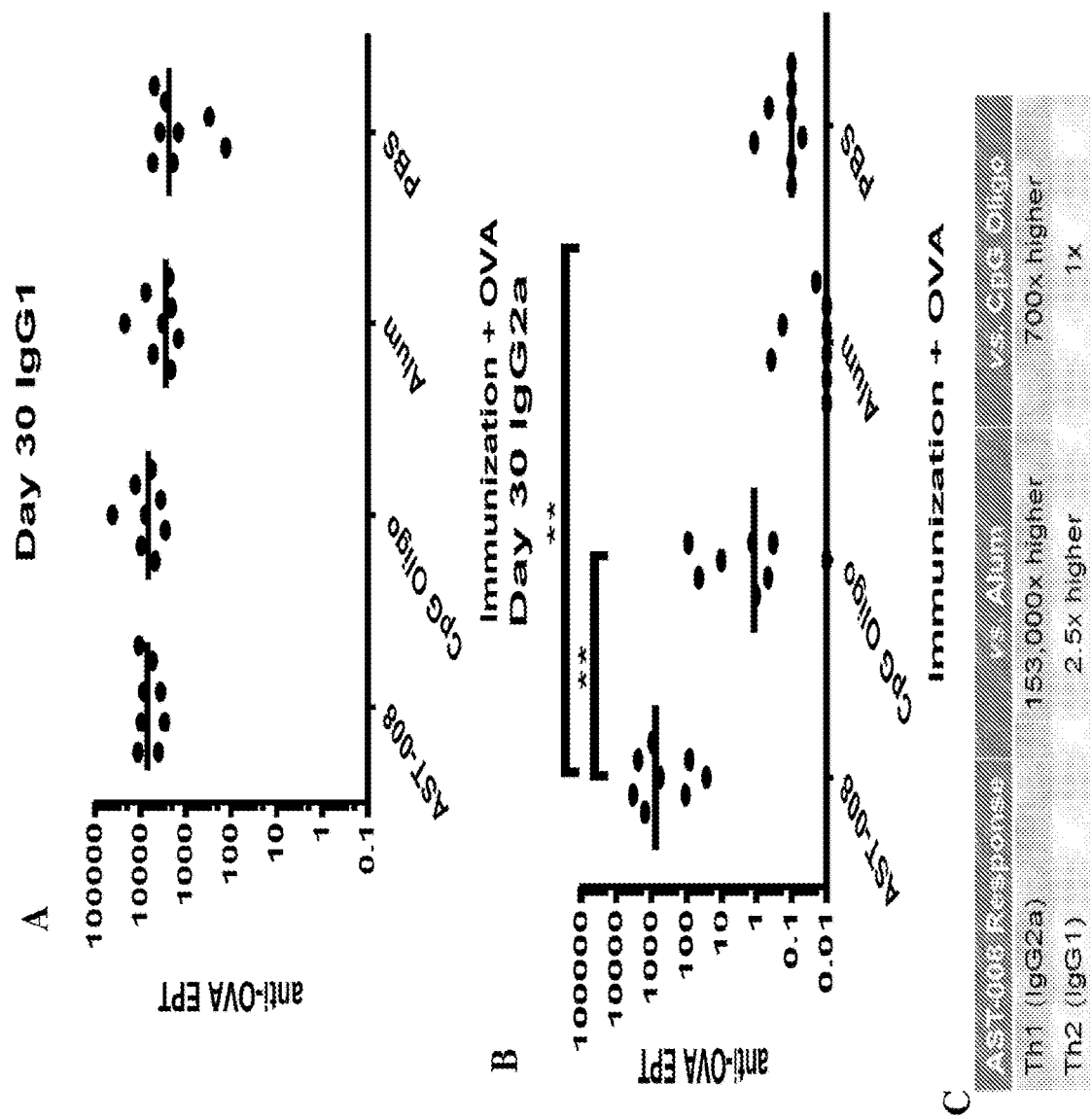
FIGS. 20A-20C consist of a pair of graphs and a chart that demonstrate that AST-008 induces both a balanced Th1/Th2 response (FIG. 20A) and a higher IgG2a antibody (FIG. 20B) response than alum or CpG oligonucleotides. The results are tabulated in FIG. 20C. **p<0.01.
Figure 21:
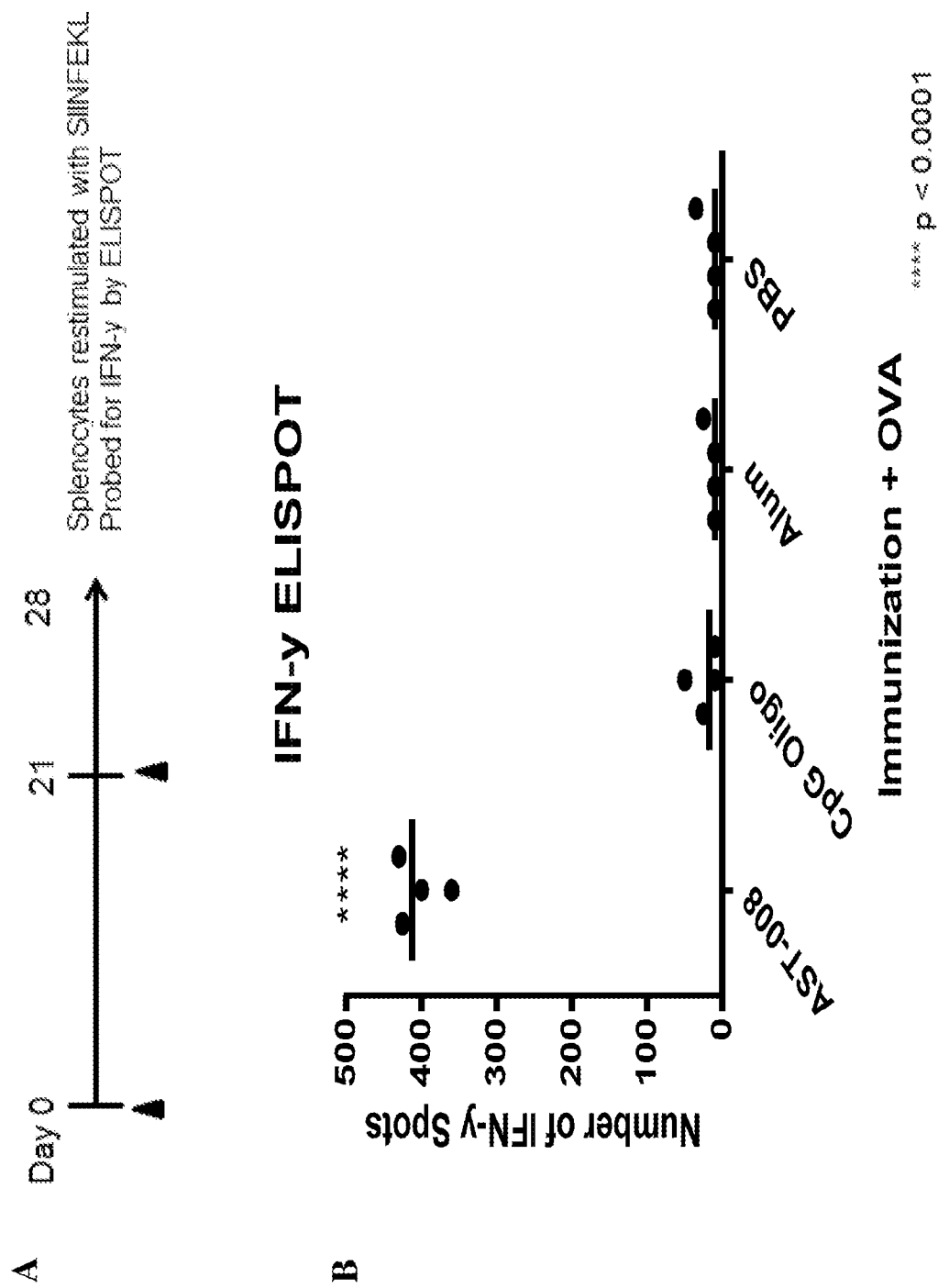
FIGS. 21A-21B show that AST-008 induces cellular responses more effectively than alum or CpG oligonucleotides.
Figure 22:
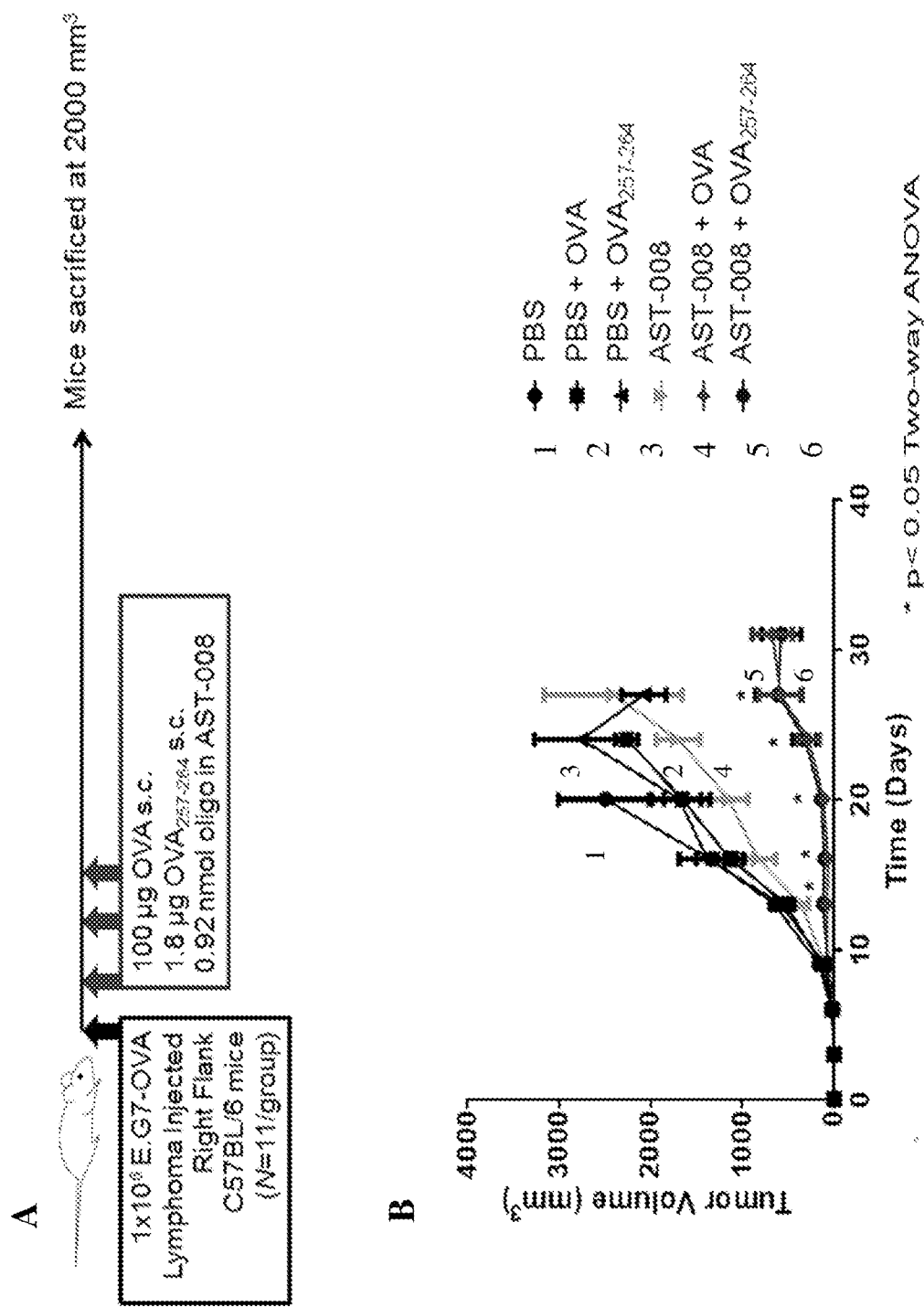
FIGS. 22A-22B demonstrate that AST-008 induces a profound tumor-clearing immune response in an in vivo lymphoma model.
Figure 23:
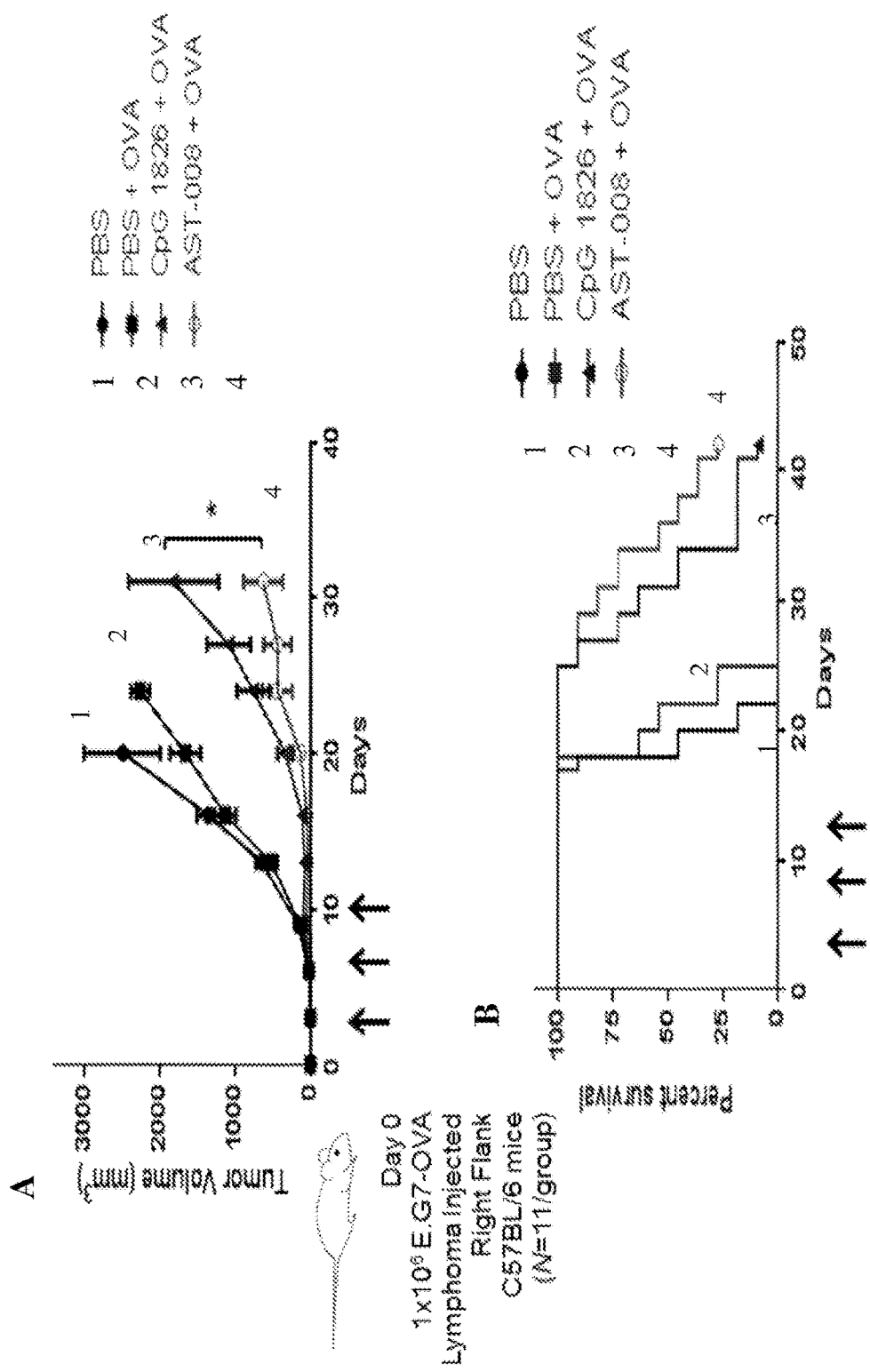
FIGS. 23A-23B show that AST-008 exhibits superior anti-tumor activity and longer survival than CpG oligodeoxynucleotides. The graphs show the tumor volume (FIG. 23A) and percent survival (FIG. 23B) after C57BL/6 mice were injected with 1×10$^6$ E.G7-OVA lymphoma in their right flanks (11 per group) and then were challenged three times with PBS, PBS and OVA, CpG 1826 and OVA, or AST-008 and OVA. *p<0.05.

The structures of the invention are useful for stimulating a robust immune response in vivo. For instance, FIG. 19 is a graph illustrating the in vivo activity of AST-008. Mice were given a 50 µL bolus tail vein (intravenous) injection of 5.1 nmol solution (AST-008-po, AST-008-ps, CpG 1826-po, CpG 1826-ps, GpC-po SNA, GpC-ps SNA, GpC-po, or GpC-ps) and then analyzed for IL-12 expression 1, 3, and 6 hours after injection (24 mice per group, 3 per each time point). IL-12 levels are expressed as the fold over PBS. AST-008 architecture enhances the induction of IL-12 by approximately 20-fold over free oligodeoxynucleotides, and the effect was sustained for over six hours after the initial administration. FIGS. 20A-20C consist of a pair of graphs and a chart that demonstrate that AST-008 induces both a balanced Th1/Th2 response (FIG. 20A) and a higher IgG2a antibody (FIG. 20B) response than alum or CpG oligonucleotides. The results are tabulated in FIG. 20C. p<0.01. FIGS. 21A-21B show that AST-008 induces cellular responses more effectively than alum or CpG oligonucleotides. FIG. 21A schematically represents the protocol: splenocytes were grown for 28 days, challenged on Day 0 and Day 21, and then restimulated with SIINFEKL and probed for INF-γ with ELISPOT on Day 28. FIG. 21B is a graph depicting the results. **p<0.0001. The structures have been shown to produce a dramatic anti-tumor response in vivo as well. FIGS. 22A-22B demonstrate that AST-008 induces a profound tumor-clearing immune response in an in vivo lymphoma model. FIG. 22A illustrates the protocol: the right flanks of C57BL/6 mice were injected with $1 \times 10^6$ E.G7-OVA lymphoma (11 per group). The mice were then challenged three times with 100 µg OVA s.c., 1.8 µg $OVA_{257-264}$ s.c., and 0.92 nmol oligo in AST-008, and sacrificed at 2000 mm³. FIG. 13B is a graph of the results. *p<0.05 using Two-way ANOVA. FIGS. 23A-23B show that AST-008 exhibits superior anti-tumor activity and longer survival than CpG oligodeoxynucleotides. The graphs show the tumor volume (FIG. 23A) and percent survival (FIG. 23B) after C57BL/6 mice were injected with $1 \times 10^6$ E.G7-OVA lymphoma in their right flanks (11 per group) and then were challenged three times with PBS, PBS and OVA, CpG 1826 and OVA, or AST-008 and OVA. *p<0.05.

TABLE 1

Key to symbols

| Name | Oligo Sequence (5'-3') | Formulation | SEQ ID NO: |
|---|---|---|---|
| AST-007-po, CpG 1668 PO SNA | TCCATGACGTTCCTGATGCT/iSp18//iSp18//iSp18//3ThioMC3-D/ | Conjugated to 13 nm gold core via thio-gold bond | 36 |
| AST-008-po, CpG 1826 PO SNA | TCCATGACGTTCCTGACGTT/iSp18//iSp18//3ThioMC3-D/ | Conjugated to 13 nm gold core via thio-gold bond | 37 |
| AST-009-po, CpG 7909 PO SNA | TCGTCGTTTTGTCGTTTTGTCGTT/iSp18//iSp18//3ThioMC3-D/ | Conjugated to 13 nm gold core via thio-gold bond | 38 |
| AST-007-ps, CpG 1668 PS SNA | tccatgacgttcctgatgct/iSp18//iSp18//iSp18//3ThioMC3-D/ | Conjugated to 13 nm gold core via thio-gold bond, backfilled with tetraethylene glycol | 39 |
| AST-008-ps, CpG 1826 PS SNA | tccatgacgttcctgacgtt/iSp18//iSp18//3ThioMC3-D/ | Conjugated to 13 nm gold core via thio-gold bond, backfilled with tetraethylene glycol | 40 |
| AST-009-ps, CpG 7909 PS SNA | tcgtcgttttgtcgttttgtcgtt/iSp18//iSp18//3ThioMC3-D/ | Conjugated to 13 nm gold core via thio-gold bond, backfilled with tetraethylene glycol | 41 |
| CpG 1826-po | TCCATGACGTTCCTGACGTT | Free | 42 |
| CpG 1826-ps | Tccatgacgttcctgacgtt | Free | 43 |
| CpG 1668-po | TCCATGACGTTCCTGATGCT | Free | 44 |

TABLE 1-continued

Key to symbols

| Name | Oligo Sequence (5'-3') | Formulation | SEQ ID NO: |
|---|---|---|---|
| CpG 1668-ps | Tccatgacgttcctgatgct | Free | 45 |
| CpG 7909-po | TCGTCGTTTTGTCGTTTTGTCGTT | Free | 46 |
| CpG 7909-ps | Tcgtcgttttgtcgttttgtcgtt | Free | 47 |
| rplV-po | GCTTTCTTGTTGGTGTAGGTC | Free | 48 |
| rplV-ps | Gctttcttgttggtgtaggtc | Free | 49 |
| Ctrl-SNA-po, rplV SNA PO | Sequence containing no CpG motifs, all phosphodiester linkages | Conjugated to 13 nm gold core via thio-gold bond | |
| Ctrl-SNA-ps, rplV SNA PS | Sequence containing no CpG motifs, all phosphorothioate linkages | Conjugated to 13 nm gold core via thio-gold bond | |

Lowercase indicates phosphorothioate linkages
Capital indicates phosphodiester linkages
Prefix "Ctrl" indicates oligo used with no CpG motifs present
/iSp18/ internal spacer-18
/3ThioMC3-D/ terminal sulfhydryl group

REFERENCES

1. Koff W C et al. Science 340:1232910-1 (2013)
2. Cluff C W. Monophosphoryl Lipid A (MPL) as an Aduvant for Anti-Cancer Vaccines: Clinical Results. Lipid A in Cancer Therapy, Jeannin J Ed. Landes Bioscience (2000)
3. Krieg A M. Proc Am Thorac Soc 4:289 (2007)
4. Schmidt C. Nat Biotechnol 25:825 (2007)
5. Ellis R D et al. PLOS One 10:e46094 (2012)
6. Garcon N et al. Expert Rev. Vaccines 6:723 (2007)
7. Rosi N L et al. Science 312:1027 (2006)
8. Lytton-Jean A K et al. JACS 127:12754 (2005)
9. Hurst S J et al. Anal. Chem. 78:8313 (2006)
10. Patel P C et al. PNAS 105:17222 (2008)
11. Seferos D S et al. Nano Lett 9:308 (2009)
12. Giljohann et al. Angew. Chem. Int. Ed. 49:3280 (2010)

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A method of treating a subject, comprising administering to the subject a nanoscale construct in an effective amount to stimulate an immune response, wherein the nanoscale construct comprises a corona having an exterior shell composed of nucleic acid molecules arranged in a geometrical position around a nanoparticle core, wherein the nucleic acid molecules have a surface density of at least 0.3 pmol/cm$^2$, are CpG oligonucleotides, and contain a spacer which comprises an oligoethylene, wherein the nucleic acid molecules do not comprise an oligonucleotide spacer, and wherein the nanoparticle core is about 1 nm to about 40 nm in mean diameter.

2. The method of claim 1, wherein the subject has cancer.

3. The method of claim 2, wherein the cancer is biliary tract cancer, brain cancer, breast cancer, cervical cancer, choriocarcinoma, colon cancer, endometrial cancer, esophageal cancer, gastric cancer, an intraepithelial neoplasm, lymphoma, liver cancer, lung cancer, melanoma, neuroblastoma, oral cancer, ovarian cancer, pancreas cancer, prostate cancer, rectal cancer, sarcomas, testicular cancer, thyroid cancer, renal cancer, hairy cell leukemia, chronic myelogenous leukemia, cutaneous T-cell leukemia, multiple myeloma, renal cell carcinoma, lymphoma, bladder cancer, non-small cell lung cancer (NSCLC), or glioblastoma multiforme.

4. The method of claim 2, wherein the cancer is squamous cell carcinoma.

5. The method of claim 2, wherein the cancer is skin cancer.

6. The method of claim 1, wherein the nanoscale construct is administered to the subject through oral, parenteral, intramuscular, intravenous, mucosal, intranasal, sublingual, intratracheal, inhalation, ocular, vaginal, dermal or rectal routes of administration.

7. The method of claim 1, wherein the nanoscale construct is administered to the subject through a subcutaneous route of administration.

8. The method of claim 1, wherein the nanoscale construct is administered to the subject through direct injection to one or more cancer cells.

9. The method of claim 1, wherein the oligoethylene is a hexaethylene glycol.

10. The method of claim 1, wherein the CpG oligonucleotides have a phosphorothioate (PS) backbone.

11. The method of claim 1, wherein the subject is human.

12. The method of claim 1, wherein the CpG oligonucleotides comprise the sequence of SEQ ID NO: 30.

13. The method of claim 1, wherein the surface density is no greater than about 35-40 pmol/cm$^2$.

14. The method of claim 1, wherein the CpG oligonucleotides are 6 to 100 nucleotides in length.

15. The method of claim 1, wherein the nucleic acid molecules are linked to other nucleic acid molecules through a non-covalent linkage.

16. The method of claim 1, wherein the CpG oligonucleotides have at least one phosphodiester internucleotide linkage.

* * * * *

SEQUENCE LISTING

<160> NUMBER OF SEQ ID NOS: 49

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
tccatgacgt tcctgacgtt                                            20

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 2

```
gctttcttgt tggtgtaggt c                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
tccatgacgt tcctgatgct                                                20

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 4
gctttcttgt tggtgtaggt c                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
tccatgacgt tcctgatgct                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
tccatgacgt tcctgatgct                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
tccatgacgt tcctgatgct                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
tccatgacgt tcctgatgct                                                20

<210> SEQ ID NO 9
<211> LENGTH: 20
<212> TYPE: DNA
```

```
<213> ORGANISM: Artificial Sequence
<220> FEATURE:
<223> OTHER INFORMATION: Synthetic Polynucleotide

<400> SEQUENCE: 9
tccatgacgt tcctgacgtt                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
tccatgacgt tcctgacgtt                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
tccatgacgt tcctgacgtt                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
tccatgacgt tcctgacgtt                                               20

<210> SEQ ID NO 13
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 13
ccgucuguug ugugacuc                                                 18

<210> SEQ ID NO 14
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 14
gccaccgagc cgaaggcacc                                               20

<210> SEQ ID NO 15
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 15
uauauauaua uauauauaua                                               20
```

```
<210> SEQ ID NO 16
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 16
uuauuauuau uauuauuauu                                               20

<210> SEQ ID NO 17
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 17
uuuuauuuua uuuuauuuua                                               20

<210> SEQ ID NO 18
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 18
ugugugugug ugugugugug                                               20

<210> SEQ ID NO 19
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 19
uuguuguugu uguuguuguu                                               20

<210> SEQ ID NO 20
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 20
uuuguuuguu uguuuguuug                                               20

<210> SEQ ID NO 21
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 21
uuauuuauuu auuuauuuau uuau                                          24

<210> SEQ ID NO 22
<211> LENGTH: 24
<212> TYPE: RNA
<213> ORGANISM: Artificial Sequence
<220> FEATURE:
```

<223> OTHER INFORMATION: Synthetic Polynucleotide

<400> SEQUENCE: 22
uuguuuguuu guuuguuugu uugu                                          24

<210> SEQ ID NO 23
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 23
gcccgucugu ugugugacuc                                               20

<210> SEQ ID NO 24
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 24
guccuucaag uccuucaa                                                 18

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 25
ggtgcatcga tgcagggggg                                               20

<210> SEQ ID NO 26
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 26
tccatggacg ttcctgagcg tt                                            22

<210> SEQ ID NO 27
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 27
tcgtcgttcg aacgacgttg at                                            22

<210> SEQ ID NO 28
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 28
tcgtcgacga tccgcgcgcg cg                                            22

```
<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
ggggtcaacg ttgagggggg                                            20

<210> SEQ ID NO 30
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 30
tcgtcgtttt gtcgttttgt cgtt                                       24

<210> SEQ ID NO 31
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 31
tcgtcgttgt cgttttgtcg tt                                         22

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32
gggggacgat cgtcgggggg                                            20

<210> SEQ ID NO 33
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 33
ggggacgacg tcgtggggggg g                                         21

<210> SEQ ID NO 34
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 34
tcgtcgtttt cggcgcgcgc cg                                         22

<210> SEQ ID NO 35
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 35
tcgtcgtcgt tcgaacgacg ttgat                                    25

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 36
tccatgacgt tcctgatgct                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 37
tccatgacgt tcctgacgtt                                          20

<210> SEQ ID NO 38
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 38
tcgtcgtttt gtcgttttgt cgtt                                     24

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 39
tccatgacgt tcctgatgct                                          20

<210> SEQ ID NO 40
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 40
tccatgacgt tcctgacgtt                                          20

<210> SEQ ID NO 41
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 41
tcgtcgtttt gtcgttttgt cgtt                                     24

<210> SEQ ID NO 42
<211> LENGTH: 20
```

```
<212> TYPE: DNA
<213> ORGANISM: Artificial Sequence
<220> FEATURE:
<223> OTHER INFORMATION: Synthetic Polynucleotide

<400> SEQUENCE: 42
tccatgacgt tcctgacgtt                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
tccatgacgt tcctgacgtt                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 44
tccatgacgt tcctgatgct                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 45
tccatgacgt tcctgatgct                                              20

<210> SEQ ID NO 46
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 46
tcgtcgtttt gtcgttttgt cgtt                                         24

<210> SEQ ID NO 47
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 47
tcgtcgtttt gtcgttttgt cgtt                                         24

<210> SEQ ID NO 48
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 48
```

```
gctttcttgt tggtgtaggt c                                          21

<210> SEQ ID NO 49
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 49
gctttcttgt tggtgtaggt c                                          21
```